(12) United States Patent
Fukuju et al.

(10) Patent No.: US 7,919,044 B2
(45) Date of Patent: Apr. 5, 2011

(54) SAMPLE ANALYZER AND ITS COMPONENTS

(75) Inventors: Toshikatsu Fukuju, Akashi (JP); Takaaki Nagai, Kobe (JP); Shuhei Kaneko, Kobe (JP); Hidenari Takaoka, Kobe (JP); Noriyoshi Yoshida, Kobe (JP); Takashi Yoshida, Akashi (JP)

(73) Assignee: Sysmex Corporation, Kobe (JP)

( * ) Notice: Subject to any disclaimer, the term of this patent is extended or adjusted under 35 U.S.C. 154(b) by 705 days.

(21) Appl. No.: 11/925,478

(22) Filed: Oct. 26, 2007

(65) Prior Publication Data

US 2008/0063568 A1    Mar. 13, 2008

Related U.S. Application Data

(62) Division of application No. 10/713,302, filed on Nov. 17, 2003, now Pat. No. 7,427,376.

(30) Foreign Application Priority Data

| Nov. 18, 2002 | (JP) | 2002-334243 |
| Nov. 18, 2002 | (JP) | 2002-334251 |
| Nov. 18, 2002 | (JP) | 2002-334272 |
| Nov. 18, 2002 | (JP) | 2002-334286 |
| Nov. 18, 2002 | (JP) | 2002-334293 |
| Jul. 8, 2003 | (JP) | 2003-193715 |

(51) Int. Cl.
    *G01N 33/00* (2006.01)
(52) U.S. Cl. ............ 422/63; 422/55; 422/56; 422/68.1; 422/81; 422/99
(58) Field of Classification Search .................... 422/55, 422/56, 63, 68.1, 81, 99
See application file for complete search history.

(56) References Cited

U.S. PATENT DOCUMENTS

| 3,063,451 A | 11/1962 | Kowalk |
| 4,743,243 A | 5/1988 | Vaillancourt |
| 5,073,343 A | 12/1991 | Hukuhara et al. |
| 5,380,665 A * | 1/1995 | Cusack et al. .................. 436/53 |
| 5,969,272 A | 10/1999 | Tanaka |

FOREIGN PATENT DOCUMENTS

| JP | 4-301769 A | 10/1992 |
| JP | 5-62859 U | 8/1993 |
| JP | 8-233698 A | 9/1996 |
| JP | 10-300641 A | 11/1998 |
| JP | 11-44691 A | 2/1999 |
| JP | 11-94842 A | 4/1999 |
| WO | WO-95/18962 A | 7/1995 |
| WO | WO-97/14967 A | 4/1997 |
| WO | WO-00/69389 A | 11/2000 |

\* cited by examiner

*Primary Examiner* — Sam P Siefke
(74) *Attorney, Agent, or Firm* — Birch, Stewart, Kolasch & Birch, LLP

(57) ABSTRACT

A sample analyzer includes a liquid aspirator to be stuck into the closed container for aspirating a sample from a closed container; a preparing section for preparing an analysis sample using the aspirated sample; and an analyzing section for analyzing the prepared analysis sample; the liquid aspirator including an elongated pipe, the pipe having a liquid flow path extending therein and a plurality of communicating sections provided in an outer surface thereof, at least one of the communicating sections communicating between an inside and an outside of the container when the pipe is stuck into the container.

13 Claims, 53 Drawing Sheets

SAMPLE ANALYZER AND ITS COMPONENTS

CROSS-REFERENCES TO RELATED APPLICATIONS

This application is a Divisional of application Ser. No. 10/713,302, filed on Nov. 17, 2003, now U.S. Pat. No. 7,427,376 the entire contents of which are hereby incorporated by reference and for which priority is claimed under 35 U.S.C. §120.

This application is related to Japanese Patent Application Nos. 2002-334243 (filed on Nov. 18, 2002), 2002-334251 (filed on Nov. 18, 2002), 2002-334272 (filed on Nov. 18, 2002), 2002-334286 (filed on Nov. 18, 2002), 2002-334293 (filed on Nov. 18, 2002), and 2003-193715 (filed on Jul. 8, 2003) whose priorities are claimed under 35 U.S.C. §119, the disclosures of which are incorporated by reference in their entirety.

BACKGROUND OF THE INVENTION

1. Field of the Invention

This invention relates to a sample analyzer for analyzing a blood sample, a urine sample and the like and its components used therein and, particularly, to a versatile and portable sample analyzer.

2. Description of Related Art

Art hitherto known in relation to this invention is as follows.

A small-scale automatic analyzer comprising a reaction vessel disk having a reaction table with its circumferential portion equidistantly divided into a plurality of portions, a plurality of reaction vessels held by the reaction vessel disk, means for transporting the respective reaction vessels to a sample dispenser, to an agent dispensing position and to an optically measuring position, means for sucking and dispensing a required amount of a sample into the reaction vessel, and means for optically analyzing the sample in the reaction vessel (see, for example, Japanese Unexamined Patent Publication No. 11-94842 (1999));

A pipette comprising a hollow pipe having an end sealed with a seal member, and a suction port provided in a side wall of the pipe adjacent to the vicinity of the end (see, for example, U.S. Pat. No. 5,969,272); and A pipette comprising a thin suction pipe for sucking a liquid sample, and a thin vent pipe for ventilation during the suction, the suction pipe and the vent pipe being disposed in parallel (see, for example, U.S. Pat. No. 5,969,272).

There have been proposed various types of blood analyzers for analyzing samples, for example, blood. Most of the recent blood analyzers have a greater size and a higher operation speed to handle a multiplicity of samples in a short time. In addition, the operation of the blood analyzers is complicated, so that special operators should be employed as regular staff. Local hospitals and private clinics which do not frequently need blood analyses currently commission a special blood analysis center to perform the blood analyses. However, it is impossible to immediately obtain the results of blood analyses in an emergency case. Therefore, there is a demand for a highly accurate, easy-to-operate and small-scale automatic blood analyzer.

Such a demand is applied to not only the blood analyzer but also a urine analyzer and the like.

In such a sample analyzer, it is preferred to employ a so-called AD system (Autodilution system) in which the liquid sample is sucked and quantified by a suction device such as a syringe pump having a pipette so that the analyzer may have a smaller scale with its more simplified construction. However, in the case of this system, when the pipette is inserted in a vacuum blood sampling tube (a rubber-capped tube) employed as a sample container, a negative pressure is liable to remain in the vacuum blood sampling tube. Accordingly, the sucking operation of the suction device is not smoothly performed, resulting in erroneous quantification. Thus, there is a problem that the analysis of the sample cannot be performed accurately.

On the other hand, if a conventional vent pipe is attached to the pipette in parallel, the analyzer needs to further provide a cleaning flow system for cleaning the vent pipe, so that the construction of the analyzer is complicated.

SUMMARY OF THE INVENTION

In view of the foregoing, it is an object of the present invention to simplify the operation of a sample analyzer for easy handling of the analyzer by doctors and nurses, reduce the size and weight of the analyzer for easy transportation of the analyzer to diagnostic and medical treatment sites, suppress the noises of the analyzer for a quiet environment, and ensure safe and easy maintenance and inspection of the analyzer, and particularly obtain the highly accurate results of sample analyses even with the use of the analyzer having a simple construction.

The present invention provides a sample analyzer comprising: a liquid aspirator to be stuck into the closed container for aspirating a sample from a closed container; a preparing section for preparing an analysis sample using the aspirated sample; and an analyzing section for analyzing the prepared analysis sample; the liquid aspirator including an elongated pipe, the pipe having a liquid flow path extending therein and a plurality of communicating sections provided in an outer surface thereof, at least one of the communicating sections communicating between an inside and an outside of the container when the pipe is stuck into the container.

In accordance with one aspect of this invention, there is provided a liquid aspirator for aspirating liquid from a closed container, comprising: an elongated pipe having a liquid flow path extending therein and a plurality of communicating sections; wherein the communicating sections are provided in an outer surface of the pipe for communicating between an inside and an outside of the container when the pipe is stuck into the container.

In accordance with another aspect of this invention, there is provided a liquid aspirator for aspirating a liquid from a closed container, comprising: an elongated pipe having a liquid flow path extending therein and a head section tapered toward a tip thereof; wherein the tip is positioned on an axis of the pipe.

In accordance with further another aspect of this invention, there is provided a sample analyzer comprising; a preparing section for preparing an analysis sample using a sample; an analyzing section for analyzing the prepared analysis sample; first and second flow paths for transporting liquid to the preparing section; first and second valves for opening and closing the first and second flow paths, respectively; first and second air bubble sensors for sensing an air bubble in the first and second flow paths, respectively, each air bubble sensor outputting a signal; and a controller for controlling the first and second valves so that the valves are selectively opened, wherein the controller judges whether the air bubble is present in the flow path opened by the valve based on the signals outputted from the first and second air bubble sensors.

In accordance with still another aspect of this invention, there is provided an air bubble detector comprising: first and second air bubble sensors for sensing an air bubble in first and second flow paths, respectively, each air bubble sensor outputting a logical pulse signals representing a sensing time period of the air bubble in pulse width; and an integrating section for integrating pulse widths of the logical pulse signal outputted from each sensor during a time period.

In accordance with still another aspect of this invention, there is provided a sample analyzer comprising: an adaptor for holding a sample container containing a sample; a rack for removably receiving the adaptor; a preparing section for preparing an analysis sample from the sample; and an analyzing section for analyzing the prepared analysis sample; wherein the adaptor comprises a sample container supporting section for receiving the sample container and a receiving tray for receiving the sample to be spilled from the sample container.

In accordance with yet another aspect of this invention, there is provided an adaptor which is removably inserted in a rack of a sample analyzer to hold a sample container containing a sample, comprising: a sample container supporting section for receiving the sample container; and a receiving tray for receiving the sample to be spilled from the sample container.

In accordance with still another aspect of this invention, there is provided a sample analyzer comprising: a preparing section for preparing an analysis sample to be analyzed; and an analyzing section for analyzing the prepared analysis sample, wherein the preparing section comprises a syringe pump unit used for preparing the analysis sample, the syringe pump unit including: a first syringe pump having a first cylinder and a first piston to be inserted in the first cylinder; a second syringe pump having a second cylinder and a second piston to be inserted in the second cylinder; a connecting section provided between the first syringe pump and the second syringe pump for connecting the first piston and the second piston; and a driving source for driving the first and second pistons through the connecting section.

In accordance with yet another aspect of this invention, there is provided a syringe pump unit comprising: a first syringe pump including a first cylinder and a first piston to be inserted in the first cylinder; a second syringe pump including a second cylinder and a second piston to be inserted in the second cylinder; a connecting section for connecting the first piston and the second piston; and a driving source for driving the first and second pistons through the connecting section.

In accordance with still another aspect of this invention, there is provided a sample analyzer comprising: a preparing section for preparing an analysis sample to be analyzed using a sample, a first liquid and a second liquid; and a detector for detecting a signal from the analysis sample, wherein the preparing section comprises a liquid transfer unit, the liquid transfer unit including: a pump connected to a first liquid retaining section for storing the first liquid and a second liquid retaining section for storing the second liquid; a flow path for connecting between the pump and the second liquid retaining section; a third liquid retaining section placed in the flow path; and a liquid discharge section connected to the third liquid retaining section; the pump transporting the second liquid from the second liquid retaining section to the third liquid retaining section and discharging the second liquid with the first liquid via the liquid discharge section to the detector.

In accordance with yet another aspect of this invention, there is provided a liquid transfer unit comprising: a pump connected to a first liquid retaining section for storing a first liquid and a second liquid retaining section for storing a second liquid; a flow path for connecting between the pump and the second liquid retaining section; a third liquid retaining section placed in the flow path; and a liquid discharge section connected to the third liquid retaining section; the pump transporting the second liquid from the second liquid retaining section to the third liquid retaining section and discharging the second liquid with the first liquid via the liquid discharge section.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
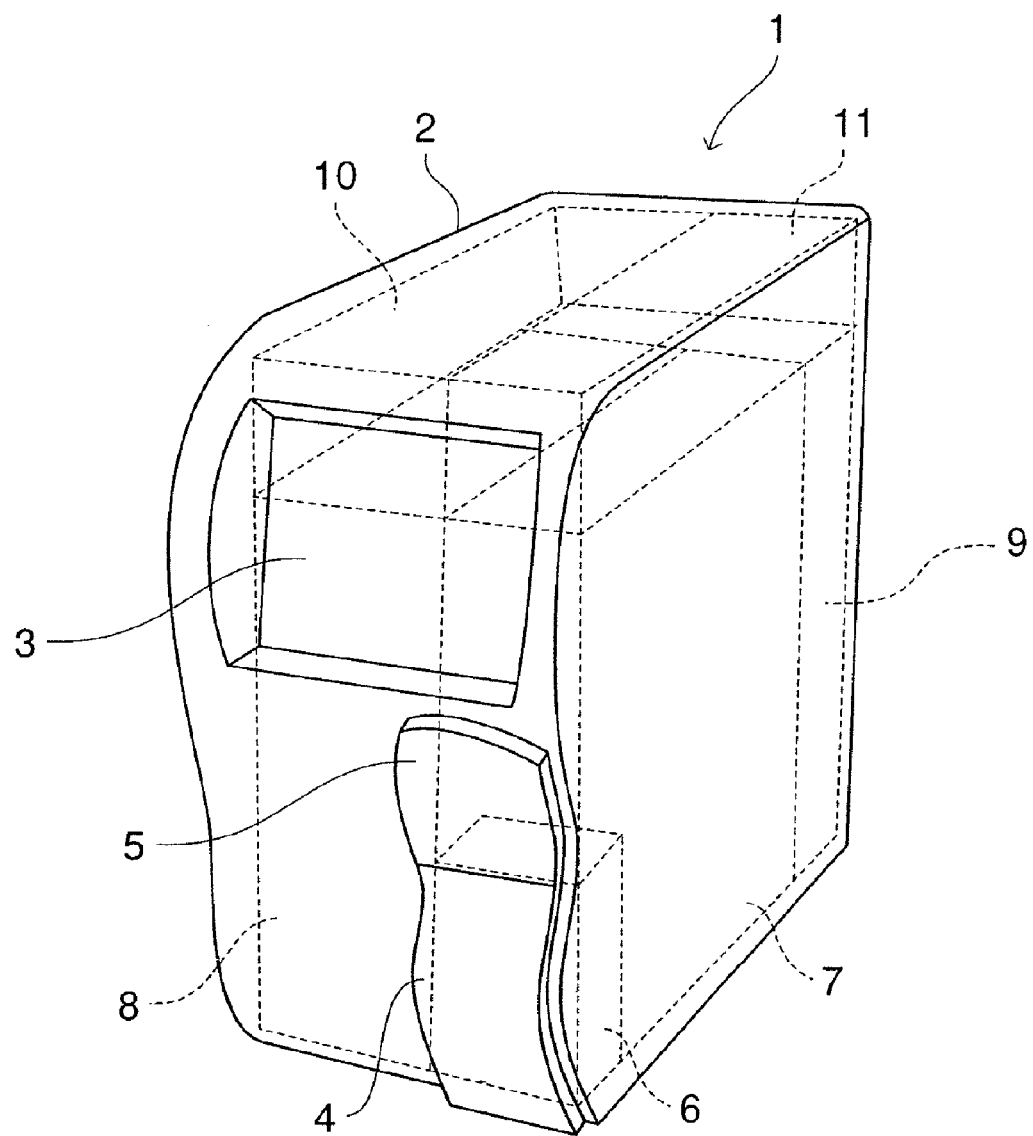
FIG. 1 is a front perspective view of a blood analyzer according to this invention.

A blood analyzer according to one embodiment of this invention will hereinafter be described as one example of a sample analyzer.

The blood analyzer according to this invention is preferably automated. The "automatic" blood analyzer herein means a blood analyzer which permits a user to set at least one sample vessel in the analyzer, and is capable of automatically detecting constituents of a blood sample contained in the sample vessel, calculating values of analysis items, and outputting the results of the calculation.

The blood analyzer is adapted to analyze a blood sample of a mammal such as a human.

Where the blood sample is a human blood sample, exemplary analysis items (measurement/analysis items) include the number of red blood cells (RBC), the number of white blood cells (WBC), the amount of hemoglobin (HGB), the value of hematocrit (HCT), the number of platelets (PLT), a mean corpuscular volume (MCV), a mean corpuscular hemoglobin (MCH), and a mean corpuscular hemoglobin concentration (MCHC).

As for measurement principles, it is preferred to employ a sheath flow electrical resistance method for the measurement of the RBC and the PLT, an electrical resistance method for the measurement of the WBC, and a calorimetric method for the measurement of the HGB. The blood sample to be analyzed is obtained by sampling blood from a subject into a sample vessel (blood sampling tube). The blood sample may be a whole blood sample or a sample preliminarily diluted to a predetermined concentration.

Particularly, where blood is sampled from an infant, the amount of the blood sample is small, so that the blood sample is preliminarily diluted to a predetermined concentration (e.g., 26 times).

Usable as the sample vessel in the blood analyzer are common vacuum blood sampling tubes (sealed with a rubber cap) and common open blood sampling tubes (having an open mouth) each having an outer diameter of 12 to 15 mm and a length of not greater than 85 mm, and control blood vessels each having an outer diameter of about 15 mm and a length of about 20 mm.

The amount of the blood sample required for the analysis is, for example, 10 to 15 μL in the case of the whole blood sample, and 250 to 350 μL in the case of the pre-diluted blood sample.

The blood analyzer comprises a main body and a container housing unit. Preferably, the main body is housed in a housing, and the container housing unit is removably attached to a side wall of the housing. The main body includes a display section provided on a front upper portion of the housing. The display section includes an LCD (liquid crystal display panel) for displaying the results of the analysis. If a touch panel for inputting analysis conditions is provided integrally with the LCD, improvement in the operability of the analyzer as well as space saving can be achieved.

Disposed in the housing are: a sample setting section in which the user sets the sample vessel; a detecting section in which the sample is quantitatively dispensed from the sample vessel and diluted and the blood constituents of the sample are detected; a fluid controlling section including fluid controlling devices for controlling fluids required for quantitatively dispensing and diluting the sample in the detecting section; an electrical control board section which houses electric components for electrically controlling the detecting section, the fluid controlling section and the display section; a power supply section for transforming an AC voltage inputted from a commercial power supply into a lower-level DC voltage; and a printer section for printing out the results of the analysis.

It is preferred to properly lay out these sections in consideration of ease of operation and maintenance and heat generation.

Where the sample setting section is disposed in the vicinity of a front face of the housing and an opening/closing cover (sample setting panel) is provided on the front face of the housing, for example, the user can easily access the sample setting section to set the sample vessel in the sample setting section by opening the cover. Further, the sample vessel thus set is advantageously protected by the cover.

Where the detecting section is provided as a unit inward of a right or left side wall of the housing, for example, the detecting section can easily be accessed for maintenance and inspection by removing one side plate of the housing. The detecting section preferably include a pipette driving device, a mixing chamber, and a detector for quantitatively dispensing the blood sample from the sample vessel by means of a pipette, properly diluting the blood sample and properly analyzing the blood constituents.

The pipette to be herein employed is a pipette generally referred to as "piercer" or "needle" having a sharp tip for piercing the cap of the sample vessel.

Where the fluid controlling section is disposed inward of the other side wall opposite to the detecting section or in back-to-back relation with respect to the detecting section, the fluid controlling section can easily be accessed for maintenance and inspection by removing the other side plate of the housing.

Since electromagnetic valves and pumps provided in the fluid controlling section may cause noises, consideration is given to the silencing of these components for reducing the noises (including sudden noises) of the entire fluid controlling section, for example, to a level not greater than 45 dB. Particularly, a pressure device such as an external compressor is not employed as a driving source for a fluid circuit but, instead, a negative pressure pump is provided in the housing for easy handling of the blood analyzer. The negative pressure pump, which serves as a negative pressure source, is frequently actuated in the blood analyzer, requiring special consideration for the silencing thereof.

The power supply section includes components such as transistors and diodes which generate heat. Therefore, the power supply section is disposed in the uppermost portion of the housing, and ventilators (vent holes) are provided in the housing for spontaneous cooling of the power supply. This arrangement obviates the need for provision of a fan for forcible cooling, and ensures silencing and space saving. With the power supply section disposed in the uppermost portion, the other components are prevented from being adversely affected by the heat generated by the power supply section.

Where the container housing unit is disposed in the side wall of the housing, the sample vessel can easily be replaced and the container housing unit can easily be connected to the analyzer body. The container housing unit is preferably adapted to house at least two containers for containing a diluent and a hemolyzing agent to be used in the analyzer body, and a container for storing a waste liquid to be drained from the analyzer body.

Example

With reference to the attached drawings, this invention will hereinafter be described in detail by way of another embodiment thereof. However, it should be understood that the invention be not limited thereto.

Figure 2:
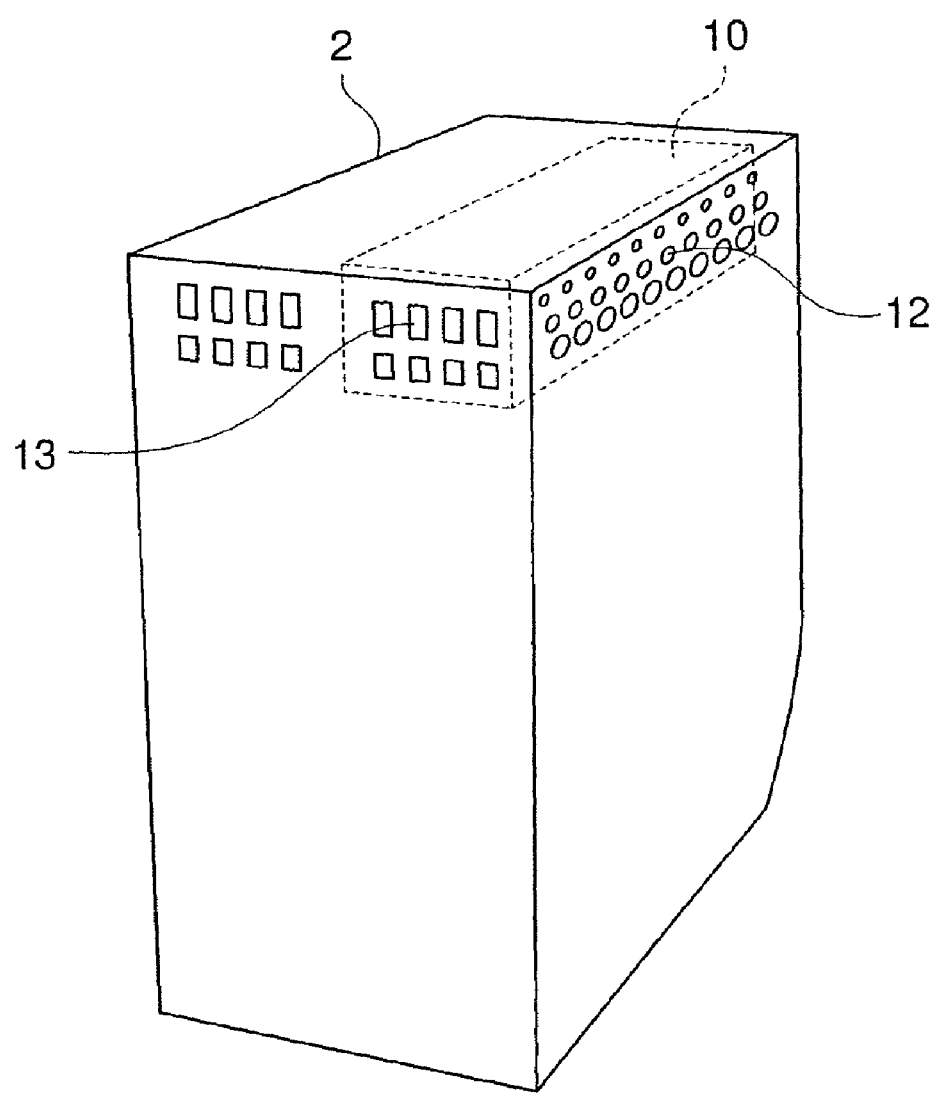
FIG. 2 is a rear perspective view of the blood analyzer according to this invention.

FIGS. 1 and 2 are a front perspective view and a rear perspective view, respectively, of a blood analyzer according to the embodiment of the invention.

As shown, an analyzer body 1 is housed in a housing 2, and includes a display section 3 provided on a front upper portion of the housing 2, a sample setting panel 4 provided on a lower front right portion of the housing 2 and to be opened and closed when a sample vessel is set, and a button 5 to be pressed for opening the sample setting panel 4.

A sample setting section 6 for receiving the sample vessel, and a detecting section 7 for quantitatively dispensing a sample from the sample vessel, diluting the sample and preparing an analysis sample are provided inward of a right side plate of the housing 2.

A fluid controlling section 8 which collectively accommodates fluid devices such as valves and pumps for controlling fluids for the quantitatively dispensing and dilution of the sample in the detecting section 7 is provided inward of a left side plate of the housing 2. An electrical control board section 9 which accommodates a board mounted with electrical control devices for electrically controlling the detecting section 7, the fluid controlling section 8 and the display section 3 is provided inward of a rear side plate of the housing 2.

A power supply section 10 for transforming a commercially available AC voltage supplied thereto into a DC voltage, and a printer section 11 for printing out the results of the analysis are provided inward of a ceiling plate of the housing 2.

The right and left side plates, the rear side plate and the ceiling plate are removably fastened by screws, so that the respective sections are easily accessed for maintenance.

The power supply section 10 which includes a heat generating component is provided in the uppermost position within the housing 2, and ventilators (vent holes) 12, 13 are provided as surrounding the power supply section 10 in the housing 2 as shown in FIG. 2. Therefore, air heated by the power supply section 10 is vented through the ventilators 12, 13 for spontaneous air cooling without thermally affecting the other components of the analyzer. That is, the power supply section 10 does not require forcible air cooling means such as a cooling fan, so that the size reduction and noise reduction of the analyzer can be achieved.

Figure 3:
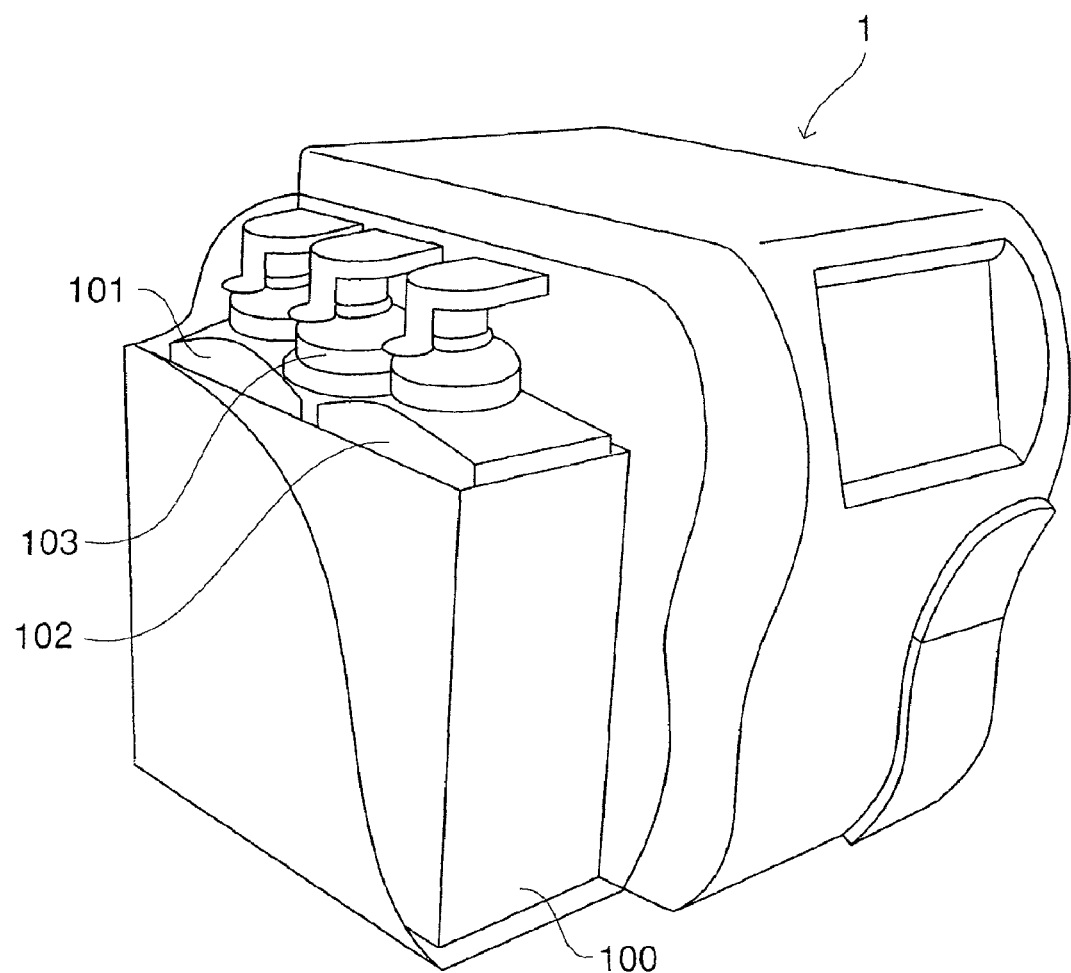
FIG. 3 is a perspective view of a container housing unit attached to the blood analyzer according to this invention.

As shown in FIG. 3, a container housing unit 100 which accommodates containers 101, 103 respectively containing a diluent and a hemolyzing agent and a container 102 for storing waste liquid in combination is attached to a left side face of the analyzer body 1.

Construction and Operation of Sample Setting Section

Figure 4:
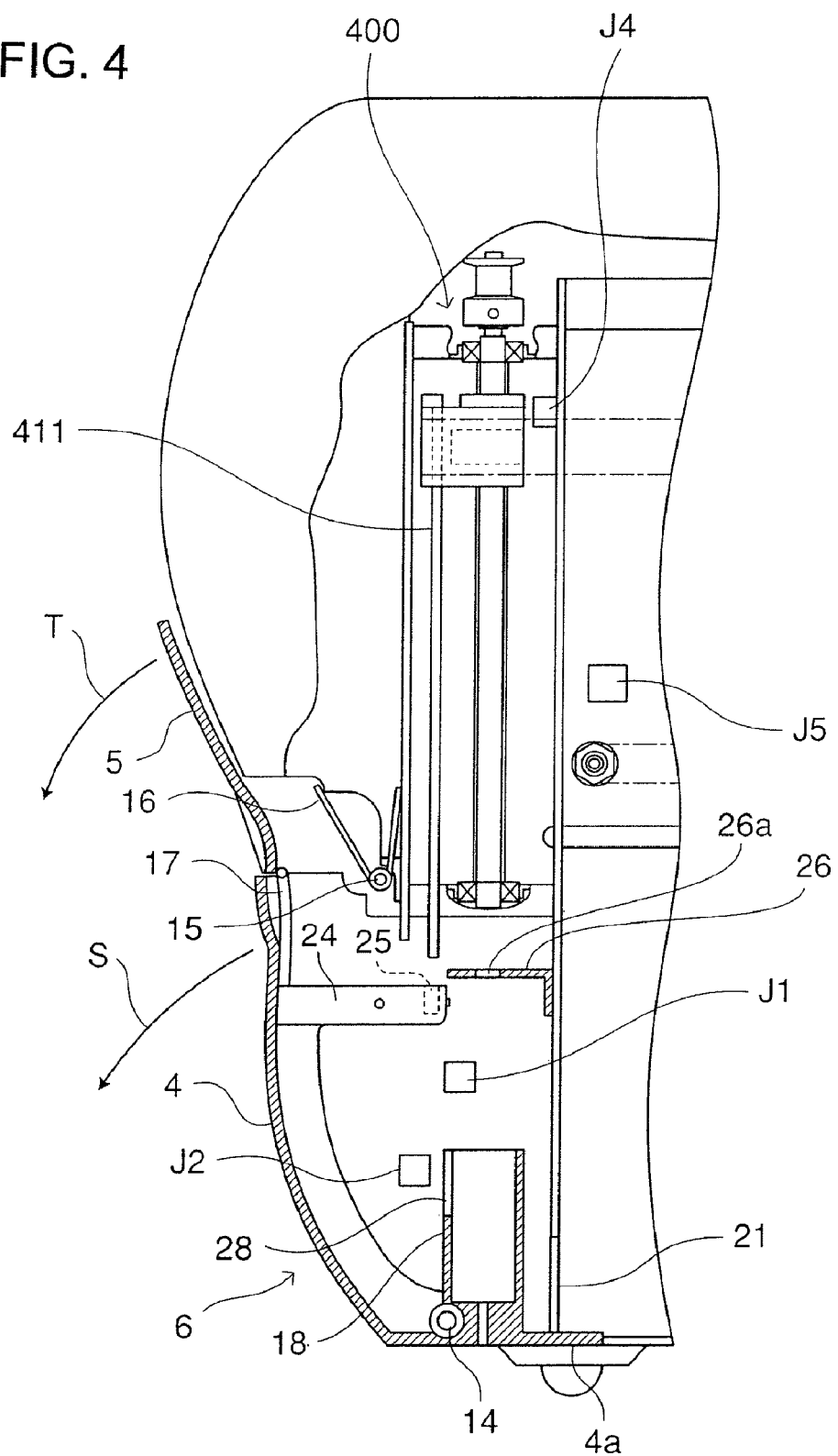
FIG. 4 is a front view of a sample setting section of the blood analyzer according to this invention.

FIG. 4 is a front view illustrating the construction of the sample setting section 6. As shown, the sample setting panel 4 is supported pivotally about a support shaft 14 in an arrow direction S, and biased in the arrow direction S by a spring not shown. Above the sample setting panel 4, the button 5 is supported pivotally about a support shaft 15 and biased in an arrow direction T by a spring 16.

A claw 17 provided on an upper edge of the sample setting panel 4 is engaged with a lower edge of the button 5 to prevent the sample setting panel 4 from opening in the arrow direction S. The sample setting panel 4 is provided with a cylindrical sample rack 18 for housing the sample vessel.

As shown in FIG. 4, an adaptor detecting sensor (photo-interrupter) J1 and an adaptor recognizing sensor (photo-interrupter) J2 to be described later are provided in the sample setting section 6.

Figure 5:
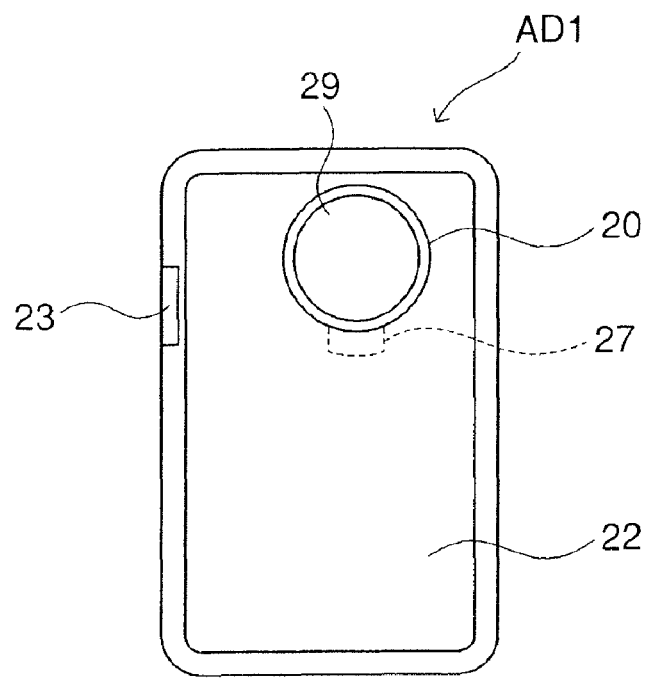
FIG. 5 is a top surface view of an adaptor according to this invention.
Figure 6:
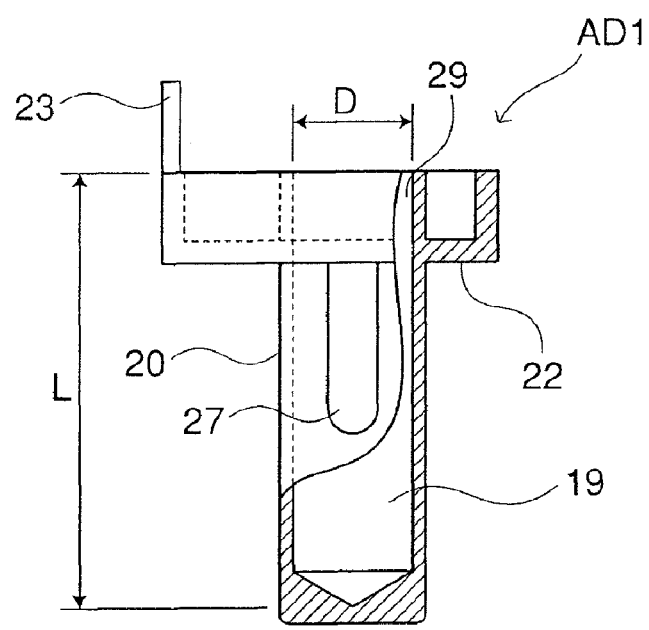
FIG. 6 is a front view of the adaptor according to this invention.
Figure 7:
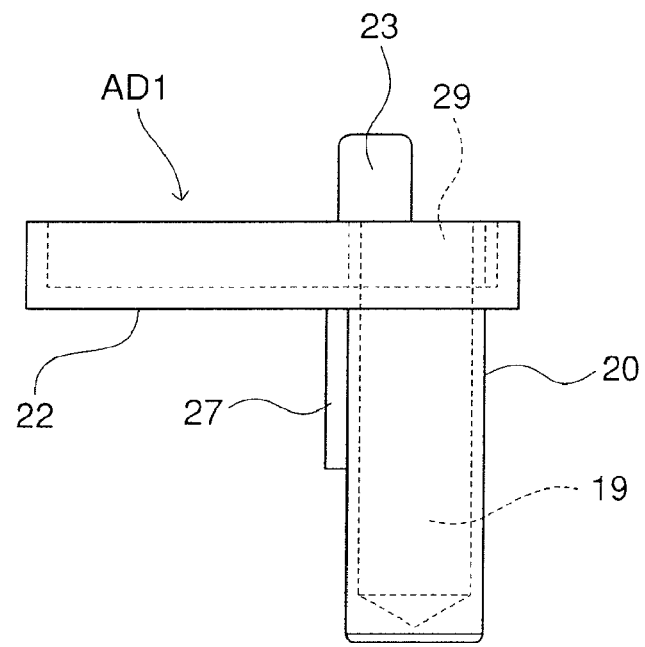
FIG. 7 is a side view of the adaptor according to this invention.

FIGS. 5, 6 and 7 are a top surface view, a front view and a side view, respectively, of an adaptor AD1 to be inserted preliminarily in the sample rack 18 when the sample vessel (blood sampling tube) is set in the sample rack 18. As shown, the adaptor AD1 includes a cylindrical portion 20, which serves as a sample vessel supporting section, having a cylindrical recess 19 to be engaged with a lower part of the sample vessel, and a receiving tray 22 provided around an inlet 29 of the recess 19 for receiving the sample to be spilled from the sample vessel. The receiving tray 22 is provided integrally with the cylindrical portion 20. One adaptor with the recess 19 having a depth of 45 mm and an inner diameter of 16.5 mm, and another adaptor with the recess 19 having a depth of 45 mm and an inner diameter of 13.6 mm are prepared as the adaptor AD1. Therefore, these adaptors can be employed for two types of sample vessels having different outer diameters.

An identity piece 23 projecting upward from the receiving tray 22 is provided in at a portion of the periphery of the receiving tray 22. The identity piece 23 is sensed by the adaptor detecting sensor (photo-interrupter) J1 (FIG. 4) for sensing simultaneously whether the adaptor AD1 is set in the sample rack and whether the sample setting panel 4 is opened and closed.

Figure 8:
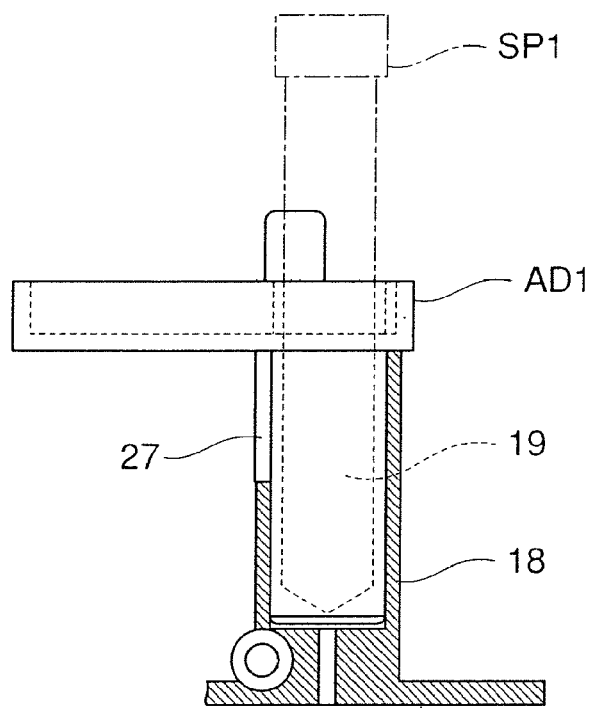
FIG. 8 is a diagram for explaining a state where the adaptor is inserted into a sample rack according to this invention.

An elongated projection 27 projecting downward from a lower surface of the receiving tray 22 is provided on an outer surface of the cylindrical portion 20. When the adaptor AD1 is inserted in the sample rack 18 as shown in FIG. 8, the projection 27 is fitted into a notch 28 (FIG. 4) of the sample rack 18 for positioning the adaptor AD1 with respect to the sample rack 18. Whereby, the orientation of the receiving tray 22 is determined. In the above Example, the projection 27 may be provided in the sample rack 18 and the notch 28 may be provided on the outer surface of the cylindrical portion 20.

After a user sets the adaptor AD1 with the recess 19 corresponding to the size of the sample vessel SP1 in the sample rack 18 as shown in FIG. 8, the user inserts the sample vessel SP1 into the adaptor AD1.

Figure 38:
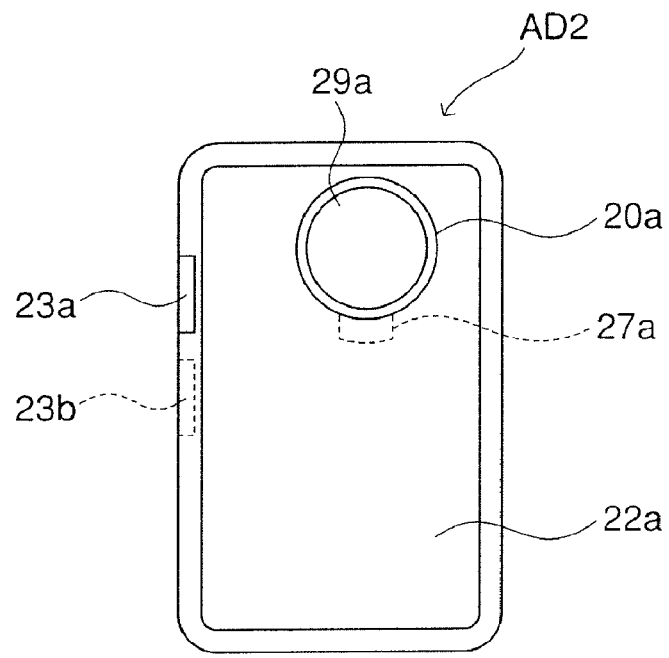
FIG. 38 is a top surface view illustrating another exemplary adaptor employed in the blood analyzer according to this invention.
Figure 39:
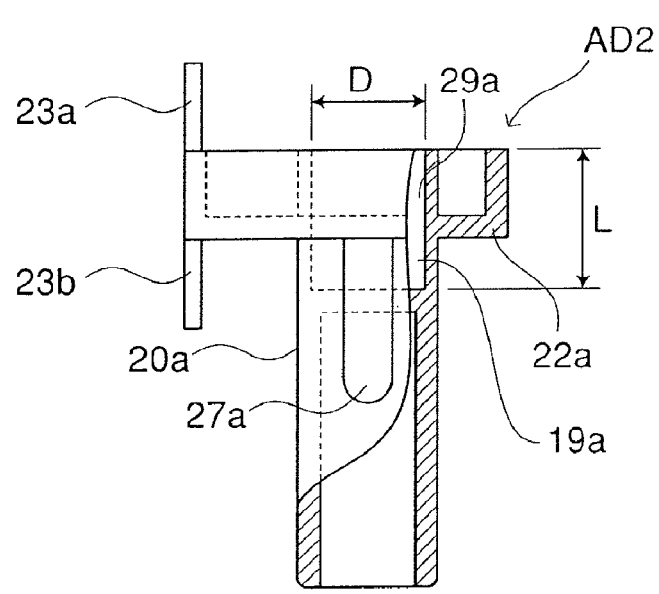
FIG. 39 is a front view of the adaptor shown in FIG. 38.
Figure 40:
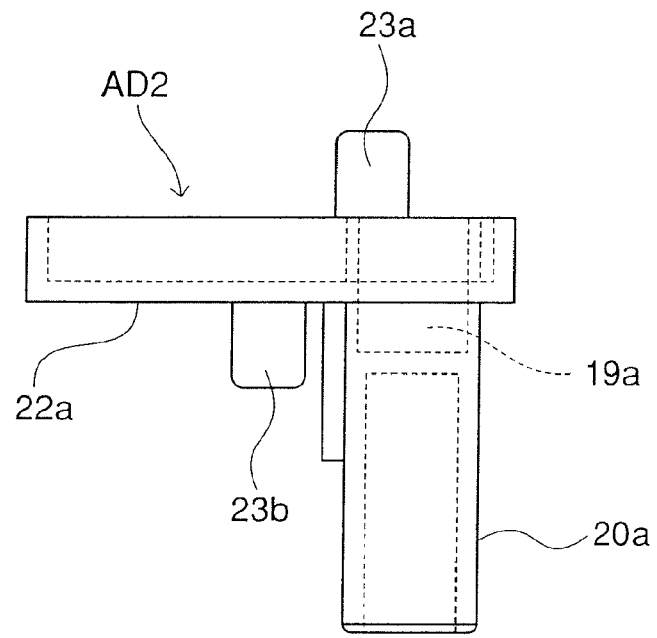
FIG. 40 is a side view of the adaptor shown in FIG. 38.

FIGS. 38, 39 and 40 are a top surface view, a front view and a side view, respectively, of an adaptor AD2 to be inserted preliminarily in the sample rack 18 when a sample vessel containing controlled blood constituents for test (i.e., control blood) is set in the sample rack 18. As shown, the adaptor AD2 includes a cylindrical portion 20a, which serves as a sample vessel supporting section, having a cylindrical recess 19a to be engaged with a lower part of the sample vessel employed for the control blood, and a receiving tray 22a provided around an inlet 29a of the recess 19a for receiving the sample to be spilled from the control blood sample vessel. The receiving tray 22a is provided integrally with the cylindrical portion 20a. One adaptor with the recess 19a having a depth of 15 mm and an inner diameter of 15.6 mm is prepared as the adaptor AD2. Therefore, this adaptor can be employed for the control blood sample vessel.

An identity piece 23a projecting upward from the receiving tray 22a is provided at an upper portion of the periphery of the receiving tray 22a. The identity piece 23a is sensed by the adaptor detecting sensor (photo-interrupter) J1 (FIG. 4) for sensing simultaneously whether the adaptor AD2 is set in the sample rack and whether the sample setting panel 4 is opened and closed.

Figure 41:
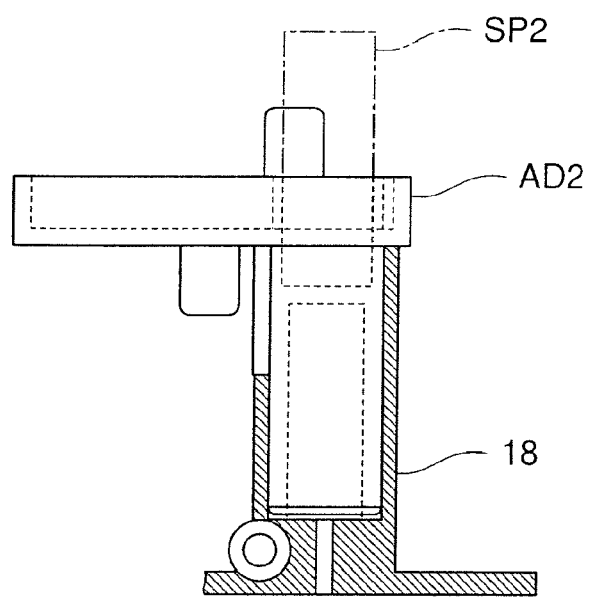
FIG. 41 is a diagram for explaining a state where the adaptor shown in FIG. 38 is inserted into the sample rack according to this invention.

An elongated projection 27a projecting downward from a lower surface of the receiving tray 22a is provided on an outer surface of the cylindrical portion 20a. When the adaptor AD2 is inserted in the sample rack as shown in FIG. 41, the projection 27a is fitted into the notch 28 (FIG. 4) of the sample rack 18 for positioning the adaptor AD2 with respect to the sample rack 18. Whereby, the orientation of the receiving tray 22a is determined.

An identity piece 23b projecting downward from the receiving tray 22a is provided at a lower portion of the periphery of the receiving tray 22a. The identity piece 23b is sensed by an adaptor recognizing sensor (photo-interrupt) J2 (FIG. 4) for recognizing that an adaptor inserted in the sample rack 18 is the adaptor AD2 for the control blood sample vessel SP2.

After the user sets the adaptor AD2 with the recess 19a corresponding to the size of the control blood sample vessel SP2 in the sample rack 18 as shown in FIG. 41, the user inserts the control blood sample vessel SP2 into the adaptor AD2.

Figure 61:
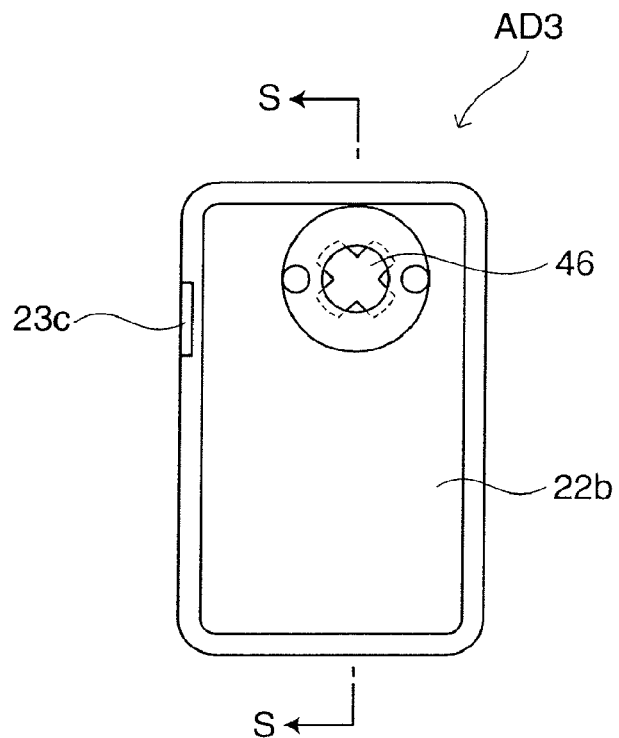
FIG. 61 is a top surface view illustrating further another exemplary adaptor employed in the blood analyzer according to this invention.
Figure 62:
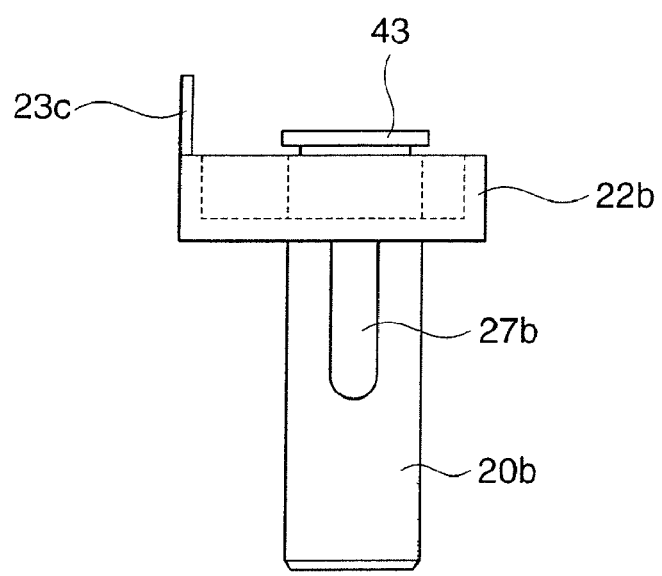
FIG. 62 is a front view of the adaptor shown in FIG. 61.
Figure 63:
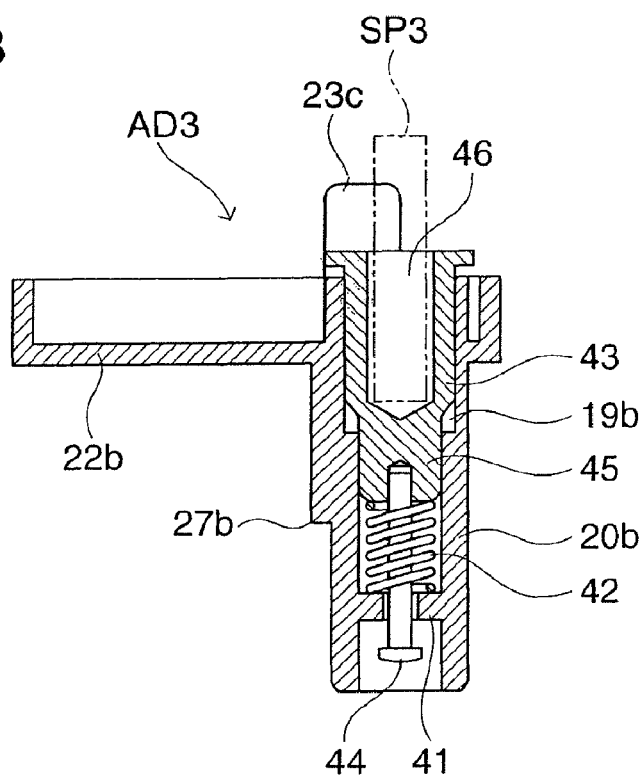
FIG. 63 is a view from an S-S arrow direction in FIG. 61.

FIGS. 61 and 62 are a top surface view and a front view, respectively, of an adaptor AD3 employed for an open sample vessel having a small capacity in order to store a small-volume sample (blood) obtained from infants or small animals. FIG. 63 is a view from an S-S arrow direction in FIG. 61.

The adaptor AD3 is preliminarily inserted in the sample rack 18 when the sample vessel is set in the sample rack 18. The adaptor AD3 supports resiliently the sample vessel thus set. Thus, when the small-volume sample is sucked from the vicinity of a bottom of the sample vessel by means of a pipette to be described later, the pipette and the sample vessel are prevented from being damaged even if a tip of the pipette is brought into contact with the bottom of the sample vessel.

As shown, the adaptor AD3 includes a cylindrical portion 20b, and a receiving tray 22b provided around an upper opening of the cylindrical portion 20b for receiving the sample to be spilled from the sample vessel. The receiving tray 22b is provided integrally with the cylindrical portion 20b.

As shown in FIG. 63, the cylindrical portion 20b has a cylindrical recess 19b extending therein. A compression spring 42 serving as a first resilient member is inserted into a bottom 41 of the recess 19b, and a sample vessel inserting portion 43 with a recess 46 for the sample vessel is mounted on the spring 42 for receiving a sample vessel SP3. A bottom 45 of the sample vessel inserting portion 43 and the compression spring 42 are connected to each other by means of a pin 44 piercing through the bottom 41, whereby the sample vessel inserting portion 43 is supported in the recess 19b in a vertically slidable manner. That is, when the sample vessel inserting portion 43 is pressed downward, the inserting portion 43 can be moved downward by the pressure (i.e. while working against the resilience of the compression spring 42). The sample vessel supporting section is comprised of the cylindrical portion 20b, the compression spring 42, the sample vessel inserting portion 43 and the pin 44.

Figure 64:
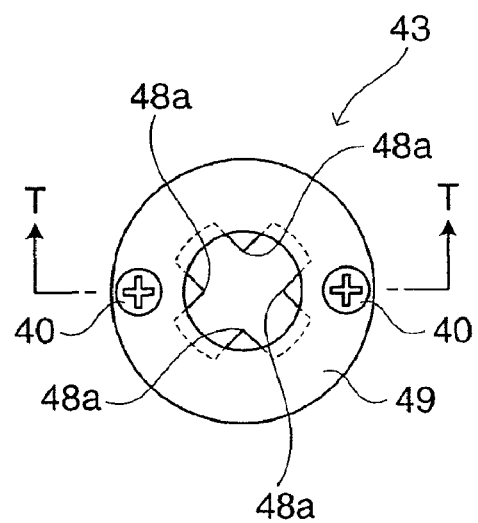
FIG. 64 is a top surface view of a major portion of the adaptor shown in FIG. 61.
Figure 65:
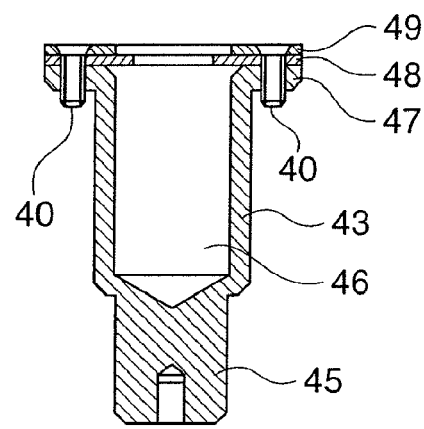
FIG. 65 is a view from a T-T arrow direction in FIG. 64.

FIG. 64 is a top surface view of the sample vessel inserting section 43, and FIG. 65 is a view from a T-T arrow direction in FIG. 64. As shown, a flange 47 is provided at a periphery of an upper opening of the recess 46 in the sample vessel inserting section 43. A second resilient member 48 for positioning the sample vessel SP3 coaxially with the recess 46 is pressed by a ring-shaped holding board 49, and fastened by two screws 40. The second resilient member 48 is composed of a ring-shaped silicone rubber board and provided with four projection pieces 48a projecting toward the center of the opening.

A lower end portion of the recess 46 is conical in shape. When the sample vessel SP3 is inserted into the recess 46, the sample vessel is pressed toward the center of the recess 46 by the resilience of the projection pieces 48a, and the recess 46 with the cone-shaped lower end portion allows the sample vessel SP3 to be guided toward the center of the recess. Thus, the sample vessel SP3 to be inserted into the recess 46 is constantly positioned along the axis of the recess 46.

In the adaptor AD3, the sample vessel SP3 having an outer diameter of 7.5 to 11 mm can be accommodated into the recess 46 having a depth of 21 mm. An identity piece 23c projecting upward from the receiving tray 22b is provided at a portion of the periphery of the receiving tray 22b. The identity piece 23c is sensed by the adaptor detecting sensor (photo-interrupter) J1 (FIG. 4) for sensing simultaneously whether the adaptor AD3 is set in the sample rack and whether the sample setting panel 4 is opened and closed.

Figure 66:
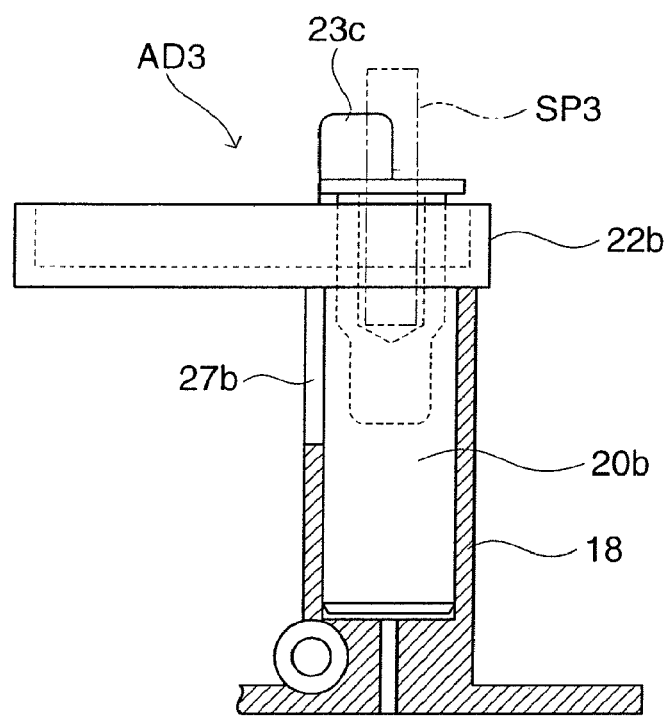
FIG. 66 is a diagram for explaining a state where the adaptor shown in FIG. 61 is inserted into the sample rack.

An elongated projection 27b projecting downward from a lower surface of the receiving tray 22b is provided on an outer surface of the cylindrical portion 20b. When the adaptor AD3 is inserted in the sample rack 18 as shown in FIG. 66, the projection 27b is fitted into the notch 28 (FIG. 4) of the sample rack 18 for positioning the adaptor AD3 with respect to the sample rack 18. Whereby, the orientation of the receiving tray 22b is determined.

Figure 67:
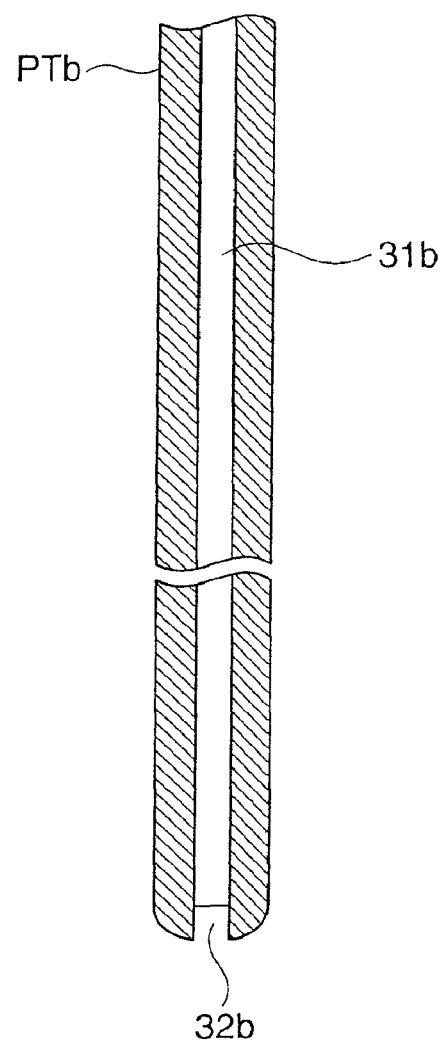
FIG. 67 is a sectional view of a pipette according to another embodiment of this invention.
Figure 68:
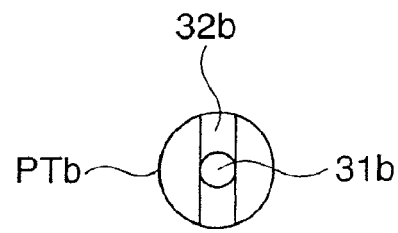
FIG. 68 is a plan view of a major portion of the pipette shown in FIG. 67.

A pipette PTb with a flat tip as shown in FIGS. 67 and 68 is suitably employed to suck the small-volume sample from the bottom of the sample vessel SP3 when the adaptor AD3 is used. The pipette PTb will be described later.

The adaptor AD1 having an inner diameter of 16.5 nun is molded by a transparent ABS resin, the adaptor AD1 having an inner diameter of 13.6 mm is molded by a red ABS resin, the adaptor AD2 is molded by a black ABS resin, and the adaptor AD3 is molded by a blue ABS resin. Thus, the adaptors AD1, AD2 and AD3 are discriminated by color, so that the user can select the type of the adaptors AD1, AD2 and AD3 and the size of the sample vessels to be used. Also, different labels may be attached to the respective adaptors for the discrimination. In order to position the adaptors, a projection may be provided in the sample rack 18 and notches (recesses) may be provided in the respective adaptors.

Figure 9:
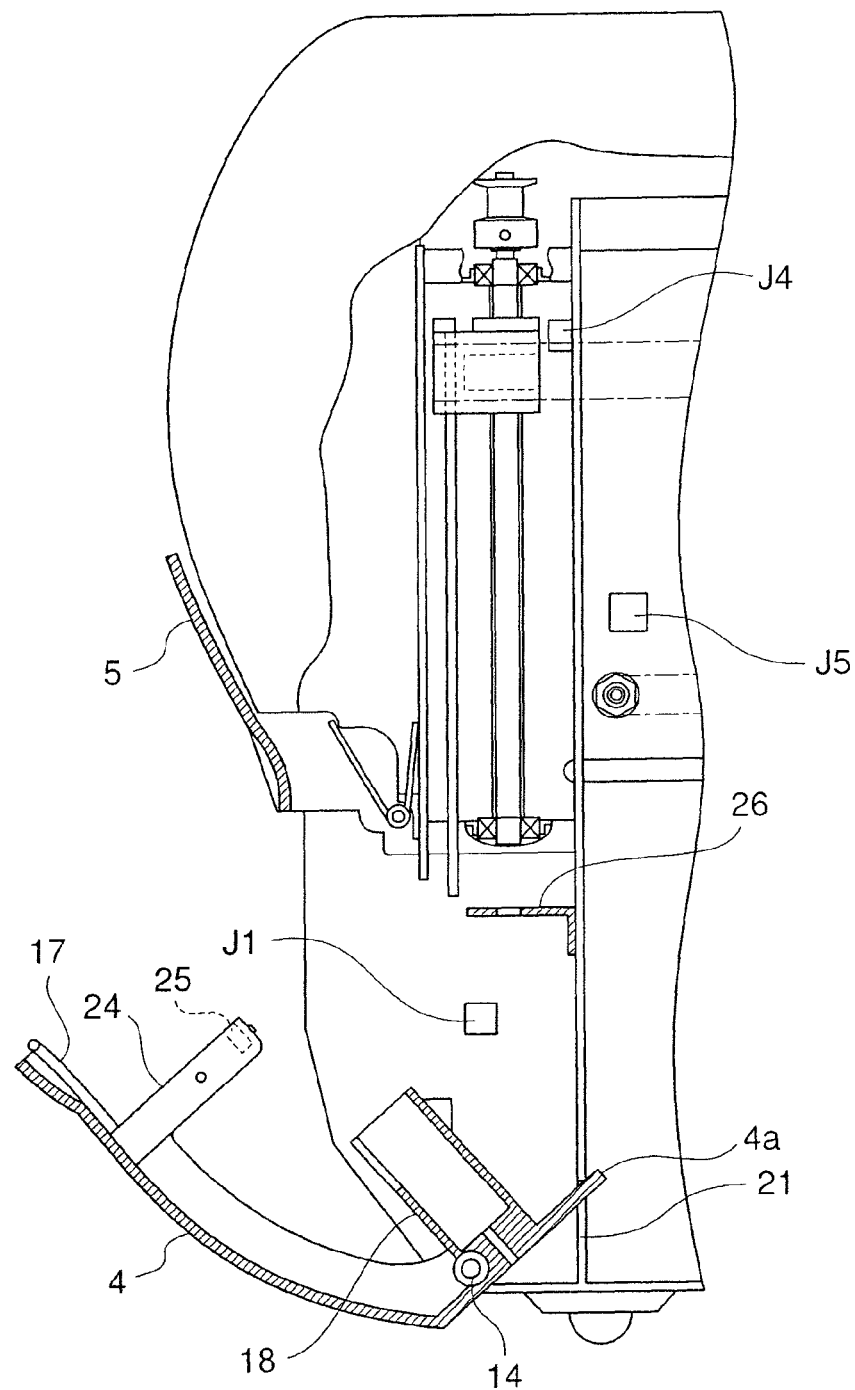
FIG. 9 is a diagram for explaining the operation of the sample setting section of the blood analyzer according to this invention.
Figure 10:
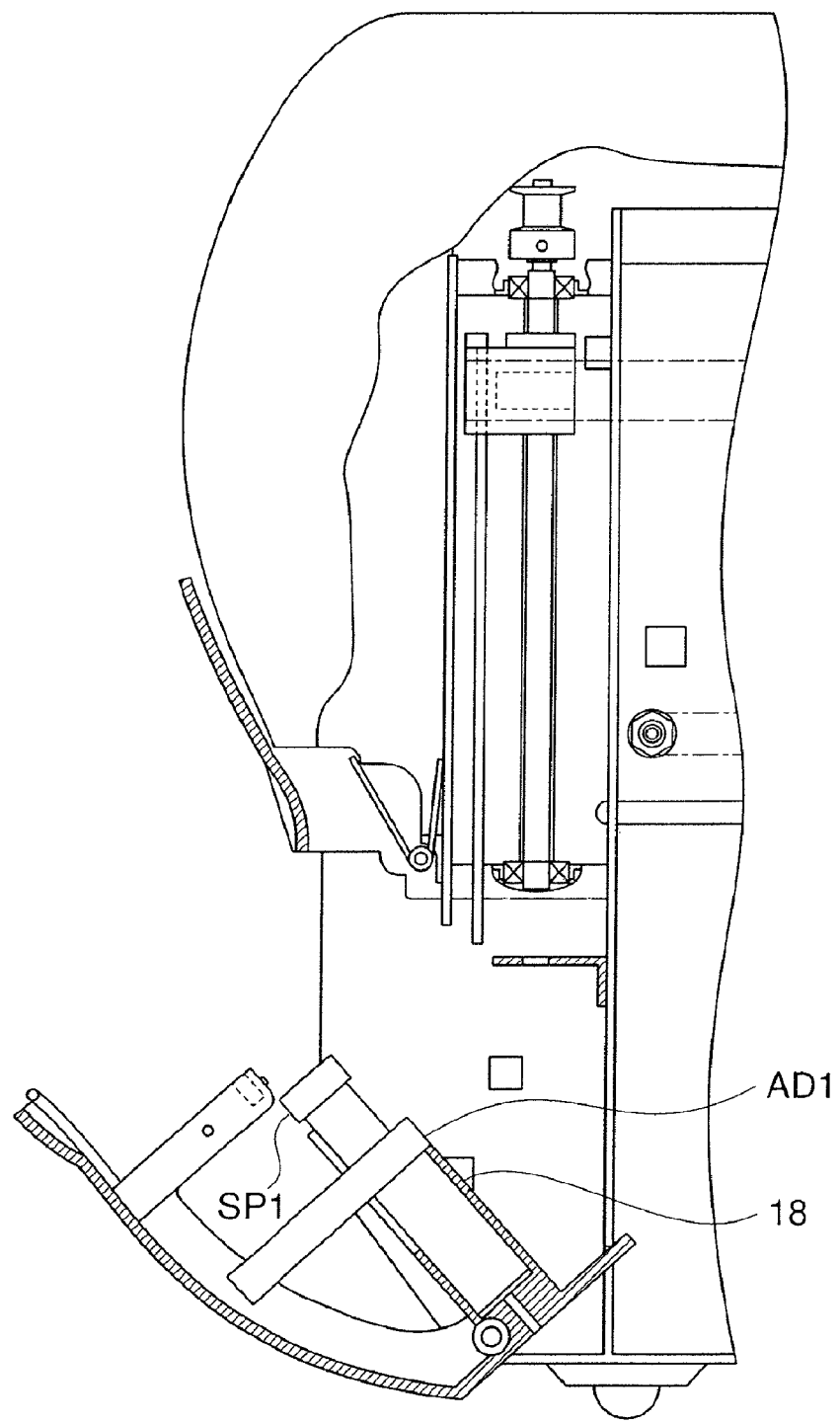
FIG. 10 is a diagram for explaining the operation of the sample setting section of the blood analyzer according to this invention.

In this arrangement, the button 5 is slightly pivoted in a direction opposite to the arrow direction T in FIG. 4 and the lower edge of the button 5 is disengaged from the claw 17, when a user presses an upper end portion of the button 5. Thus, the sample setting panel 4 is pivoted about the support shaft 14 in the arrow direction S thereby to be opened until a projection piece 4a of the sample setting panel 4 is brought into abutment against the support plate 21 as shown in FIG. 9. In this state, the user inserts the sample vessel SP1, SP2 or SP3 into the sample rack 18 with the intervention of the adaptor AD1, AD2 or AD3 as shown in FIG. 10.

Figure 11:
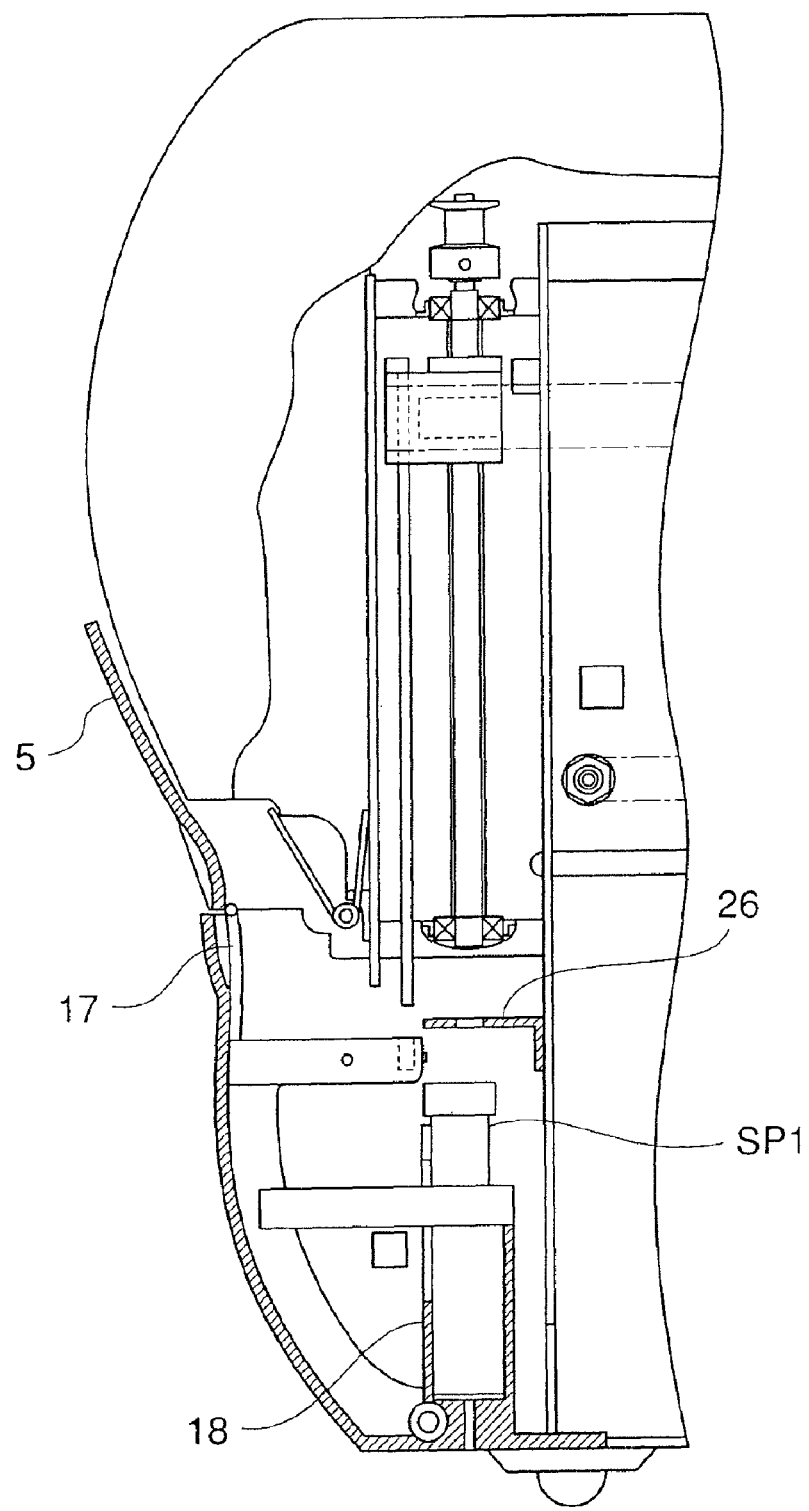
FIG. 11 is a diagram for explaining the operation of the sample setting section of the blood analyzer according to this invention.

When the sample setting panel 4 is thereafter closed as shown in FIG. 11, the sample vessel SP1 (or SP2, SP3) is held coaxially with the sample rack 18. The button 5 has a relatively large surface area (60 mm×70 mm). Therefore, the user can operate the button 5 while holding the sample vessel.

Construction and Operation of Detecting Section

Figure 12:
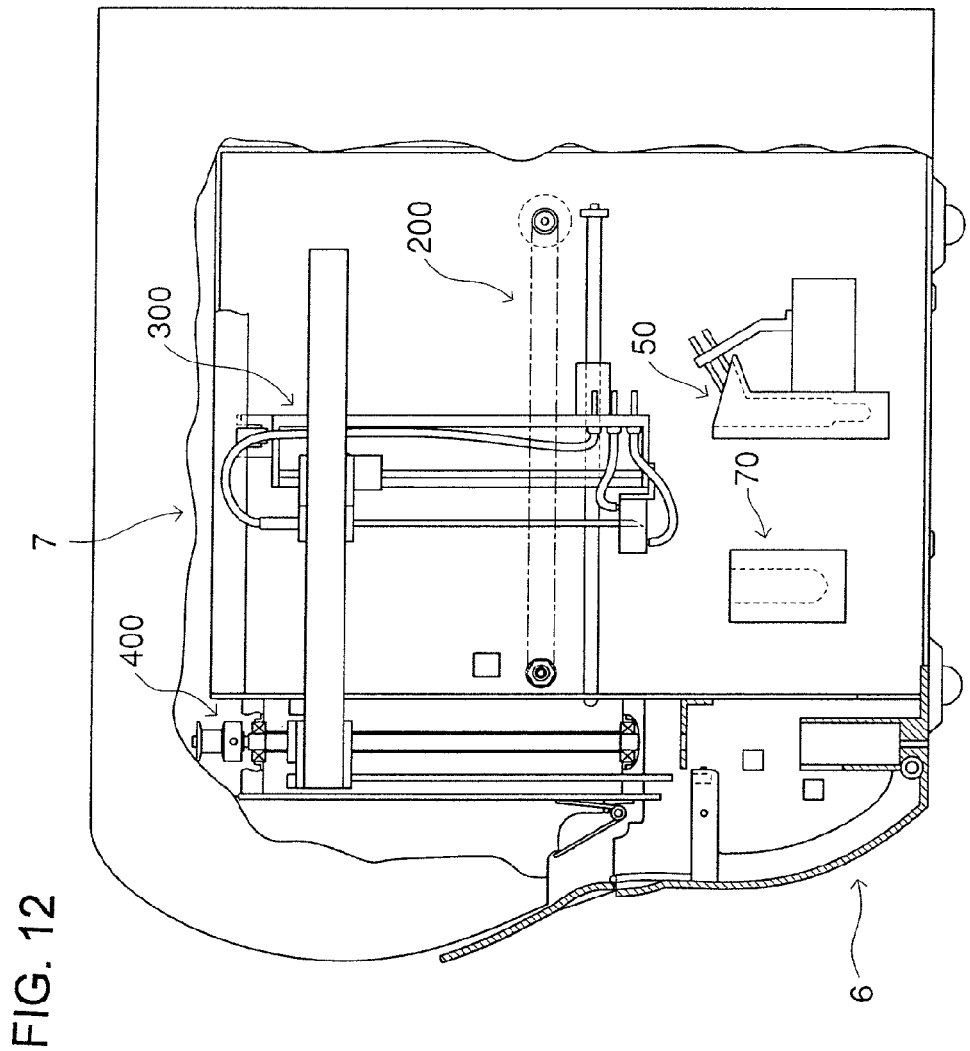
FIG. 12 is a front view of a detecting section of the blood analyzer according to this invention.

As shown in FIG. 12, the detecting section 7 includes a pipette horizontally driving section 200, a pipette vertically sliding section 300, a pipette vertically driving section 400, a mixing chamber 70 and a detector 50.

Pipette Horizontally Driving Section

Figure 13:
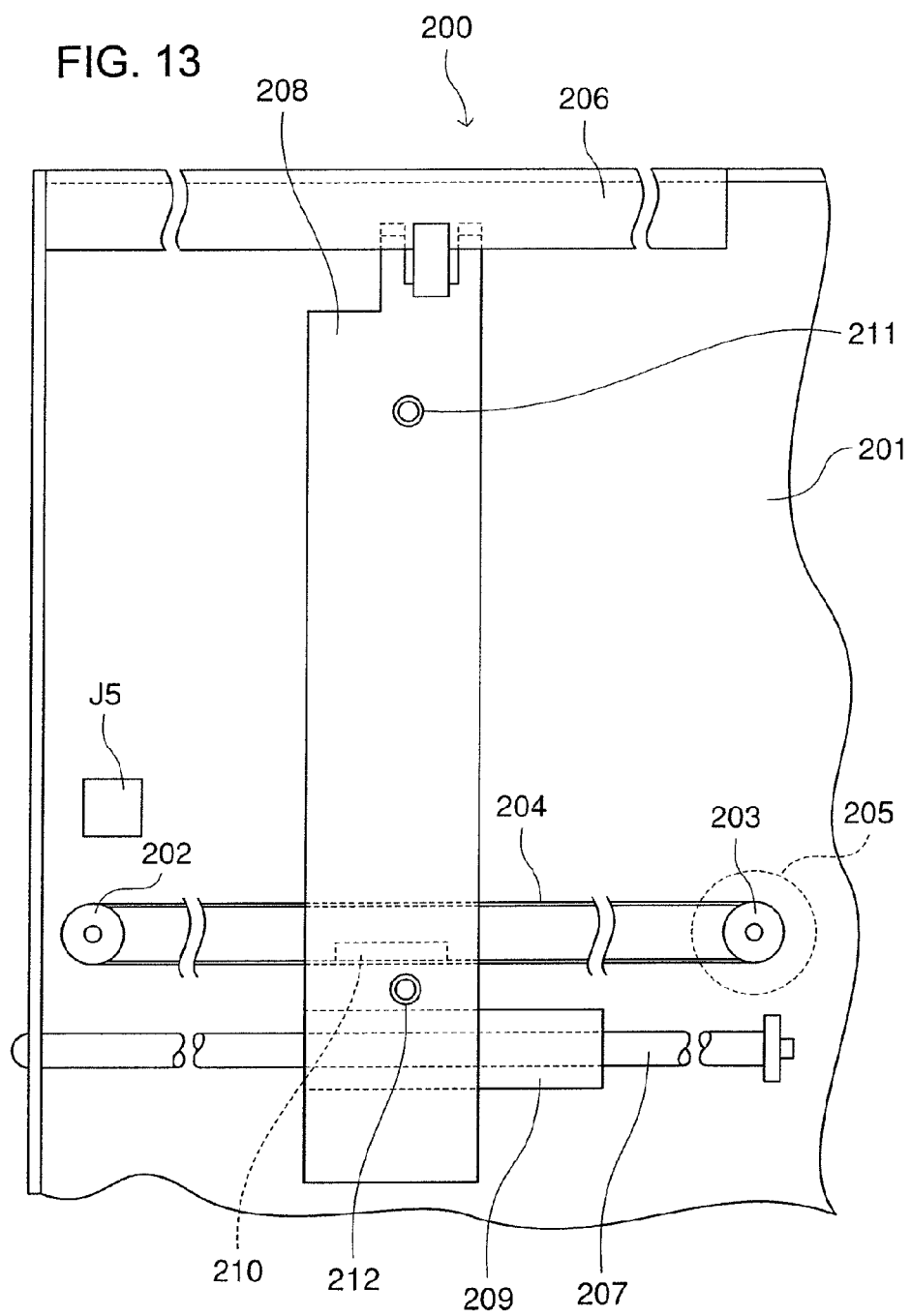
FIG. 13 is a front view of a pipette horizontally driving section of the blood analyzer according to this invention.

FIG. 13 is a front view of the pipette horizontally driving section 200.

As shown, a driven pulley 202 and a driving pulley 203 are rotatably provided on a support plate 201, and a timing belt 204 is stretched between the pulleys 202 and 203. The driving pulley 203 is driven by a pipette back and forth motor (stepping motor) 205 provided on the rear side of the support plate 201.

A guide rail 206 is provided horizontally on an upper portion of the support plate 201, and a guide shaft 207 is provided horizontally on a lower portion of the support plate 201. A vertically elongated horizontal movement plate 208 has an upper edge fitted on the guide rail 206, a lower edge engaged with a sliding member 209 slidable along the guide shaft 207, and a coupling member 210 projecting from the rear side thereof to be coupled with the timing belt 204. The horizontal movement plate 208 has screw holes 211, 212 for fixing the pipette vertically sliding member 300.

With this arrangement, the horizontal movement plate 208 is horizontally movable by the driving of the motor 205. A pipette front position sensor (photo-interrupter) J5 for detecting the position of the horizontal movement plate 208 is provided on the support plate 201.

Pipette Vertically Sliding Section

Figure 14:
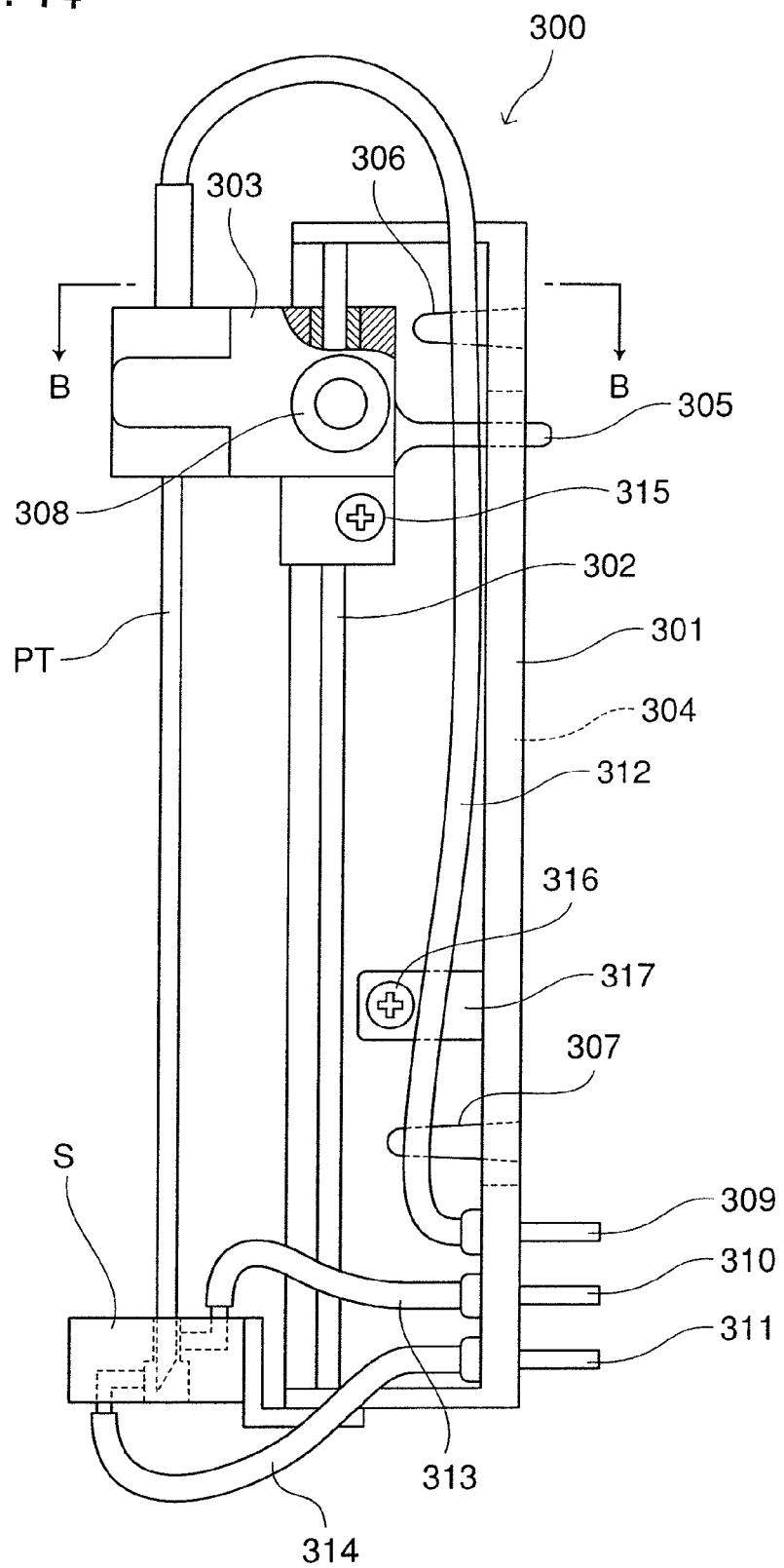
FIG. 14 is a front view of a pipette vertically sliding section of the blood analyzer according to this invention.
Figure 15:
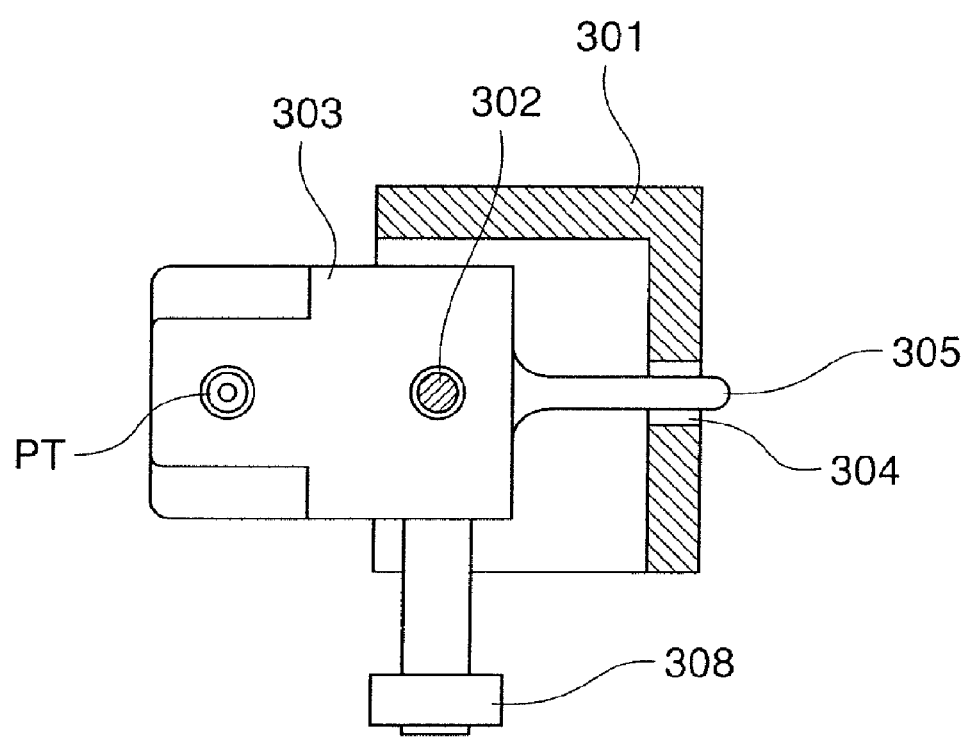
FIG. 15 is a view from a B-B arrow direction in FIG. 14.

FIG. 14 is a front view of the pipette vertically sliding section 300, and FIG. 15 is a view from a B-B arrow direction in FIG. 14. As shown, the pipette vertically sliding section 300 includes a guide shaft 302 vertically supported by a support member 301, and a pipette holder 303 slidable on the guide shaft 302 with a pipette PT vertically held therein.

The support member 301 includes a longitudinally elongated guide groove 304. A guide rod 305 horizontally projecting from the pipette holder 303 is inserted in the guide groove 304 so as to be guided by the guide groove 304, whereby the pipette holder 303 can stably be slid vertically on the guide shaft 302. The support member 301 has notches 306, 307 through which the screws extend for fixing the support member 301 to the horizontal movement plate 208 shown in FIG. 13.

Further, the pipette holder 303 has a guide roller 308, which is engaged with a guide arm (to be described later) of the pipette vertically driving section 400 to cooperate with the guide arm for moving the pipette holder 303 vertically up and down.

A cleaner (pipette cleaning device) S in which the pipette PT is inserted for cleaning the exterior and interior of the pipette PT is provided on a lower portion of the support member 301. When the pipette holder 303 is located at the uppermost position of the support member 301 (in a position shown in FIG. 14), a sharp distal tip of the pipette PT is inserted in the cleaner S.

Liquid supply/drain nipples 309, 310 and 311 fixed to a lower portion of the support member 301 are connected to a proximal end of the pipette PT and ports of the cleaner S via tubes 312, 313 and 314, respectively.

Figure 16:
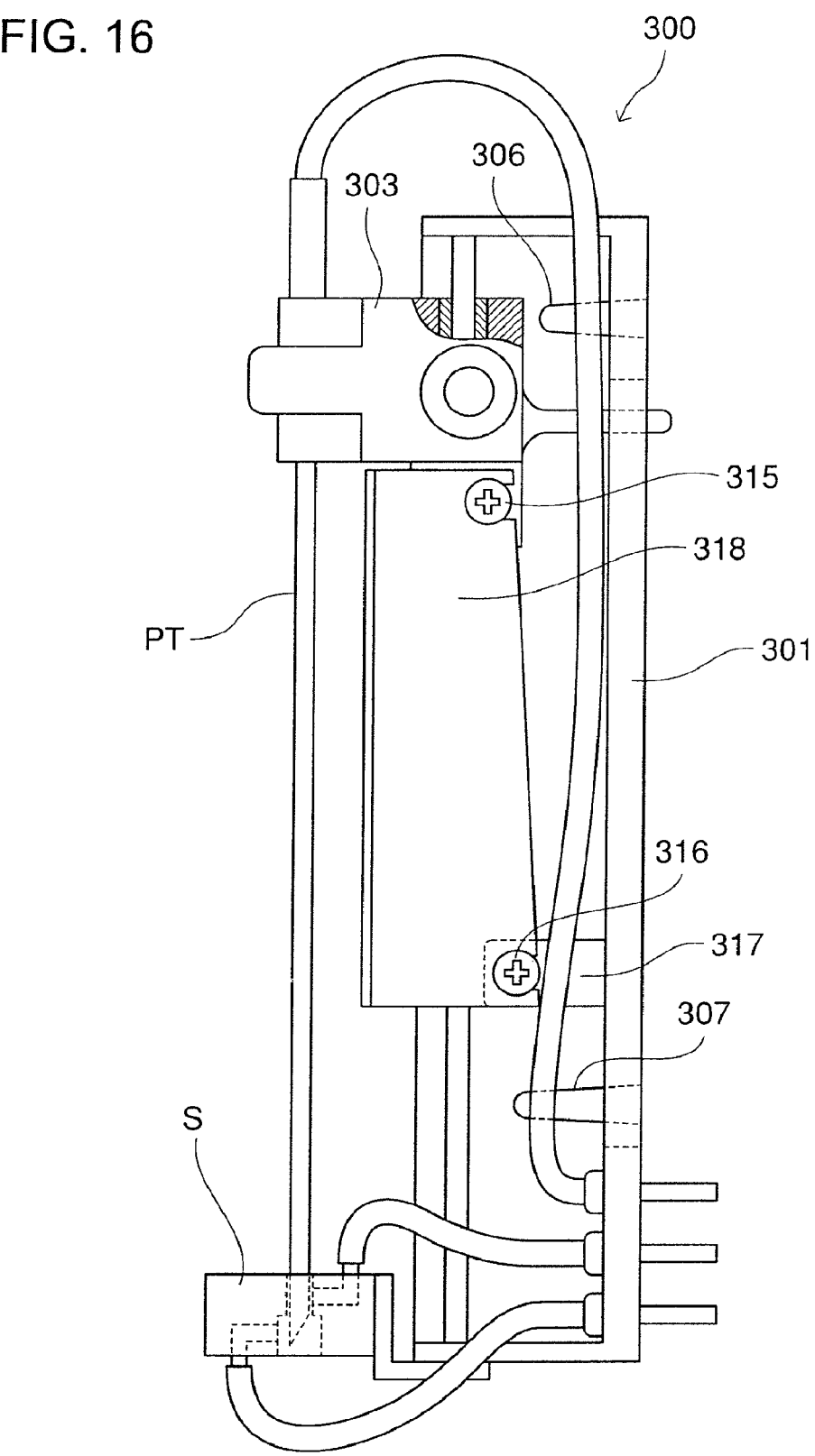
FIG. 16 is a front view of the pipette vertically sliding section of the blood analyzer according to this invention.

A screw 315 fixed to the pipette holder 303 and a screw 316 fixed to a projection 317 of the support member 301 are provided for fixing a spacer plate 318 as shown in FIG. 16.

The spacer 318 fixed as shown in FIG. 16 fixes the pipette holder 303 in the uppermost position of the support member 301 for preventing the sharp tip of the pipette PT from being withdrawn from the cleaner S.

The pipette vertically sliding section 300 is first rested on the horizontal movement plate 208 shown in FIG. 13 with the spacer 318 fixed thereto and, after screws 319, 320 (FIG. 17) are screwed into the screw holes 211, 212 through the notches 306, 307, the spacer 318 is removed by unscrewing the screws 315, 316. Thus, the pipette vertically sliding section 300 can safely be mounted on the pipette horizontally driving section 200 with no possibility that the user is injured by the tip of the pipette PT. Where a trouble such as clogging occurs in the pipette PT, the pipette vertically sliding section 300 is entirely replaced. At this time, the spacer 318 is employed to safely perform a replacing operation.

Figure 17:
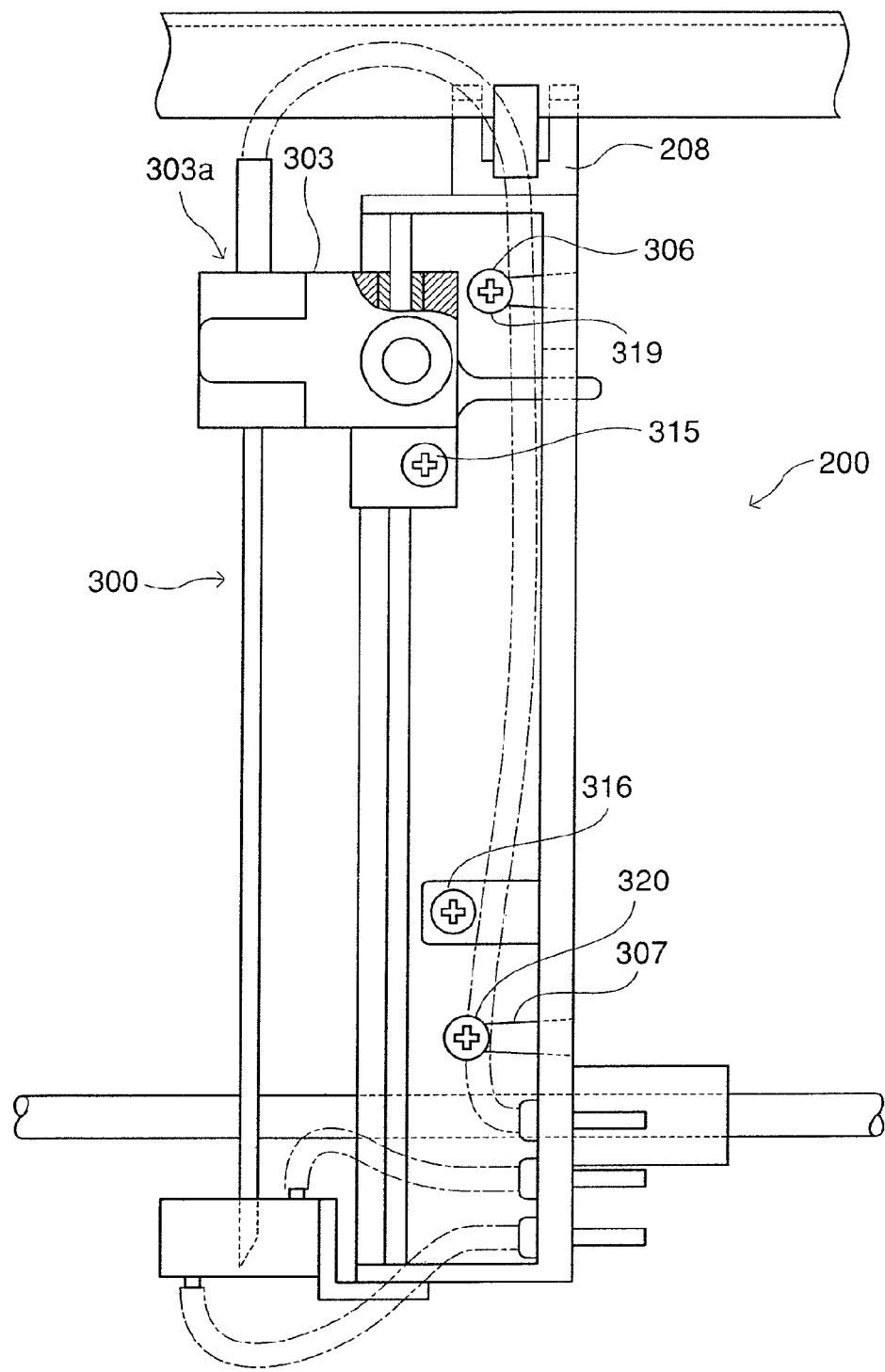
FIG. 17 is a front view of major portions of the pipette vertically sliding section and the pipette horizontally driving section according to this invention.
Figure 18:
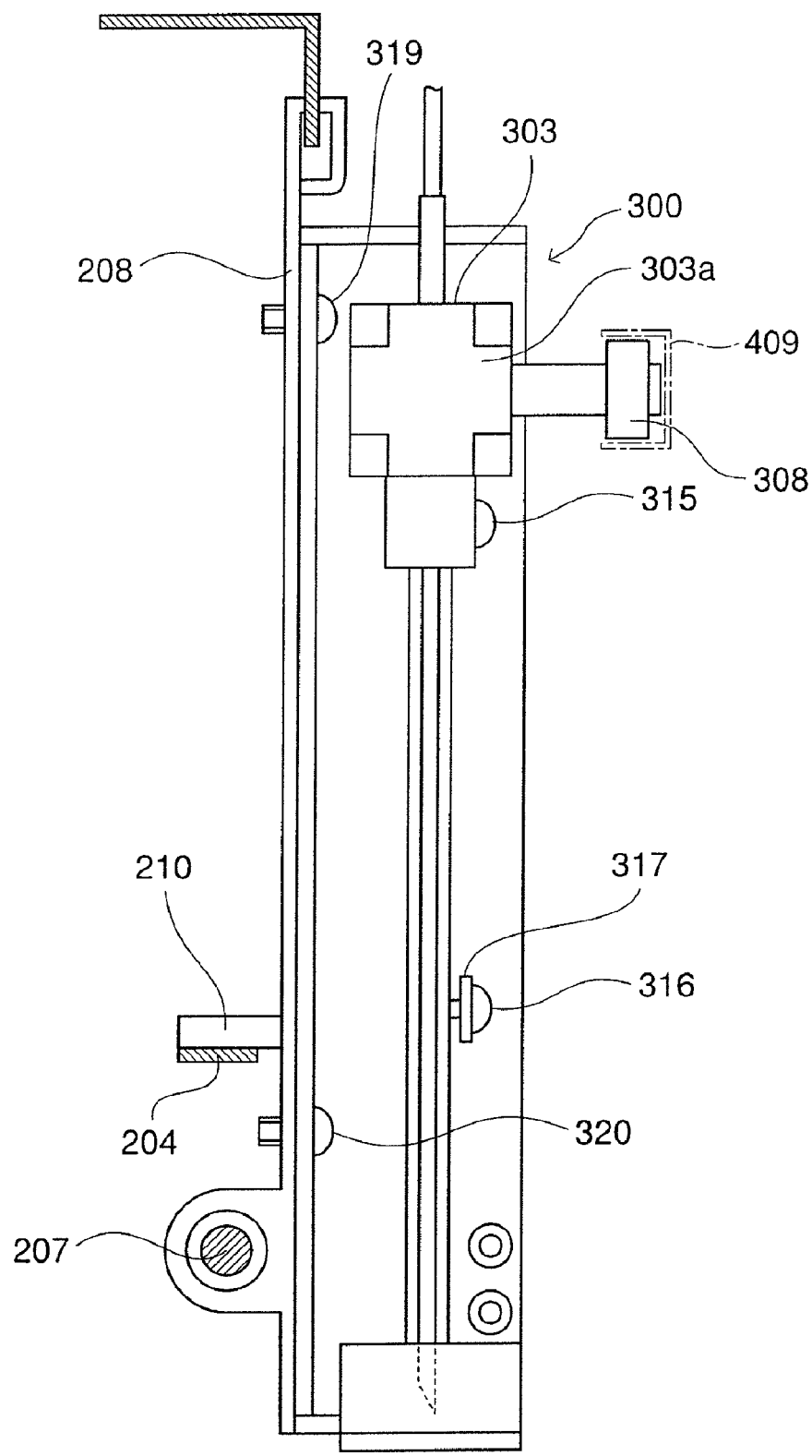
FIG. 18 is a left side view of major portions of the pipette vertically sliding section and the pipette horizontally driving section according to this invention.

FIGS. 17 and 18 are a front view and a left side view, respectively, illustrating a state where the pipette vertically sliding section 300 is mounted on the pipette horizontally driving section 200. As shown, an end 303a of the pipette holder 303 of the pipette vertically sliding section 300 has a cross shape in section so as to be inserted in a main arm (to be described later) of the pipette vertically driving section 400.

Pipette Vertically Driving Section

Figure 19:
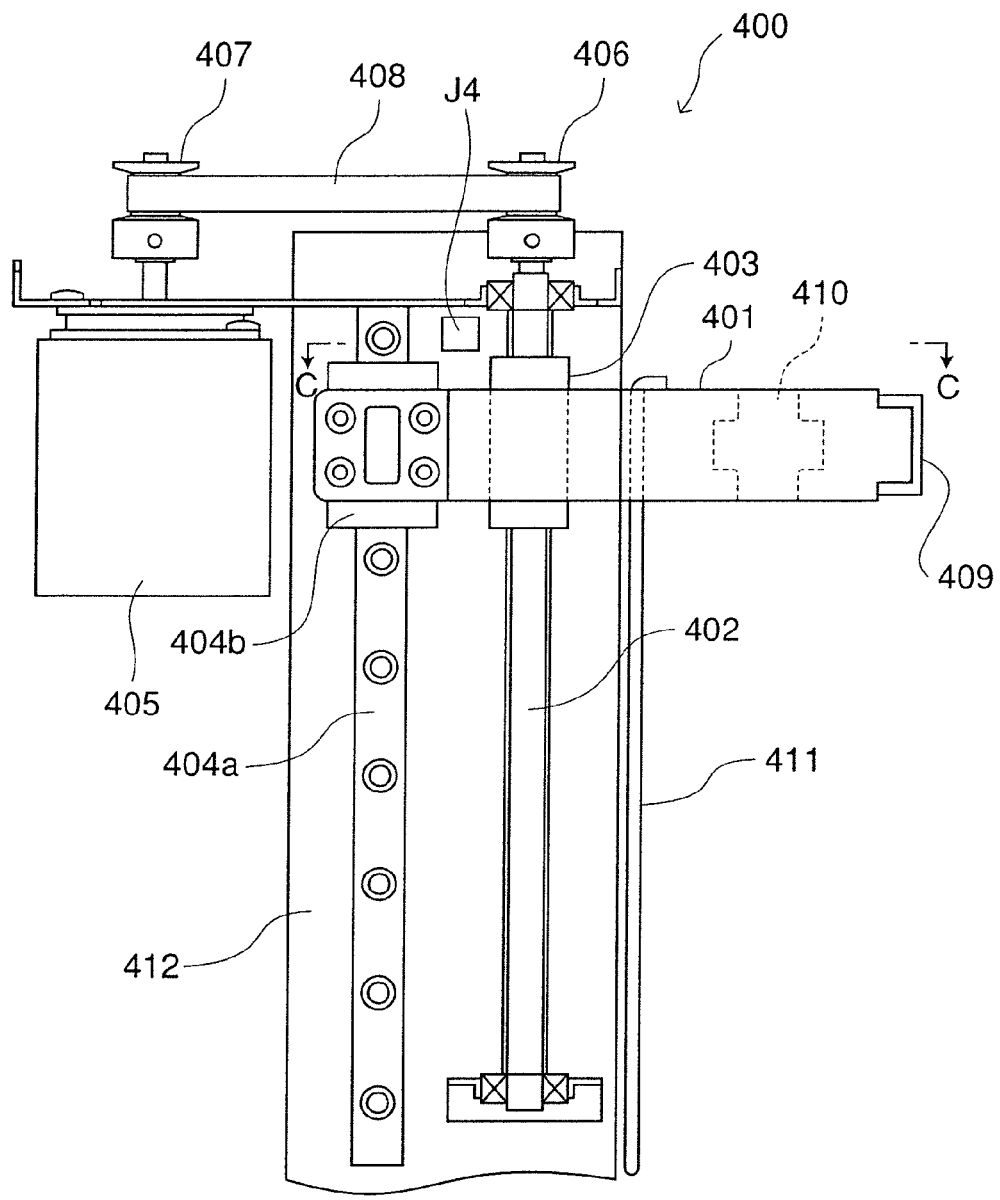
FIG. 19 is a left side view of a pipette vertically driving section according to this invention.
Figure 20:
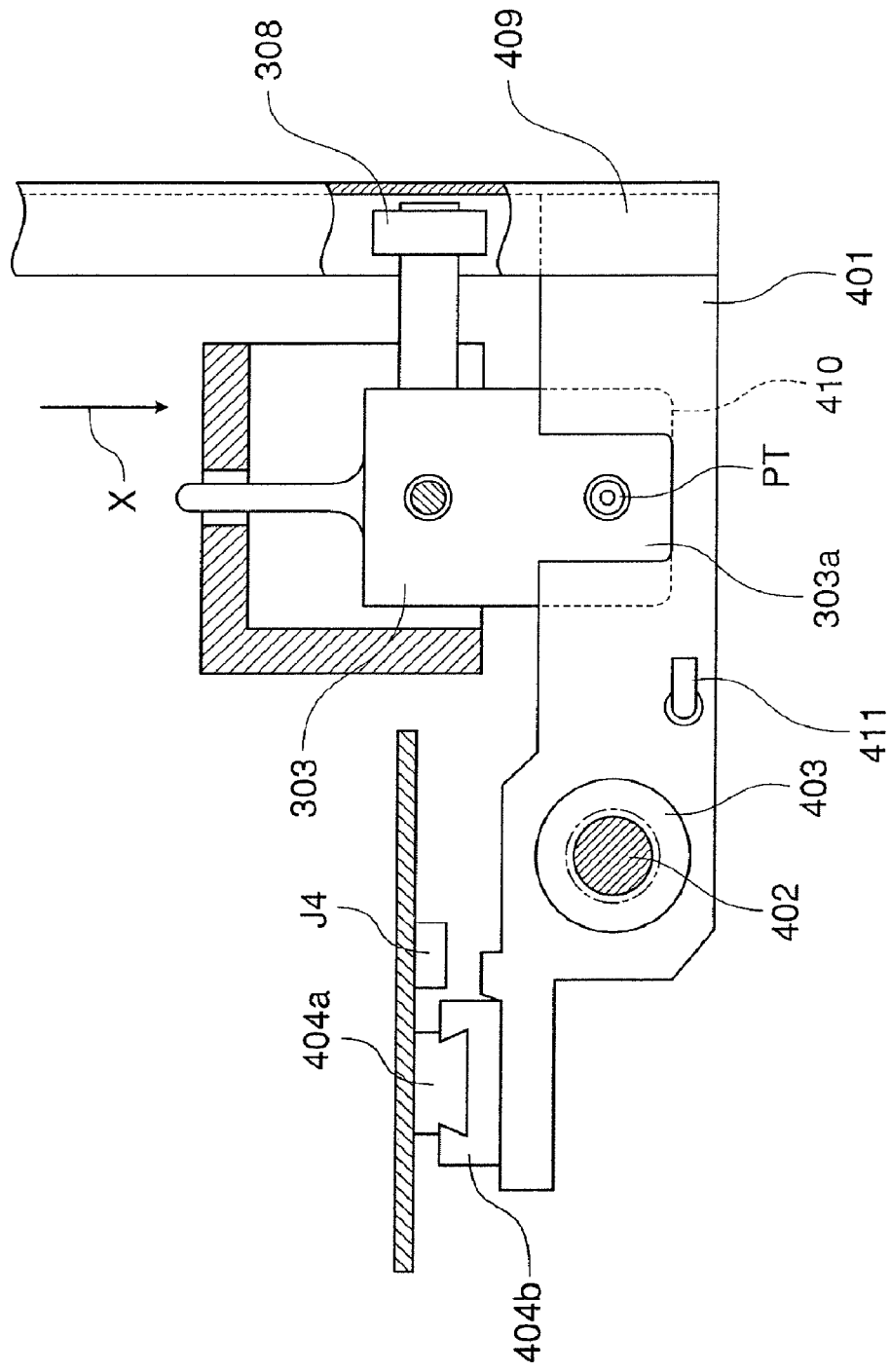
FIG. 20 is a view from a C-C arrow direction in FIG. 19.

FIG. 19 is a left side view of the pipette vertically driving section 400, and FIG. 20 is a view from a C-C arrow direction in FIG. 19.

As shown in FIG. 19, the pipette vertically driving section 400 includes an elongated main arm 401 extending horizontally, a thread shaft 402 extending perpendicularly through the main arm 401 and rotatably supported by a support plate 412, a nut 403 fixed to the main arm 401 in threading engagement with the thread shaft 402, a slide rail 404a disposed parallel to the thread shaft 402 on the support plate 412, a sliding member 404b provided at a left end of the main arm 401 in slidable engagement with the slide rail 404a for vertically guiding the main arm 401, and a pipette up and down motor (stepping motor) 405 fixed to the support plate 412.

Pulleys 406 and 407 are fixed to an upper end of the thread shaft 402 and an output shaft of the motor 405, respectively, and a timing belt 408 is stretched between the pulleys 406 and 407. Therefore, the main arm 401 is movable vertically up and down by the driving of the motor 405. A pipette top position sensor J4 for sensing that the main arm 401 reaches the uppermost position is provided on the support plate 412.

A guide arm 409 is horizontally fixed to a right end of the main arm 401 (is perpendicularly fixed to a paper) in engagement with the guide roller 308 of the pipette vertically sliding section 300 (FIG. 18). The main arm 401 has a cross-shaped recess 410 provided in a surface thereof opposed to the cross-shaped end 303a of the pipette holder 303 (FIGS. 17 and 18). As shown in FIG. 20, the end 303a of the pipette holder 303 is removably inserted in an arrow direction X into the recess 410 with a proper clearance. In this case, a force for the vertical movement of the main arm 401 is directly transmitted to the pipette holder 303.

A lock rod 411 extends vertically through a middle portion of the main arm 401 with an upper end bent portion thereof in engagement with the main arm 401. In this embodiment, the main arm 401 is composed of an aluminum alloy (A5052) and has a section of 20 mm×26 mm and a length of 108 mm. The guide arm 409 is prepared by folding a 0.5-mm thick steel plate (SECC) into an open square shape in section, and has a length of 180 mm.

Operations of Pipette Horizontally Driving Section, Pipette Vertically Sliding Section and Pipette Vertically Driving Section When the blood sample is quantitatively dispensed out of the sample vessel SP1 set in the sample rack 18 in the sample setting section 6, the pipette back and forth motor 205 is driven to insert the end 303a of the pipette holder 303 into the recess 410 of the main arm 401 as shown in FIG. 20.

The pipette up and down motor 405 is driven to move up the main arm 401 until the actuation of the pipette top position sensor J4 (FIGS. 4 and 19). With the end 303a is fitted in the recess 410, the centers of the thread shaft 402, the pipette PT and the sample vessel SP1 are present in the same plane, and a moment exerted on the pipette PT by the thread shaft 402 is minimized. Therefore, the torque of the motor 405 is efficiently converted into a pipette lowering force, when the pipette PT is lowered by the motor 405.

Figure 21:
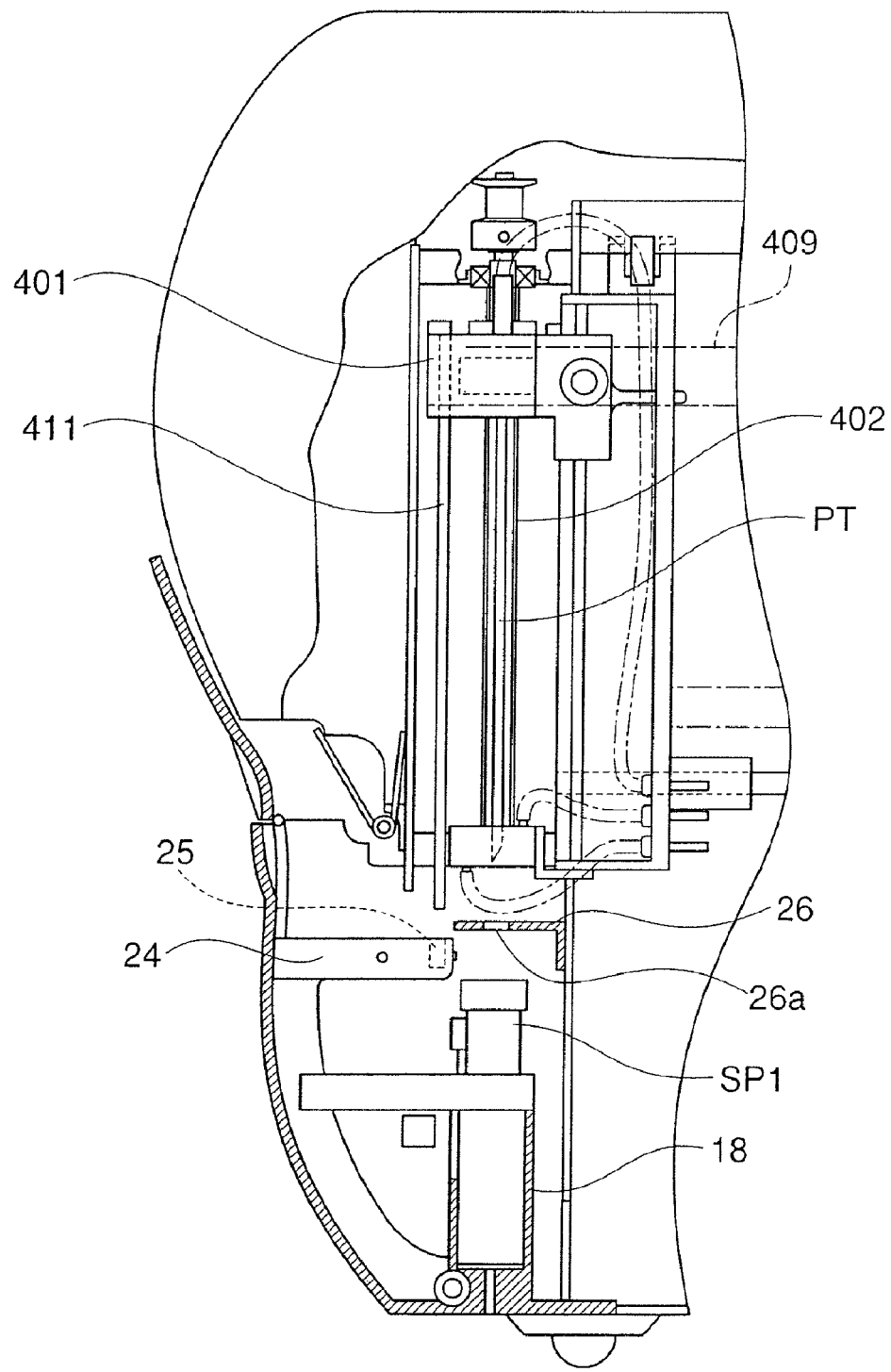
FIG. 21 is a diagram for explaining the operation of the pipette vertically driving section according to this invention.
Figure 22:
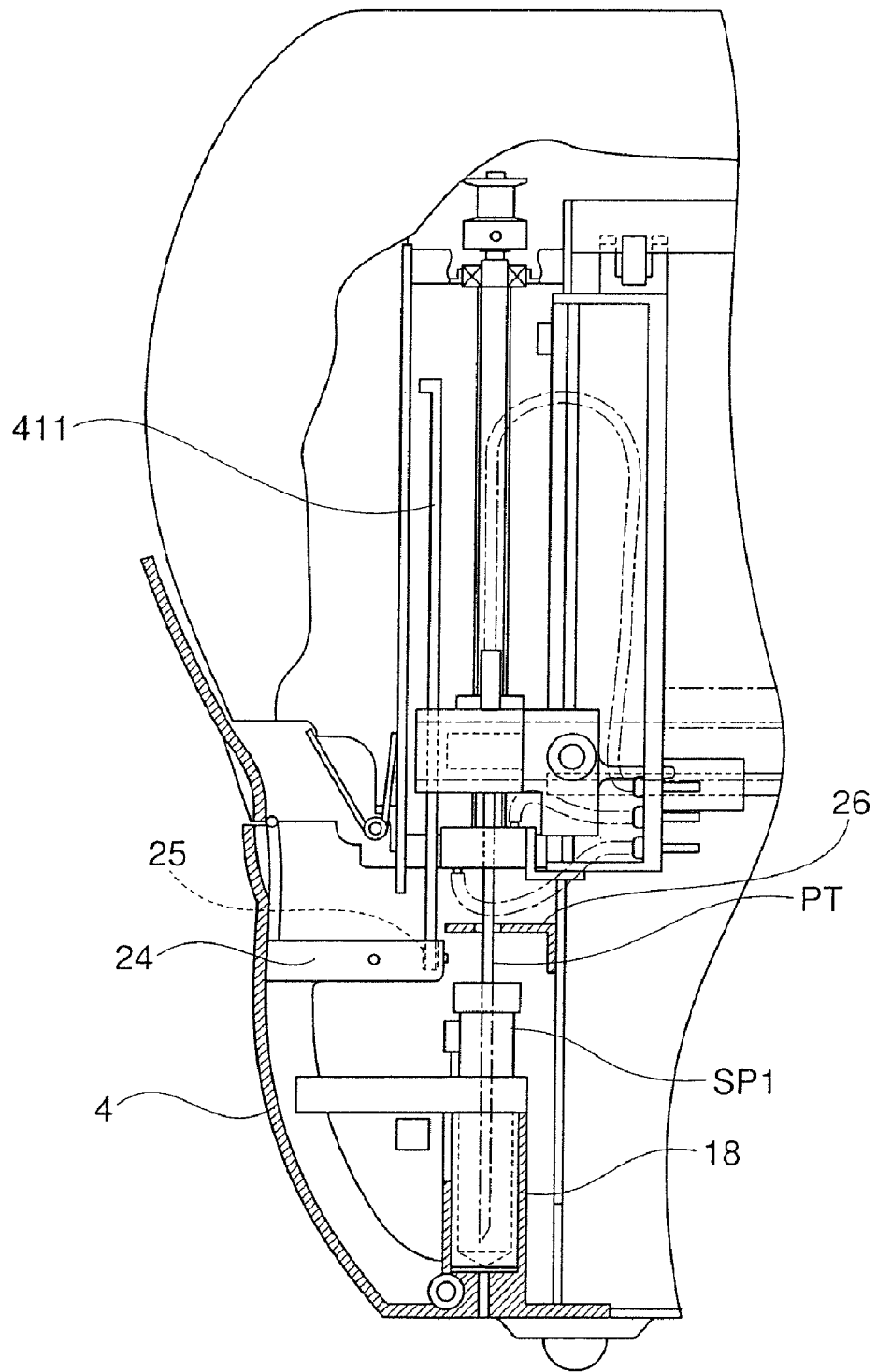
FIG. 22 is a diagram for explaining the operation of the pipette vertically driving section according to this invention.

Then, the motor 405 is driven to lower the pipette PT through a through-hole 26a of a sample vessel lift preventing stopper 26 as shown in FIG. 21, and to allow the pipette PT to virtually reach the bottom of the sample vessel SP1 as shown in FIG. 22. Where the sample vessel SP1 is a vacuum blood sampling tube with a rubber cap, it is necessary to piece the rubber cap with the tip of the pipette PT. Therefore, an input electric current greater than usual is supplied to the motor 405 from a driver circuit section (to be described later) to provide a greater output torque when the pipette PT is lowered to pierce through the rubber cap.

When the pipette PT is lowered, the lock rod 411 is brought into engagement with a lock hole 25 provided in a projection piece 24 projecting inward of the sample setting panel 4 as shown in FIG. 22, so that the pipette PT and the sample vessel SP1 are prevented from being damaged when the sample setting panel 4 is inadvertently opened. Where the sample vessel SP2 is set in the sample rack 18 with the intervention of the adaptor AD2 as shown in FIG. 41, the adaptor recognizing sensor J2 is actuated. Therefore, a control section 500 to be described later controls a lowering distance of the pipette PT to allow the tip of the pipette PT to virtually reach the bottom of the sample vessel SP2.

In the state shown in FIG. 22, the pipette PT is employed for sampling the blood sample from the sample vessel SP1.

Upon completion of intake of the blood sample, the pipette PT returns to the position shown in FIG. 21. Although there would be a possibility that the sample vessel SP1 along with the pipette PT is lifted together with the rubber cap sticking thereto when the pipette PT is removed from the sample vessel SP1, the stopper 26 prevents the rubber cap from being lifted together.

When the pipette PT is returned to the position shown in FIG. 21, the pipette back and forth motor 205 is driven to withdraw the end 303a of the pipette holder 303 from the recess 410 of the main arm 401 in a direction opposite to the arrow direction X in FIG. 20, and then move the pipette PT to an upper side of the mixing chamber 70 and the detector 50 with the guide roller 308 rotated in contact with the inner surface of the guide arm 409. Then, the pipette up and down motor 405 is driven, whereby a driving force thereof is transmitted to the pipette holder 303 through the main arm 401, the guide arm 409 and the guide roller 308. Thus, the pipette PT is lowered and then lifted.

Construction of Detector

Figure 23:
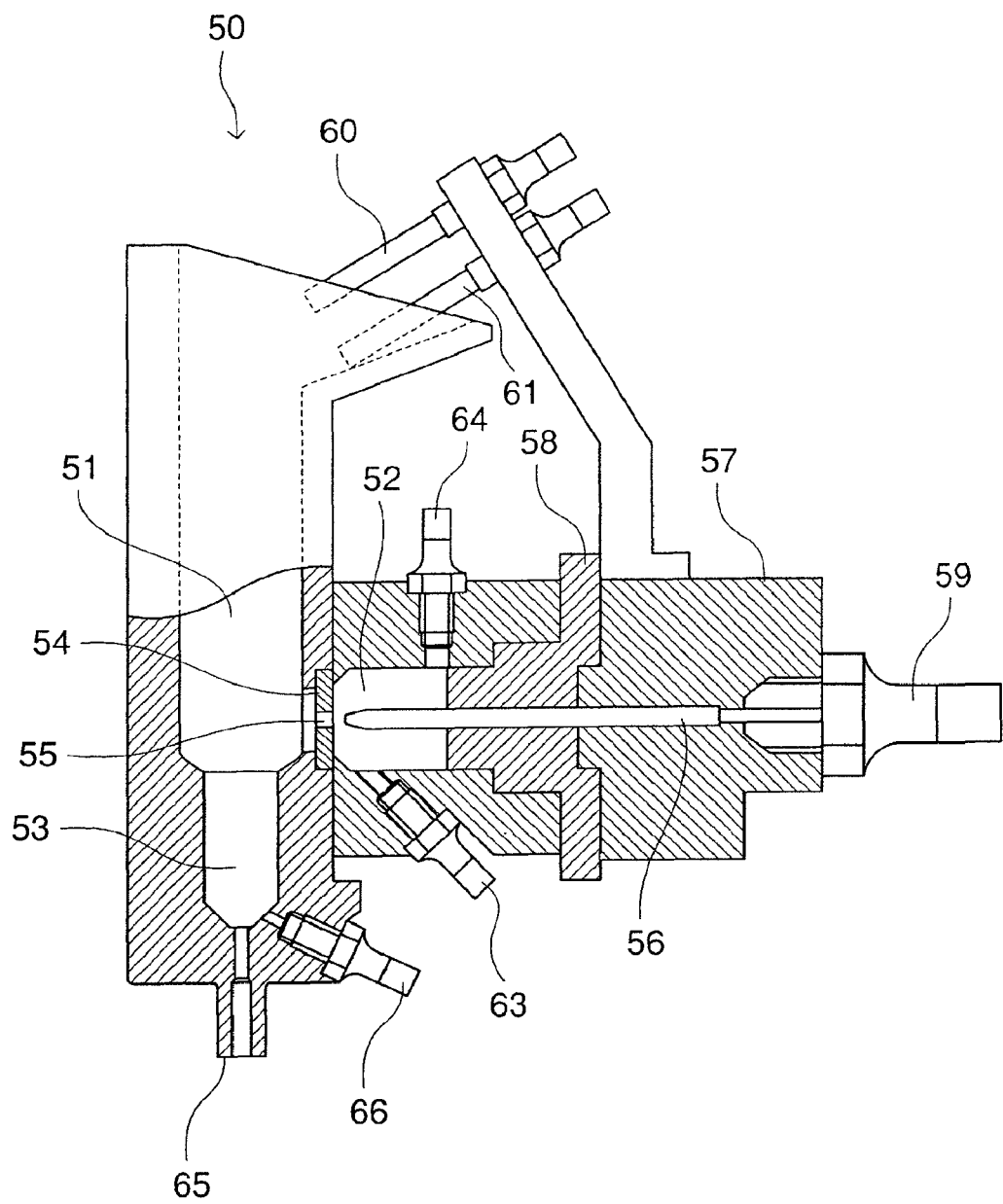
FIG. 23 is a partly cut-away front view of major portions of a detector according to this invention.
Figure 24:
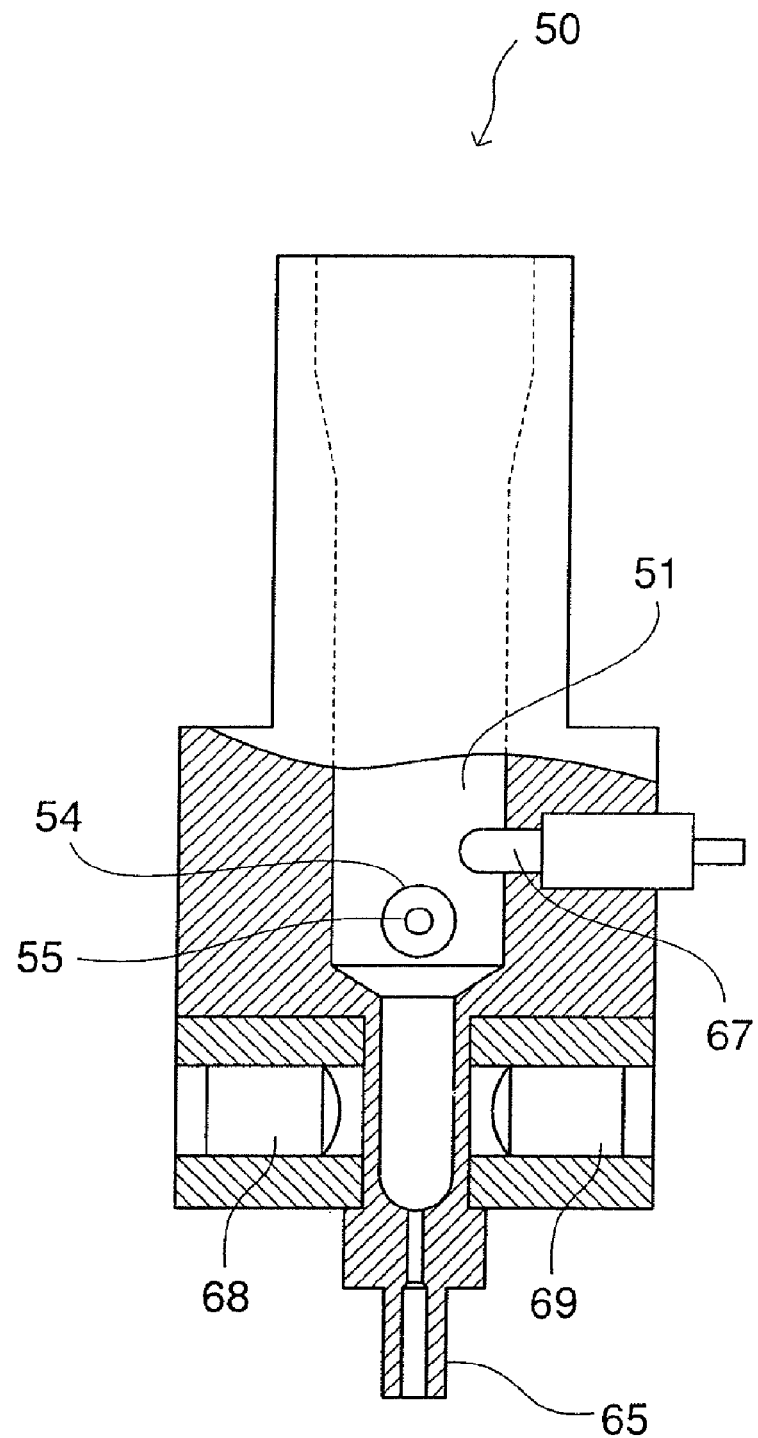
FIG. 24 is a partly cut-away side view of major portions of the detector according to this invention.

FIGS. 23 and 24 are a partly cut-away front view and a partly cut-away side view, respectively, of major portions of the detector 50. The detector 50 is composed of a transparent polysulfone resin. As shown, the detector 50 includes first, second and third container chambers 51, 52, 53 for containing liquids for the analysis. The first container chamber 51 has an upper portion open to the atmosphere. The first container chamber 51 and the third container chamber 53 communicate with each other.

A ruby orifice disk 54 is provided as a partition between the first container chamber 51 and the second container chamber 52, and the disk 54 has an orifice 55 having a diameter of 80 μm. The second container chamber 52 is provided with a jet nozzle 56. The jet nozzle 56 is supported by a nozzle support member 57 and a first electrode 58, and extends through the second container chamber 52 with its distal end facing toward the orifice 55 and with its tail end communicating with a liquid supply nipple 59. The first electrode 58 is composed of a stainless steel, and exposed to the inside of the second container chamber 52.

The detector 50 further includes nozzles 60, 61 for supplying the diluent and the hemolyzing agent to the first container chamber 51, nipples 63, 64 for supplying and draining liquid into/from the second container chamber 52, and a liquid draining nipple 65 and an air bubble injecting nipple 66 provided in the bottom of the third container chamber 53.

As shown in FIG. 24, the detector 50 further includes a second platinum electrode 67 projecting in the first container chamber 51, and a light emitting diode 68 and a photodiode 69 respectively disposed on opposite sides of the third container chamber 53. The light emitting diode 68 emits light having a wavelength of 555 nm, and the photodiode 69 detects the intensity of the light transmitting through the third container chamber 53. The light emitting diode 68 and the photodiode 69 are employed for measurement of a hemoglobin amount (HGB).

As will be described later, the first and third container chambers 51, 53 are employed for preparation of a white blood cell measurement specimen, and the first and second container chambers 51, 52 are employed for counting the numbers of the white blood cells, the platelets and the red blood cells.

Construction of Mixing Chamber (Container for Mixing Liquids)

Figure 25:
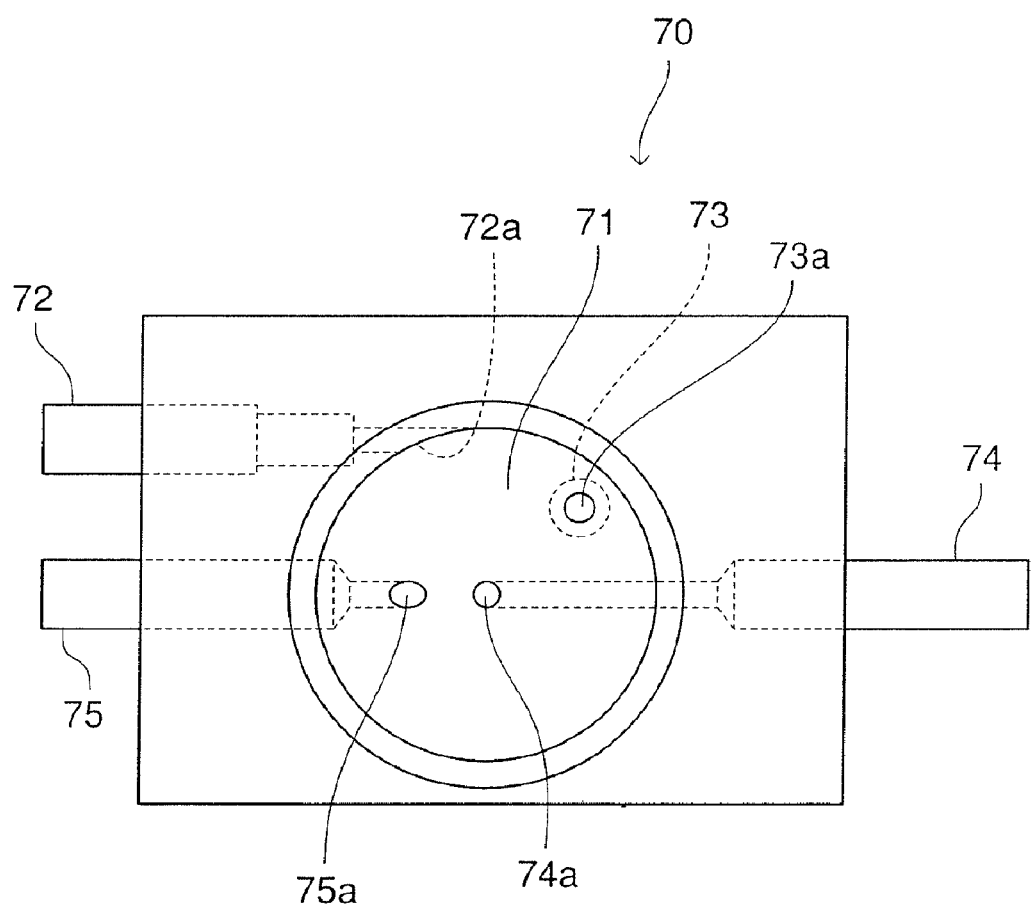
FIG. 25 is a top surface view of a mixing chamber according to this invention.
Figure 26:
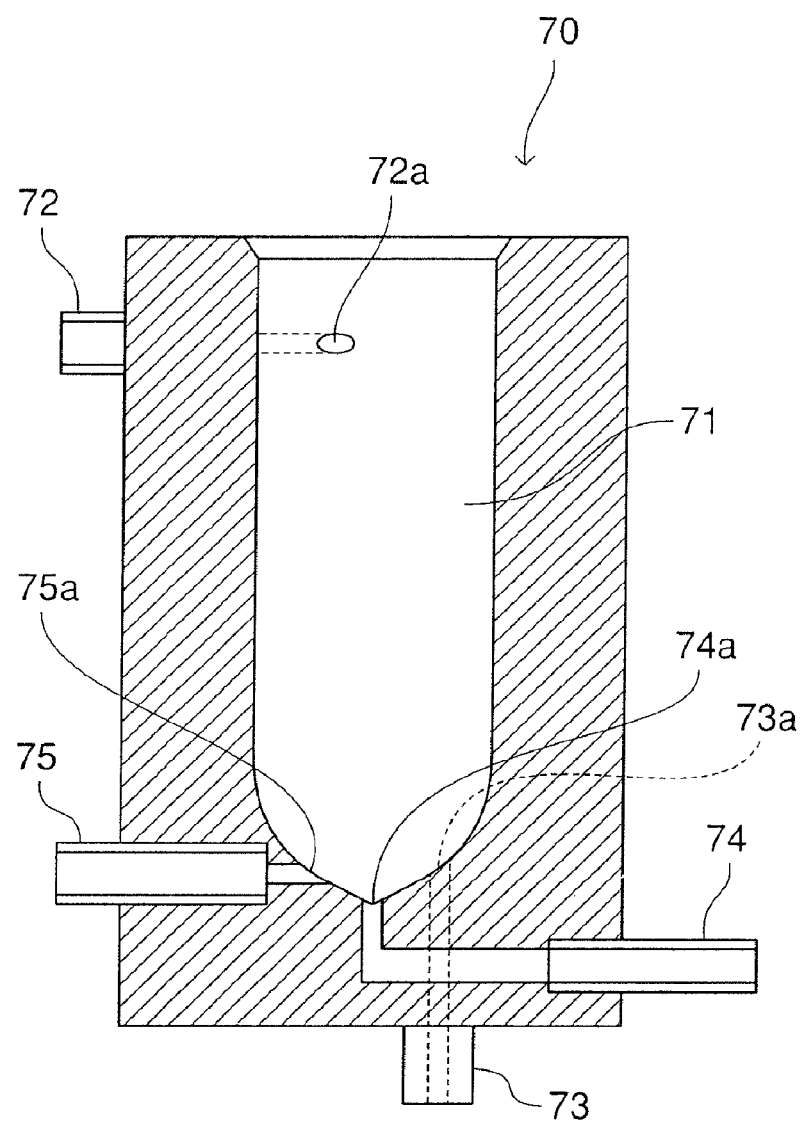
FIG. 26 is a vertical sectional view of the mixing chamber shown in FIG. 25.

FIGS. 25 and 26 are a plan view and a vertical sectional view, respectively, of the mixing chamber 70. The mixing chamber 70 includes a container portion 71 for mixing the blood sample. The container portion 71 has a cylindrical shape with its top open to the atmosphere. A diluent supplying nipple 72 is provided in an upper portion of the container portion 71. A nipple 73 for discharging a liquid mixture, a nipple 74 for draining residual liquid from the container portion 71, and a nipple 75 for injecting air bubbles (air) for agitating the liquid in the container portion 71 are provided in the bottom of the container portion 71.

The nipples 72, 73, 74, 75 are respectively connected to a liquid supply port 72a, liquid discharge ports 73a, 74a, and an air supply port 75a, which communicate with an interior surface of the container portion 71. The liquid supply port 72a opens so as to supply the liquid from the upper portion along the inner circumferential surface of the container portion 71. Where the diluent is supplied into the mixing chamber 70 as will be described later for cleaning the chamber, the interior surface of the container portion 71 is efficiently cleaned with the diluent ejected from the liquid supply port 72a.

The mixing chamber 70 is produced by injection-molding a thermoplastic resin such as a polyether amide having a chemical resistance. The interior surface of the container portion 71 has been roughened to an arithmetic average surface roughness Ra of 0.29 μm so as to be imparted with a sufficiently high wettability with respect to the diluent. Therefore, the diluent injected from the liquid supply port 72a is supplied into the bottom of the container portion 71 without residing as liquid drops on the interior surface, so that the blood sample preliminarily supplied can accurately be diluted predetermined times.

Constructions and Operations of Pipette and Cleaner (Pipette Cleaning Device)

Figure 27:
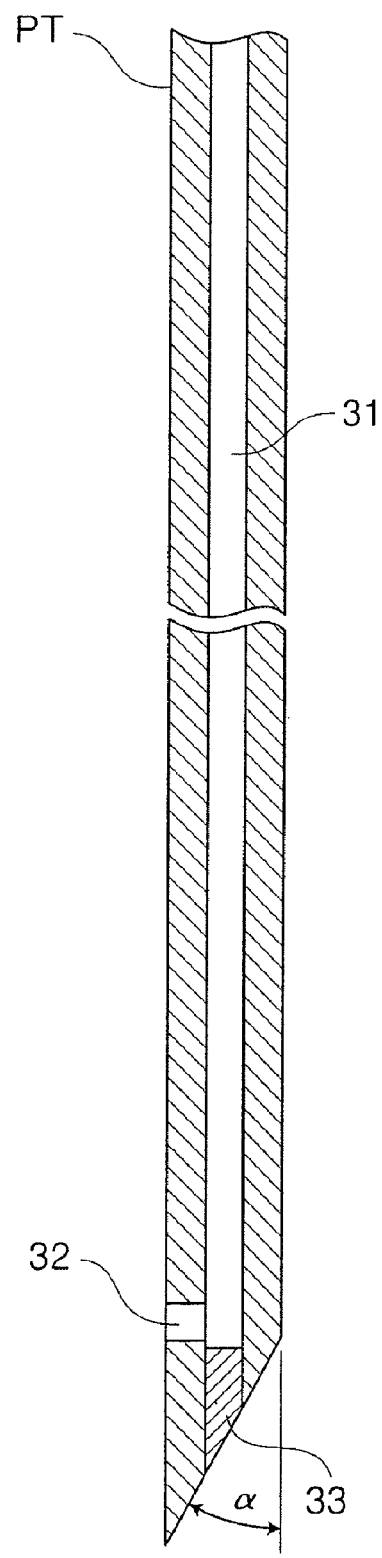
FIG. 27 is a vertical sectional view of a pipette according to this invention.

FIG. 27 is a vertical sectional view of the pipette PT. The pipette PT is a stainless steel pipe, which has a suction flow path 31 coaxially extending therein, and a distal tip sharply cut at an angle α of 30 degrees. Where the sample vessel SP1 with the cap is employed, the cap is pierced with the distal tip. A distal end of the suction flow path 31 is sealed with a stainless steel seal 33, and a suction port 32 is open in a side wall of the pipette PT with its axis extending perpendicularly to the axis of the pipette PT.

Figure 28:
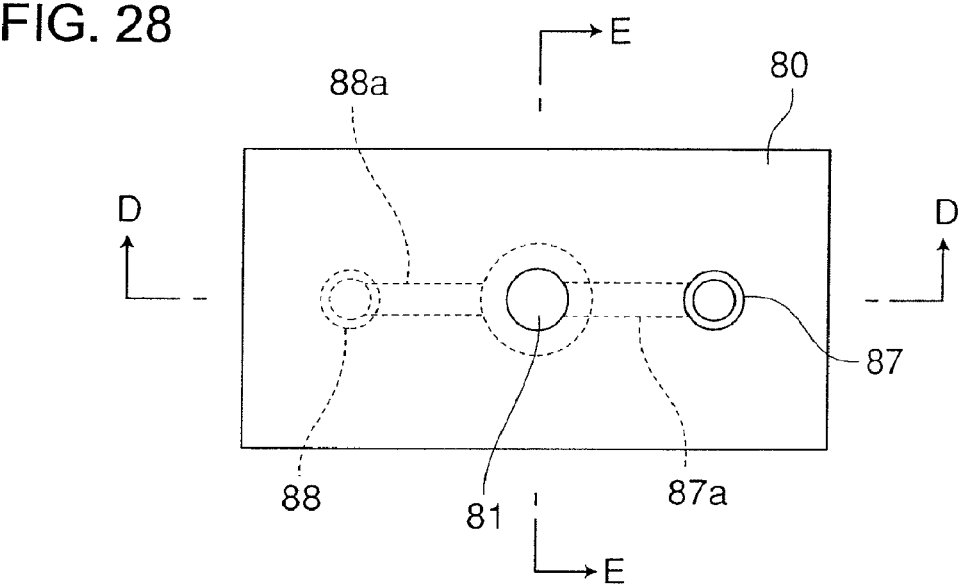
FIG. 28 is a top surface view of a cleaner body according to this invention.
Figure 29:
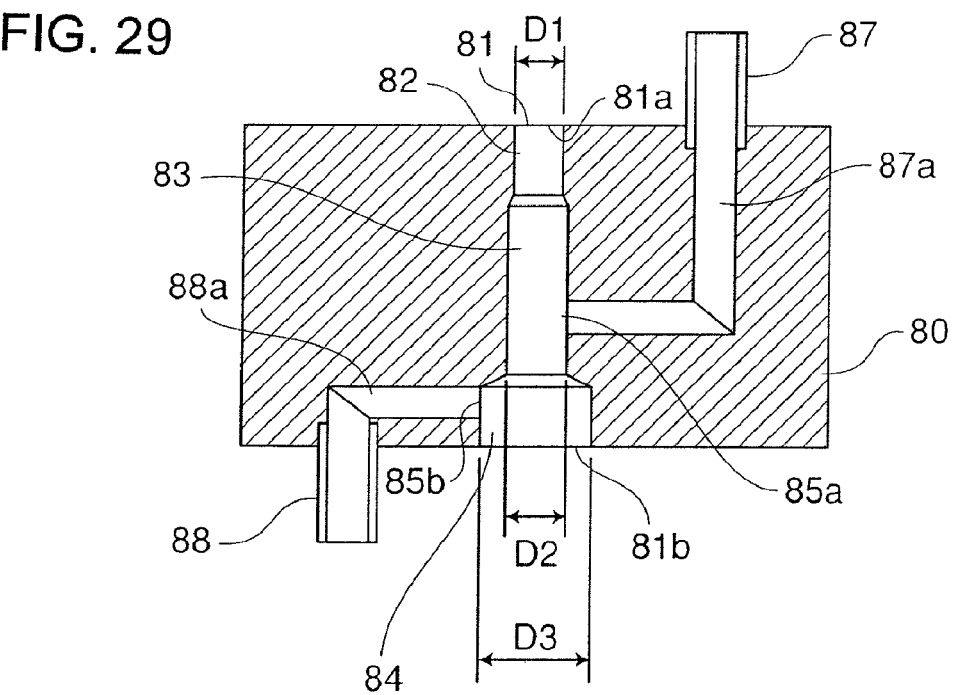
FIG. 29 is a view from a D-D arrow direction in FIG. 28.
Figure 30:
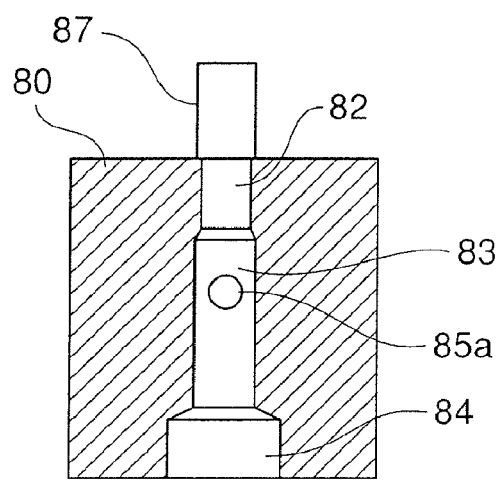
FIG. 30 is a view from an E-E arrow direction in FIG. 28.

FIG. 28 is a plan view of the cleaner body 80. FIGS. 29 and 30 are views from a D-D arrow direction and from an E-E arrow direction, respectively in FIG. 28. As shown, a cleaner body 80 has a pipette through-hole 81 centrally extending therethrough, so that the pipette PT is vertically inserted in the pipette through-hole 81 from an inlet 81a to an outlet 81b. The pipette through-hole 81 has a round cross section.

The pipette through-hole 81 includes a pipette guide hole 82, a first through-hole 83 and a second through-hole 84 serially and coaxially disposed in this order from the inlet 81a to the outlet 81b. The pipette guide hole 82 has an inner diameter slightly greater than the outer diameter of the pipette PT, and serves to guide the pipette PT so as to align the axis of the pipette PT with the axes of the first and second through-holes 83, 84.

On the other hand, the first and second through-holes 83, 84 constitute a pipette cleaning hole for cleaning the pipette. A first opening 85a and a second opening 85b are formed in the first and second through holes 83, 84, respectively.

The cleaner body 80 includes a cleaning liquid drain path 87a allowing communication between the first opening 85a and a cleaning liquid draining nipple 87, and a cleaning liquid supply path 88a allowing communication between the second opening 85b and a cleaning liquid supplying nipple 88.

The pipette guide hole 82, the first through-hole 83 and the second through-hole 84 respectively have inner diameters D1, D2 and D3 which are set at 105%, 115% and 200% of the outer diameter of the pipette PT. Where the pipette PT has an outer diameter of 2.0 mm, for example, D1=2.1 mm, D2=2.3 mm and D3=4.0 mm.

Figure 31:
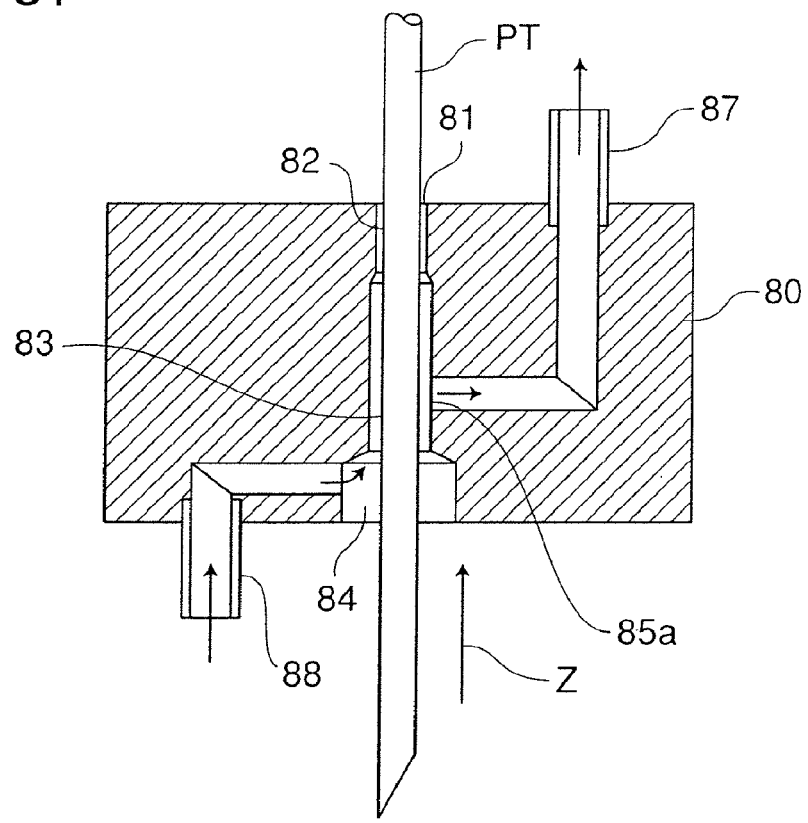
FIG. 31 is a diagram for explaining the operation of the cleaner body according to this invention.

When the cleaning liquid (the diluent in this embodiment) is supplied from the nipple 88 into the second through-hole 84 and sucked from the nipple 87 with the pipette PT extending from the upper side to the lower side through the pipette through-hole 81 as shown in FIG. 31, the cleaning liquid flows in uniform contact with the exterior of the pipette PT from the second through-hole 84 into the first through-hole 83, and drained from the nipple 87.

Therefore, when the pipette PT is moved up in the arrow direction Z in this state, the blood sample and the like adhering on the exterior (outer circumferential surface) of the pipette PT is washed away with the cleaning liquid and drained.

Figure 32:
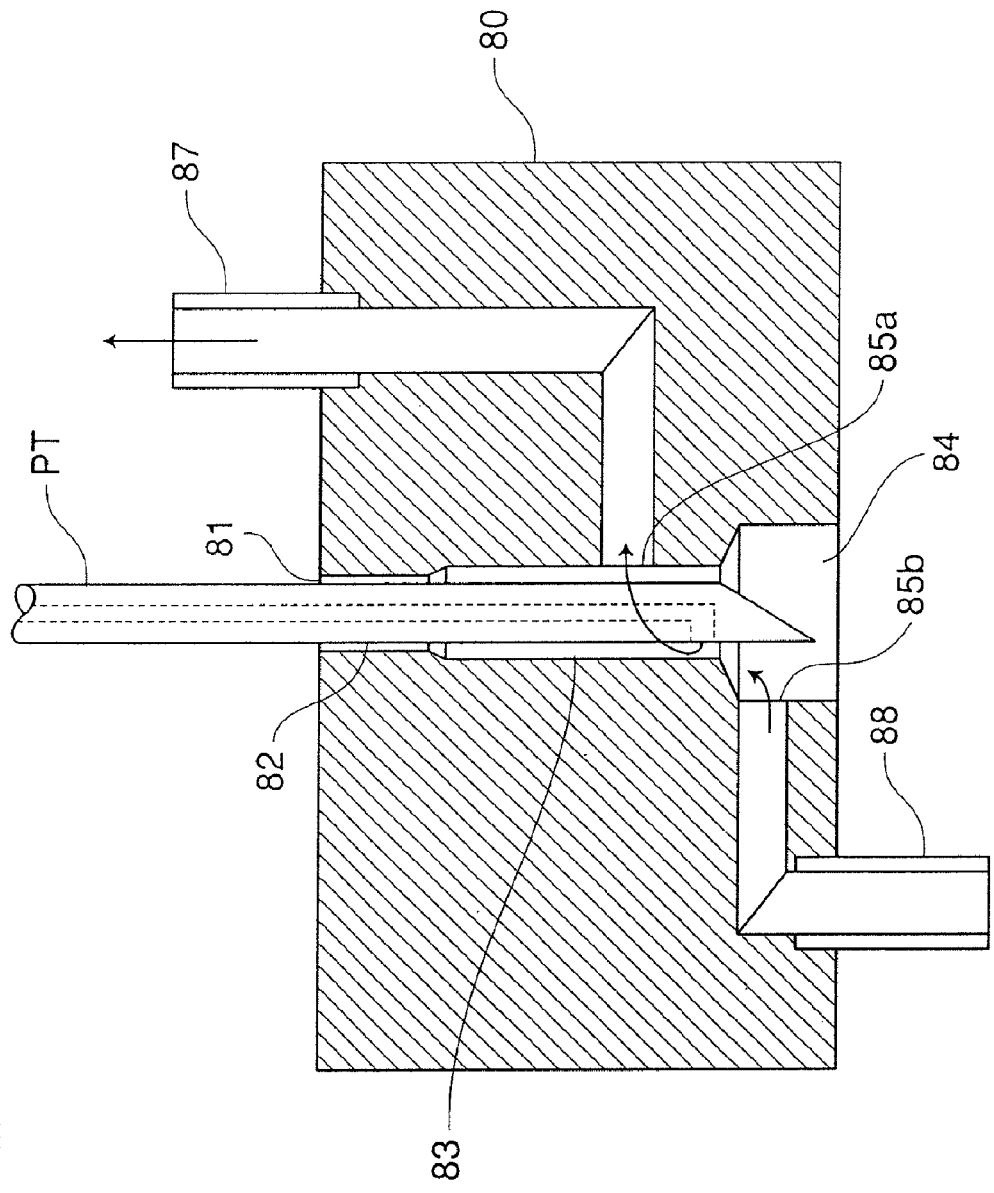
FIG. 32 is a diagram for explaining the operation of the cleaner body according to this invention.

When the cleaning liquid flows into the nipple 87 from the nipple 88, the distal suction port 32 with the tip of the pipette PT is kept within the first through-hole 83a as shown in FIG. 32. When the cleaning liquid is supplied from the proximal end of the pipette PT to the distal suction port 32 with the tip of the pipette PT, the cleaning liquid having passed through the suction flow path 31 of the pipette PT is drained from the suction port 32 of the pipette PT, and sucked into the nipple 87 through the first opening 85a but not drained into the second through-hole 84. Thus, the interior of the pipette PT (i.e., the inner surfaces of the suction flow path 31 and the suction port 32 of the pipette PT) is cleaned.

Figure 33:
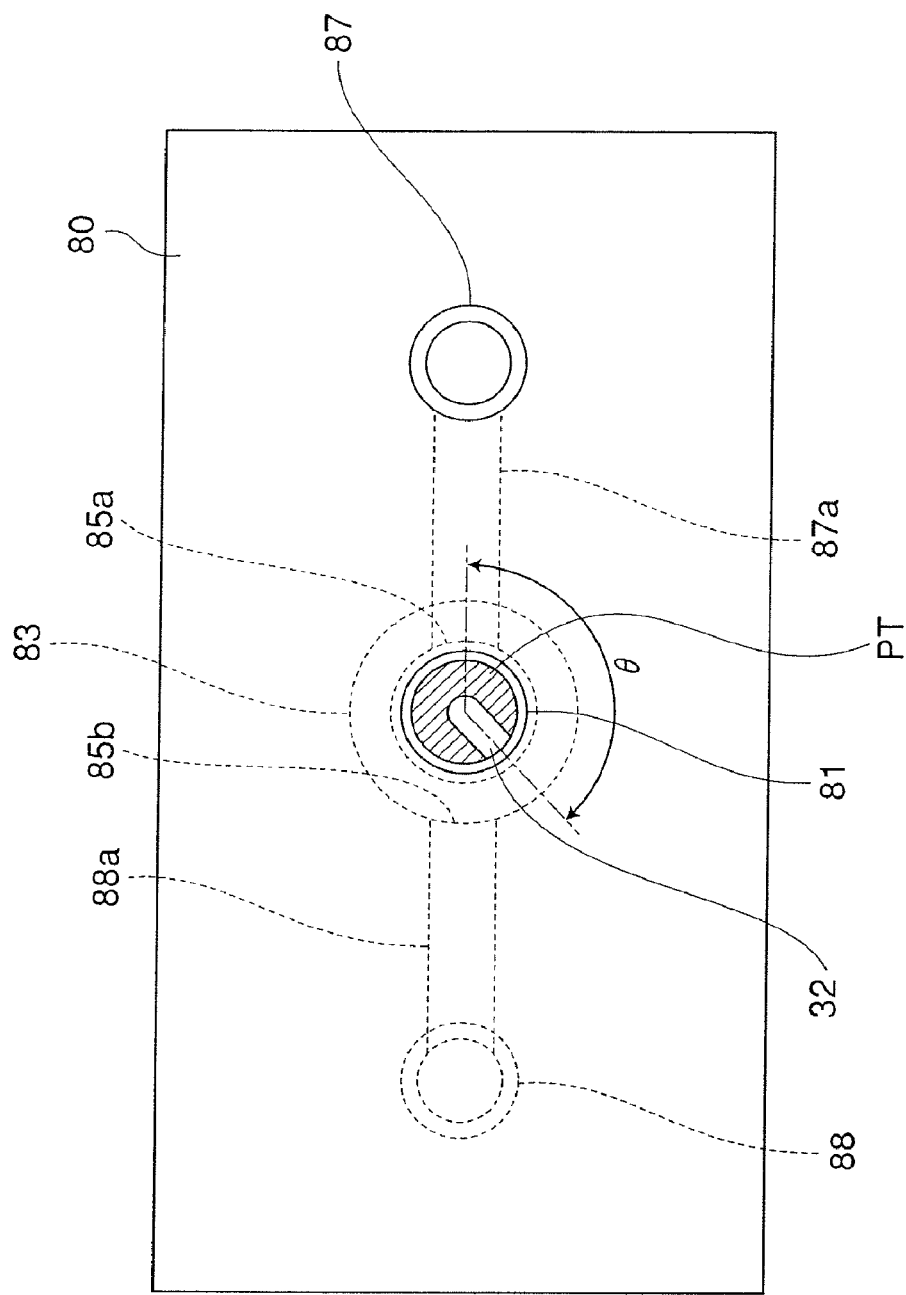
FIG. 33 is a diagram for explaining a positional relationship between the cleaner body and the pipette shown in FIG. 28.

A positional relationship between the cleaner body 80 and the pipette PT as seen axially of the pipette PT is shown in FIG. 33. As shown, the pipette PT is positioned with respect to the cleaner body 80 with the axis of the suction port 32 and the axis of the opening 85b of the cleaning liquid drain path 87a forming an angle θ of greater than 90 degrees. This is because the following phenomena have experimentally been observed.

(1) If $\theta \leq 90$ degrees, the diluent (to be described later) filled in the suction flow path 31 and the suction port 32 of the pipette PT is sucked out by the negative pressure in the cleaning liquid drain path 87a and a void occurs in the suction port 32 when the exterior or interior of the pipette PT is cleaned. Therefore, the blood sample is introduced into the void in the suction port 32 before the blood sample is sucked to be quantified by means of the pipette PT. Accordingly, the blood sample is sucked into the pipette PT in an amount greater by the previously introduced amount than an intended amount, resulting in erroneous quantifying.

(2) If $\theta > 90$ degrees, the negative pressure in the cleaning liquid drain path 87a exerts no direct effect on the suction port 32. Therefore, accurate quantifying can be ensured because no void occurs in the suction port 32 when the exterior or interior of the pipette PT is cleaned.

Another Exemplary Pipette

Figure 34:
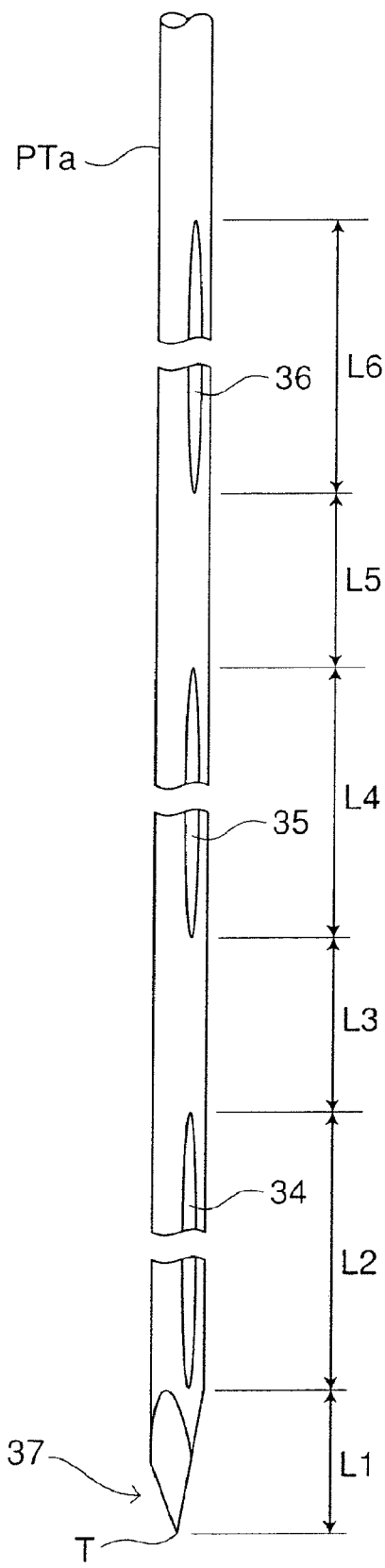
FIG. 34 is a vertical sectional view of another exemplary pipette according to this invention.
Figure 35:
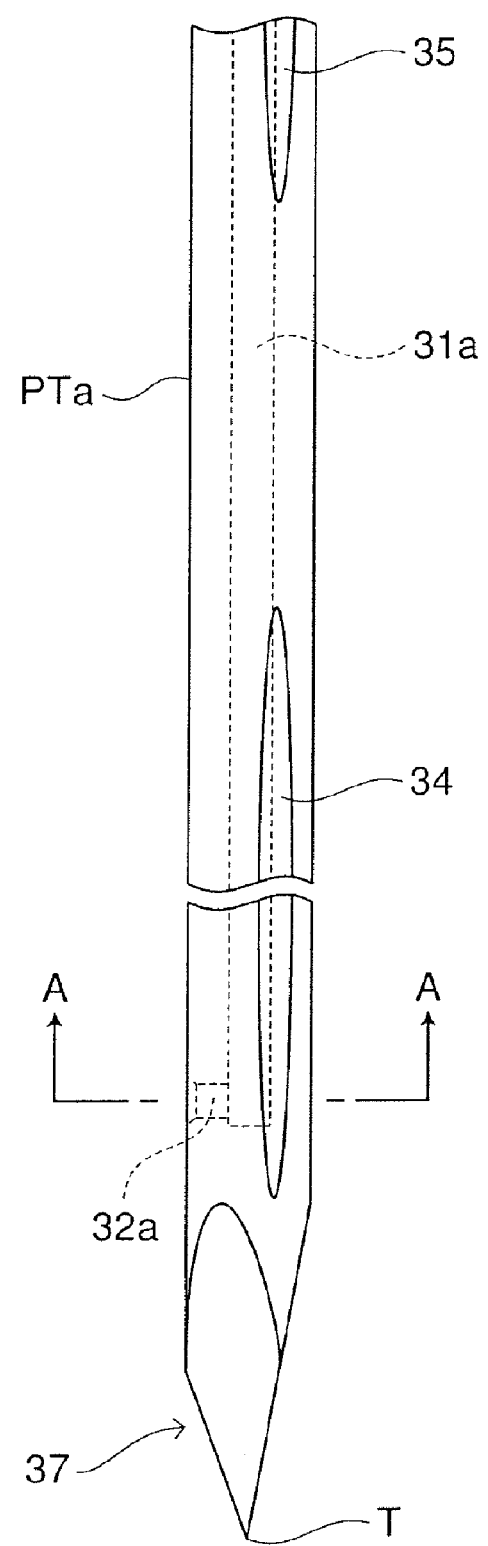
FIG. 35 is an enlarged view of a major portion of the pipette shown in FIG. 34.
Figure 36:
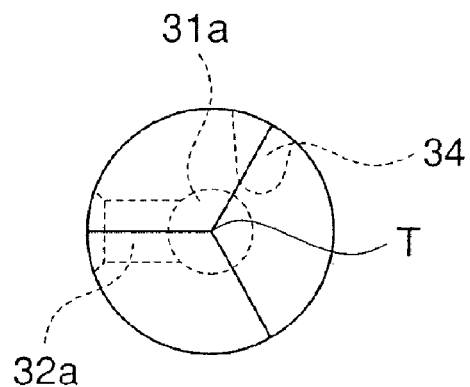
FIG. 36 is an end view of the pipette shown in FIG. 35.
Figure 37:
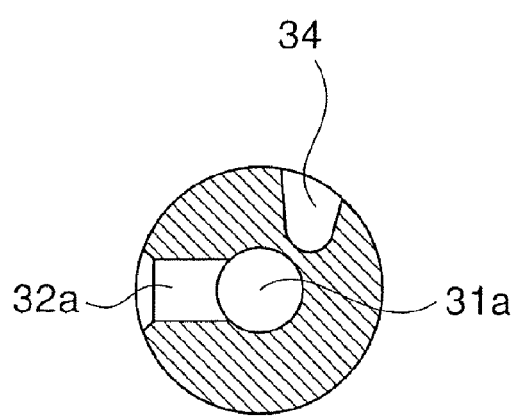
FIG. 37 is a view from an A-A arrow direction in FIG. 35.

FIG. 34 is a side view illustrating another exemplary pipette PTa to be suitably employed instead of the pipette PT (FIG. 27) where a vacuum blood sampling tube (sealed with a rubber cap) is particularly used as the sample vessel SP1, and FIG. 35 is an enlarged view of a major portion of FIG. 34, FIG. 36 is an end view of the pipette PTa, and FIG. 37 is a view from an A-A arrow direction in FIG. 35.

As shown, the pipette PTa is a stainless steel pipe having an outer diameter of 1.5 mm, which has a suction flow path (fluid path) 31a having an inner diameter of 0.5 mm centrally extending therein. A sharp pyramidal portion (head) 37 having a trigonal pyramid shape tapered toward an apex T is formed at a distal end of the pipette PTa as shown in FIGS. 34 and 35. The apex T is positioned on the central axis of the pipette PTa as shown in FIG. 36. With this construction, a lowering force of the pipette PTa is concentrated at the apex T, whereby the rubber cap of the sample vessel SP1 is easily pierced with the pipette PTa. The pyramidal portion 37 may have a conical shape or a quadrangular pyramid shape. The rubber cap through which the pipette PTa pierces has a thickness of about 5 mm.

The suction flow path 31a has a distal end portion sealed with a stainless steel seal as in that of the pipette PT of FIG. 27. The pipette PTa has a suction port 32a (FIG. 35) open in a side wall thereof. The suction port 32a has an axis extending perpendicularly to the axis of the pipette PTa, and communicates with the suction flow path 31a (FIG. 35).

Further, the pipette PTa has three elongated recesses 34, 35 and 36 each having a groove shape provided in an outer surface thereof as extending in line parallel to the axis thereof as shown in FIG. 34. The pyramidal portion 37 has a length L1 of 4 mm, the recesses 34, 35 and 36 have lengths L2, L4 and L6 of 25 mm, 20 mm and 30 mm, respectively. An interval L3 between the recesses 34 and 35 is 5 mm, and an interval L5 between the recesses 35 and 36 is 5 mm. From the viewpoint of reduction in production costs, it is preferred that the recesses 34, 35 and 36 are provided in line parallel to the axis of the pipette PTa. However, the recesses may be provided in two or three lines parallel to the axis of the pipette PTa or may be provided in an outer surface of the pipette PTa as extending spirally thereof.

After the distal end of the pipette PTa is lowered to pierce through the rubber cap, the recess 34 serves to let the internal pressure of the sample vessel back to the atmospheric pressure immediately. When the pipette PTa is kept lowering, a part of the rubber cap goes into the recess 34, and then is pushed out through the interval portion L3 of the pipette PTa.

When the pipette PTa is further lowered, the part of the rubber cap goes into the recess 35 and is pushed out through the interval portion L5 of the pipette PTa, so that a through-hole is enlarged. When a distal tip of the pipette PTa virtually reaches the bottom of the sample vessel SP1 and the recess 36 is disposed oppositely to the rubber cap, the part of the rubber cap does not go into the recess 36. Accordingly, the recess 36 serves to define an air hole through the rubber cap, and the sample vessel SP1 has an inside open to the atmosphere via the air hole to a sufficient degree. Thus, the sample (blood) is sucked smoothly from the sample vessel SP1 by means of the pipette PTa.

The three elongated recesses 34, 35 and 36 are arranged in a straight line extending along the axis of the pipe from one ridgeline of the trigonal pyramid formed at the distal end of the pipette PTa as shown in FIG. 36. With this construction, the rubber cap is split by the pipette PTa with its ridgeline portions of the trigonal pyramid after being pierced with the pipette PTa, and the recess 36 is disposed oppositely to one of the split portions of the rubber cap. Thus, the recess 36 can define the air hole through the rubber cap more effectively.

The exterior of the pipette PTa is cleaned by the cleaner S as in that of the pipette PT. At the same time, the recesses 34, 35 and 36 are cleaned in this manner. As a result, there is no need to provide another cleaner in the analyzer for cleaning only the recesses 34, 35 and 36.

FIGS. 67 and 68 are a sectional view of a pipette PTb and a plane view of a distal end thereof, respectively, according to another embodiment of this invention. The pipette PTb is employed suitably to suck a small-volume sample from the vicinity of a bottom of an upper-open sample vessel having a small capacity for storing the small-volume sample.

As shown, the pipette PTb is composed of a stainless steel pipe having an outer diameter of 1.5 mm, which has a suction flow path 31b having an inner diameter 0.6 mm coaxially extending therein. The pipette PTb has a distal end with round portions having a radius of 0.4 mm and with a groove 32b crossing diametrically over the distal end. The width of the groove 32b is the same as the diameter of the suction flow path 31b, and the depth of the groove 32b is 0.3 mm. With such a distal end shape, the distal end of the pipette PTb is brought into contact with the bottom of the sample vessel to suck up the sample, and then the sample is sucked into the suction flow path 31b through the groove 32b.

Constructions of Fluid Circuit and Electrical Circuit

Figure 42:
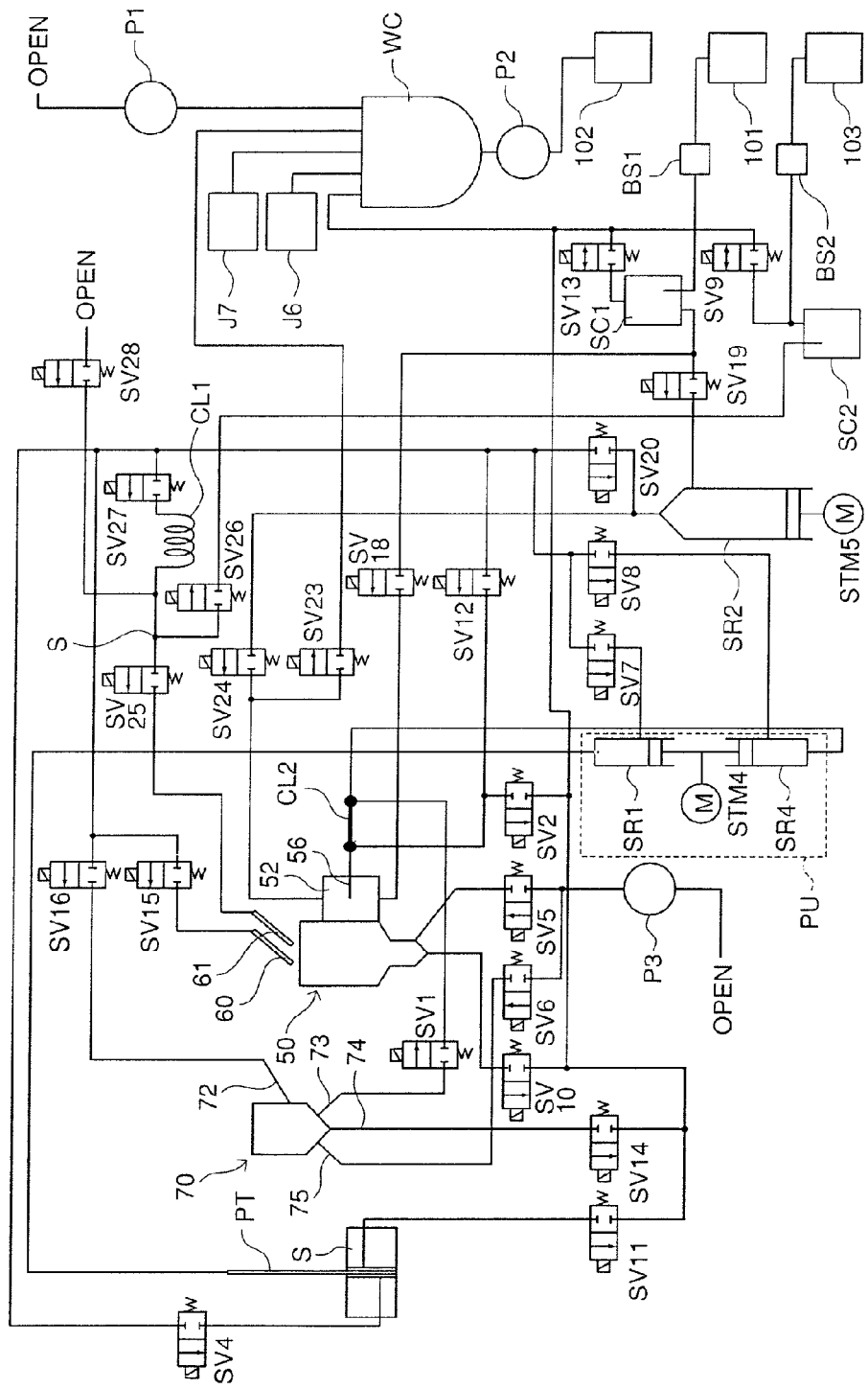
FIG. 42 is a fluid circuit diagram according to this invention.

FIG. 42 is a system diagram illustrating a fluid circuit according to the embodiment of the invention. In the fluid circuit, the pipette PT, the cleaner S, the mix chamber 70, the detector 50, a negative pressure pump P1, a liquid draining pump P2, an air pump P3, syringe pumps SR1, SR2, SR4, a diluent chamber SC1, a hemolyzing agent chamber SC2, a waste liquid chamber WC, the diluent container 101, the waste liquid container 102, the hemolyzing agent container 103, air bubble sensors BS1, BS2, and valves SV1 to SV16, SV18 to SV20 and SV23 to SV 28 are connected by fluid supply tubes (flow paths). The syringe pumps SR1, SR4 are driven by a syringe pump motor STM4, and the syringe pump SR2 is driven by a syringe pump motor STM5. Stepping motors may be employed as the syringe pump motors STM4, STM5. The syringe pumps SR1, SR4 and the syringe pump motor STM4 are integrated as a syringe pump unit PU (see FIG. 48).

A preferred example of the diluent is CELLPACK available from Sysmex Corporation, and a preferred example of the hemolyzing agent is STROMATOLYSER WH available from Sysmex Corporation.

Figure 43:
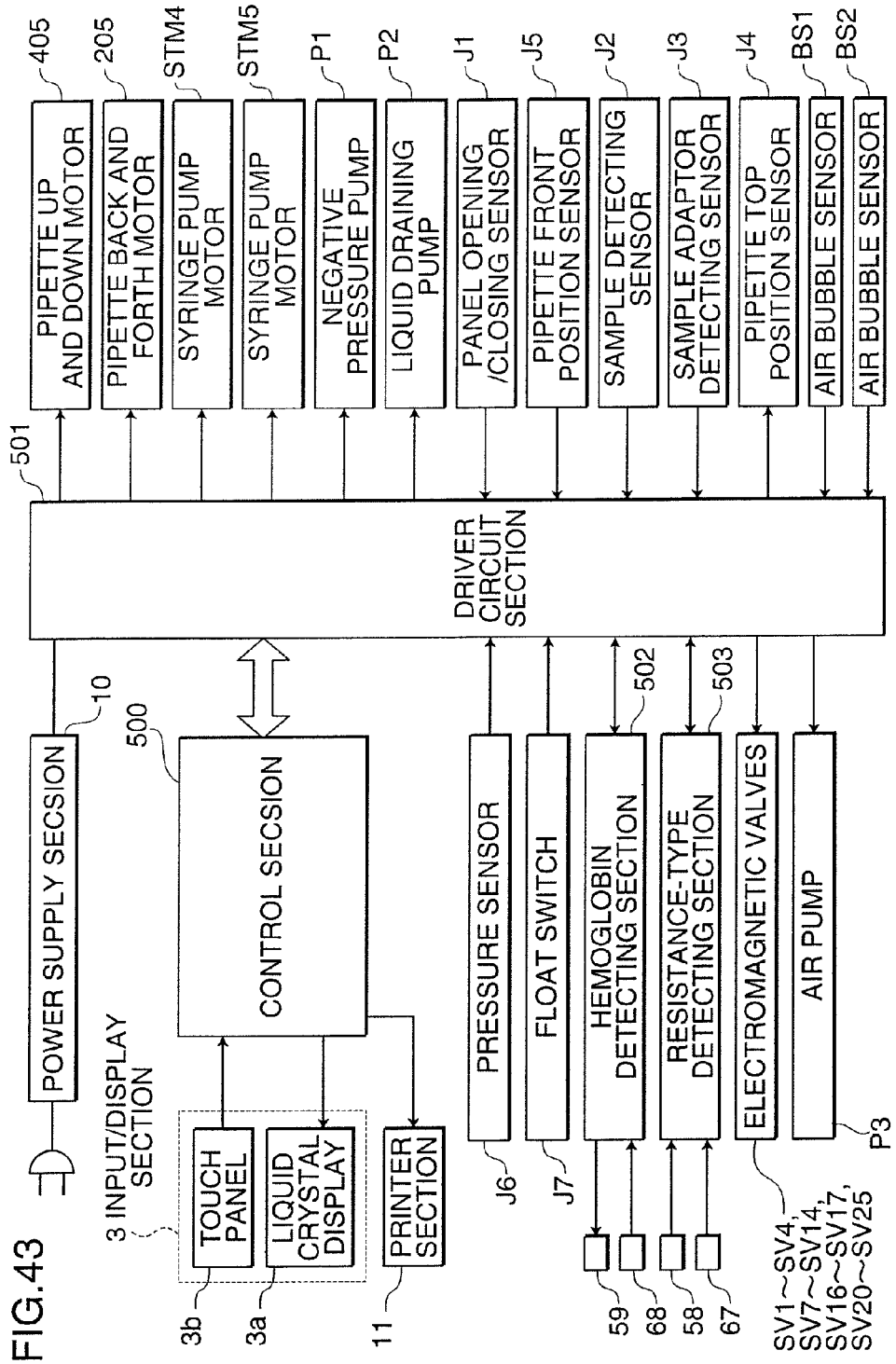
FIG. 43 is an electrical circuit diagram according to this invention.

FIG. 43 is a block diagram illustrating the electrical circuit according to the embodiment of the invention. The power supply section 10 transforms a voltage supplied from a commercial AC power supply into a DC voltage (12V), which is supplied to the control section 500 and the driver circuit section 501. The control section 500 is comprised of a microprocessor including a CPU, a ROM and a RAM, and the driver circuit section 501 includes driver circuits and I/O ports.

The driver circuit section 501 performs A-D conversion on output signals of the adaptor detecting sensor J1, the adaptor recognizing sensor J2, the pipette top position sensor J4, the pipette front position sensor J5, a pressure sensor J6 for detecting the negative pressure in the waste liquid chamber WC, a float switch J7 for detecting a liquid amount accumulated in the waste liquid chamber WC, the air bubble sensors BS1 and BS2, a hemoglobin detecting section 502 for allowing the light emitting diode 68 to emit light and for receiving an output from the photodiode 69, and a resistance-type detecting section 503 for detecting a change in impedance between the electrodes 58 and 67 through which a DC constant current passes, and outputs converted signals to the control section 500.

The control section 500 receives output signals from the driver circuit section 501 and output signals from the touch panel 3b, and processes these signals thus received according to a predetermined processing program. The control section 500 causes the driver circuit section 501 to drive the pipette up and down motor 405, the pipette back and forth motor 205, the syringe pump motors STM4, STM5, the negative pressure pump P1, the liquid draining pump P2, the air pump P3 and the electromagnetic valves SV1 to SV16, SV18 to SV20 and SV3 to SV28 on the basis of the results of the processing. Then, the control section 500 controls the liquid crystal display 3a of the display section 3 and the printer section 11 to display and print out analysis conditions, analysis items, analysis results and the like.

Analytic Operation to be Performed by Blood Analyzer

An analytic operation to be performed by the blood analyzer shown in FIG. 1 will hereinafter be described with reference to the fluid circuit shown in FIG. 42 and a flow chart shown in FIG. 44.

Figure 44:
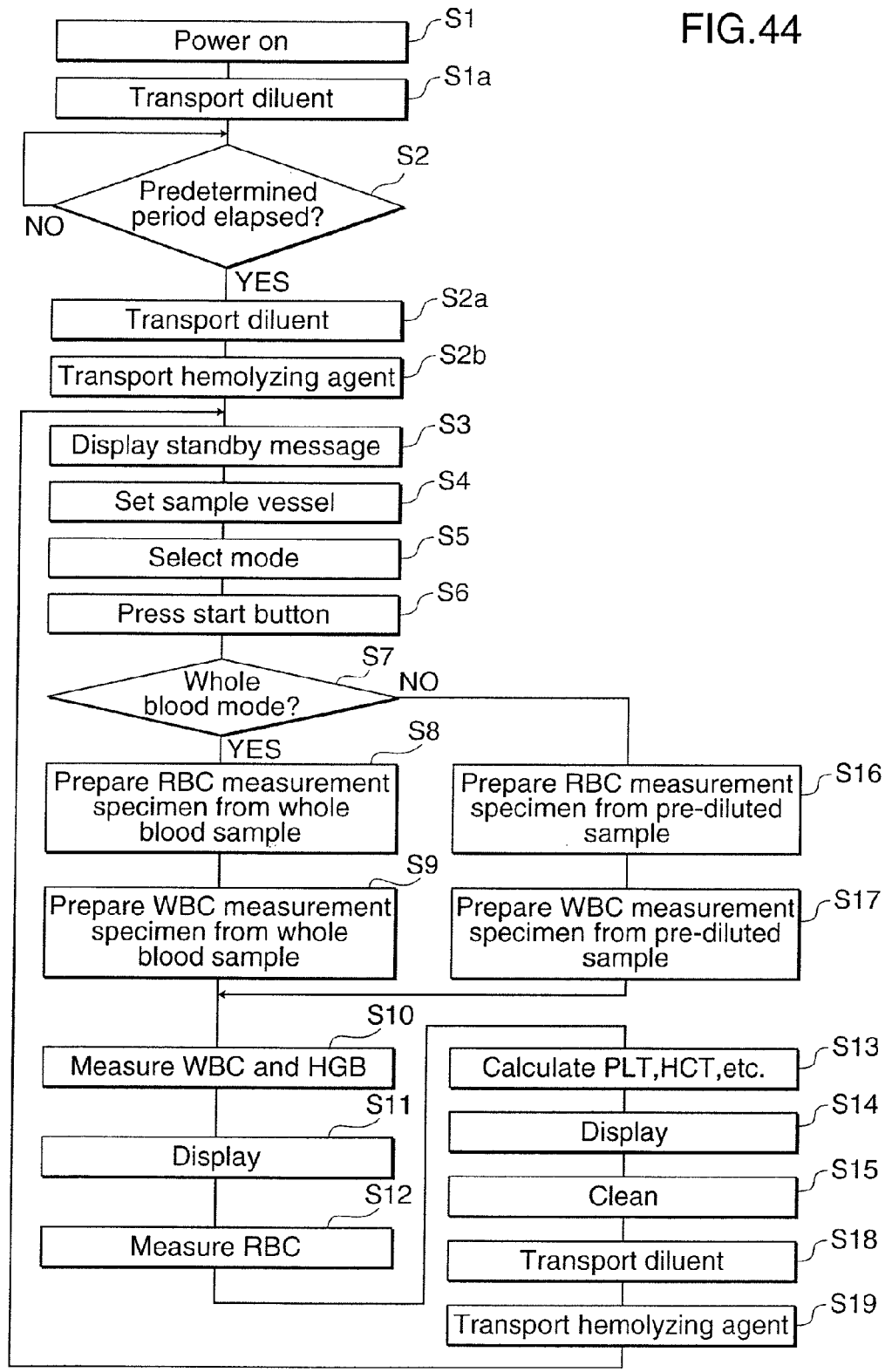
FIG. 44 is a flow chart illustrating the operation of the blood analyzer according to this invention.

As shown in FIG. 44, when the power supply to the blood analyzer is turned on (Step S1), a diluent required for preliminary cleaning is transported from the container 101 into the diluent chamber SC1 (Step S1a). Then, when a measurement preparation period required for preparatory operations for the analysis including the preliminary cleaning operation is elapsed (Step S2), the diluent and hemolyzing agent required for preparation of an analysis sample are transported from the containers 101 and 103 into the diluent camber SC1 and the hemolyzing agent chamber SC2, respectively (Steps S2a, S2b), and a message "Ready" is displayed on the liquid crystal display 3a of the display section 3.

Then, the user sets the sample vessel SP1 (or SP2, SP3) in the sample setting section 6 (FIG. 4) (Step S4). Where a sample in the sample vessel thus set is a whole blood sample, the user selects a whole blood mode by means of the touch panel 3b of the display section 3 and, where the sample is a diluted sample, the user selects a pre-diluted mode (Step S5).

Then, the user presses a start button on the touch panel 3b (Step S6). Where the sample vessel SP1 (or SP2, SP3) is not set and/or the sample setting panel 4 is not closed in Step S4, the sensor J1 detects such a situation, so that the analyzer does not operate. Where the sample vessel SP1 (or SP2, SP3) is set and the sample setting panel 4 is closed, the analyzer starts operating. Where the whole blood mode is selected (Step S7), a specimen for measurement of the number of red blood cells (RBC) and a specimen for measurement of the number of white blood cells (WBC) are prepared from the whole blood sample (Steps S8, S9).

With the use of the WBC measurement specimen prepared in Step S9, measurement of the WBC and the amount of hemoglobin (HGB) is performed (Step S10), and then the measured WBC and HGB are displayed on the liquid crystal display 3a (Step S11). Subsequently, measurement of the RBC is performed with the use of the RBC measurement specimen prepared in Step S8, and the number of platelets (PLT), a hematocrit value (HCT) and other analysis items are calculated. Then, the measured RBC and the calculated values for the respective analysis items are displayed on the liquid crystal display (Steps S13, S14).

The WBC, the RBC and the PLT are determined by counting pulses indicative of changes in impedance between the electrodes 58 and 67 of the detector 50. The HGB is determined by comparing the absorbance (blank level) of the diluent alone and the absorbance of the WBC measurement specimen measured by the photodiode 68. The HCT is determined on the basis of a maximum level of the pulses indicative of the changes in impedance between the electrodes 58 and 67, a mean corpuscular volume (MCV), a mean corpuscular hemoglobin (MCH) and a mean corpuscular hemoglobin concentration (MCHC) are calculated from the following expressions:

$$MCV=(HCT)/(RBC)$$

$$MCH=(HGB)/(RBC)$$

$$MCHC=(HGB)/(HCT)$$

Then, a fluid circuit cleaning operation is performed. Upon completion of the cleaning operation (Step S115), the diluent and the hemolyzing agent are transported from the containers 101 and 103 to the chambers SC1 and SC2, respectively on standby for the analysis of the next sample (Steps S18, S19), the routine returns to Step S3, and "Ready" is displayed on the liquid crystal display 3a on standby for the analysis of the next sample. Where the pre-diluted mode is selected in Step S7, the RBC measurement specimen and the WBC measurement specimen are prepared from a pre-diluted blood sample (Steps S16, S17). In this case, the pre-diluted sample is obtained by preliminarily diluting a whole blood sample. Therefore, a preliminary dilution factor should be taken into account so that the RBC measurement specimen and the WBC measurement specimen have the same dilution factors as those prepared from the whole blood sample in the whole blood mode.

Next, operations to be performed in FIG. 44 (Steps) will be described in detail with reference to the flow system diagram shown in FIG. 42. The analyzer is of a normally-closed valve type in which all the valves in the fluid circuit are usually closed.

Diluent Transporting Operation (Steps S1a, S2a, S18)

Figure 45:
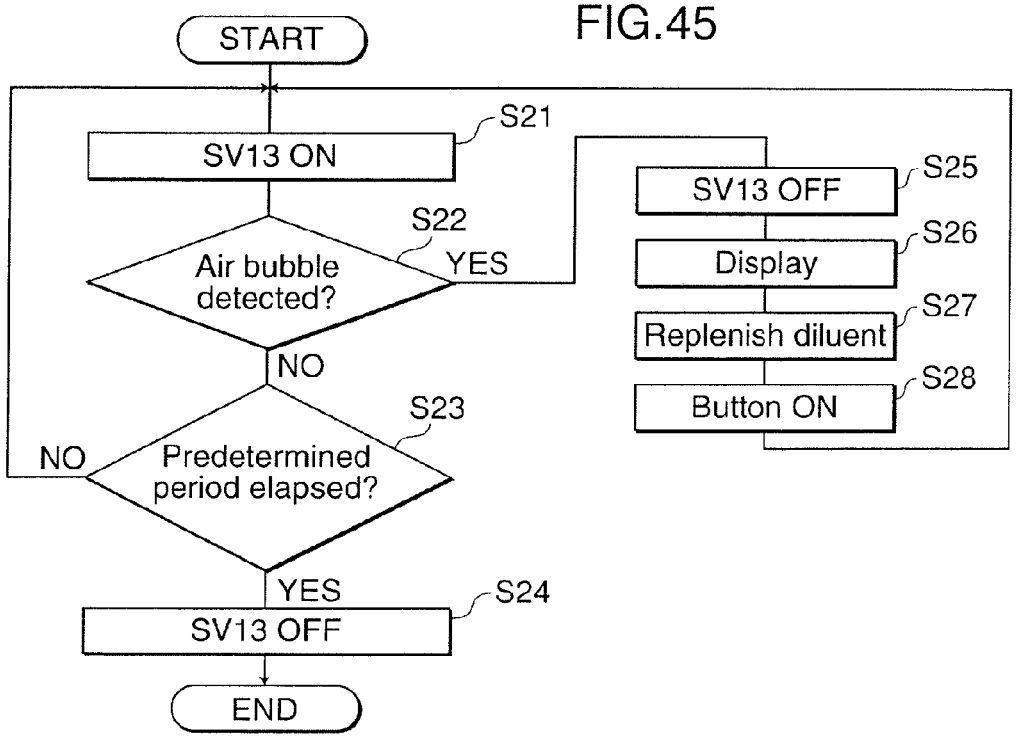
FIG. 45 is a flow chart illustrating the operation of the blood analyzer according to this invention.

As shown in the flow chart of FIG. 45, when the valve SV13 is opened (Step S21), a negative pressure is applied to the waste liquid chamber WC from the negative pressure pump P1. Whereby, the diluent is supplied into the diluent chamber SC1 from the diluent container 101 through the air bubble sensor BS1. Where the air bubble sensor BS1 does not detect more than a predetermined amount of air bubbles in a flow path (Step S22), the valve S13 is closed after the lapse of a predetermined time period (Steps S23, S24). Thus, a predetermined amount of the diluent is stored in the diluent chamber SC1.

On the other hand, where the air bubble sensor BS1 detects more than the predetermined amount of the air bubbles in the flow path in Steps S22, the control section 500 judges that no diluent is present in the diluent container 101. The valve 13 is thereafter closed, and the display section 3 displays the judgment on the display 3a (Steps S25, S26).

The user replenishes the diluent container 101 with the diluent or replaces the diluent container 101 with a new one (Step S27), and presses a "diluent replenishing completion" button on the touch panel 3b of the display section 3 (Step S28). Whereby, the routine returns to Step S21.

Hemolyzing Agent Transporting Operation (Steps S2b, S19)

Figure 46:
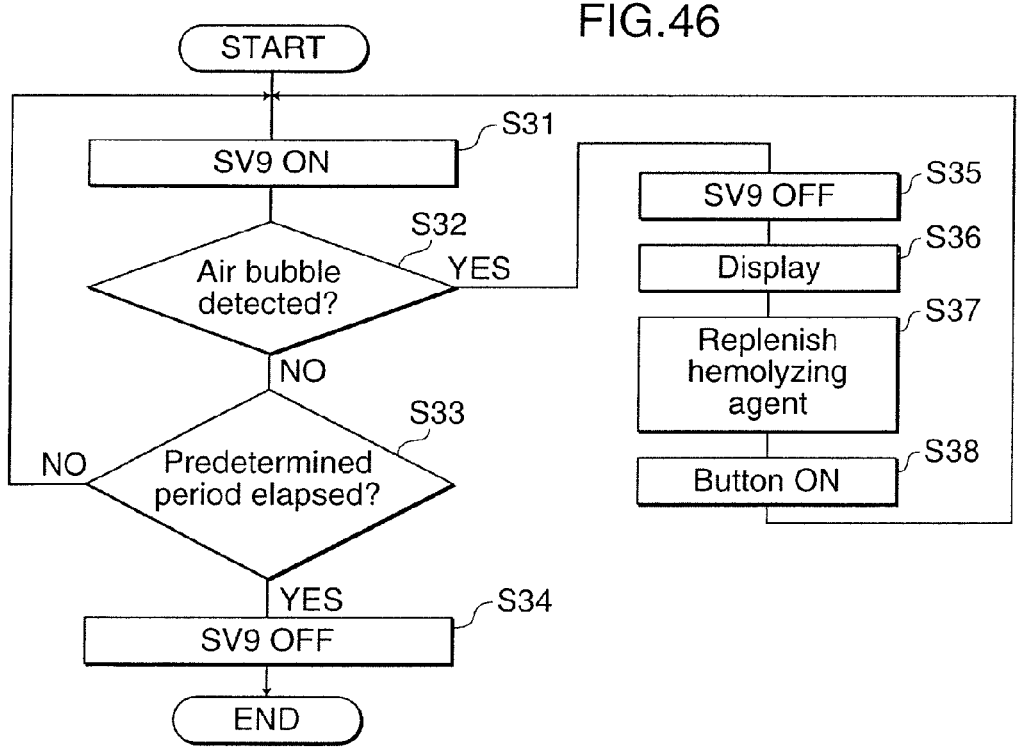
FIG. 46 is a flow chart illustrating the operation of the blood analyzer according to this invention.

As shown in the flow chart of FIG. 46, when the valve SV9 is opened (Step S31), a negative pressure is applied to the waste liquid chamber WC from the negative pressure pump P1, whereby the hemolyzing agent is supplied into the hemolyzing chamber SC2 from the hemolyzing container 103 through the air bubble sensor BS2. Where the air bubble sensor BS2 does not detect more than a predetermined amount of air bubbles in a flow path (Step S32), the valve SV9 is closed after the lapse of a predetermined time period (Steps S33, S34). Thus, a predetermined amount of the hemolyzing agent is stored in the hemolyzing agent chamber SC2.

On the other hand, where the air bubble BS2 detects more than the predetermined amount of the air bubbles in the flow path in Step S32, the control section 500 judges that no hemolyzing agent is present in the hemolyzing agent container 103. The valve SV9 is thereafter closed, and the display section 3 displays the judgment the hemolyzing agent on the display 3a (Steps S35, S36).

The user replenishes the hemolyzing agent container 103 with the hemolyzing agent or replaces the hemolyzing agent container 103 with a new one (Step S37), and presses a "hemolyzing agent replenishing completion" button on the touch panel 3b of the display section 3 (Step S38). Whereby, the routine returns to Step S31. Incidentally, the diluent transporting operation (Steps S1a, S2a, S18) and the hemolyzing agent transporting operation (Steps S2b, S19) are not simultaneously performed. That is, either of the operations is performed.

Preliminary Cleaning Operation (Step S2)

(1) The pipette PT is moved to the upper side of the sample rack 18, and then lowered as shown in FIG. 22. (At this time, the sample vessel SP1 is not set in the sample setting section 6.) Then, the valve SV19 is opened to suck the diluent from the diluent chamber SC1 into the syringe pump SR2, and the valve SV19 is closed.

(2) The valves SV4, SV11, SV20 are opened, and the diluent is supplied into the cleaner S from the syringe pump SR2 and then drained into the waste liquid chamber WC. At the same time, the pipette PT is lifted, and the cleaning of the exterior of the pipette PT is performed. When the tip of the pipette PT is inserted into the main body 80 of the cleaner S, the pipette PT is stopped. Thus, the cleaning of the exterior of the pipette PT is completed.

(3) With the valves SV4, SV11, SV20 kept open, the pipette PT is held at the position shown in FIG. 32. Then, the valves SV7 is opened, and the diluent is supplied into the pipette PT from the syringe pump SR2 through the syringe pump SR1. At the same time, the diluent discharged from the suction port 32 of the pipette PT is drained into the waste liquid chamber WC for cleaning the interior of the pipette PT.

(4) When the valves SV7 is closed, the flow of the diluent from the suction port 32 of the pipette PT to the first opening 85a is stopped, whereby the interior cleaning is completed. At this time, the suction flow path 31 and the suction port 32 are filled with the diluent. On the other hand, the flow of the diluent from the second opening 85b to the first opening 85a is continued and, when the valves SV4, SV11, SV20 are closed, the flow is stopped. Therefore, the suction port 32 of the pipette PT is kept filled with the diluent.

Preparation of RBC Measurement Specimen (Step S8)

(1) A negative pressure is applied to the waste liquid chamber WC from the negative pressure pump P1, and the valves SV14, SV10 are opened, whereby residual liquid is expelled from the detector 50 and the mixing chamber 70. Thereafter, the valves SV14, SV10 are closed.

(2) The valve SV19 is opened, and the syringe pump SR2 is operated for suction, whereby the diluent is sucked into the syringe pump SR2 from the diluent chamber SC1. Then, the valve SV19 is closed.

(3) The pipette PT is lowered to be inserted into the sample vessel SP1 (FIG. 22). Then, the syringe pump SR1 is operated for suction, whereby the pipette PT sucks a predetermined amount (10 μL) of the blood sample.

(4) Then, the pipette PT is lifted. During the lifting, the valves SV4, SV20, SV11 are opened, whereby the diluent is supplied into the cleaner S from the syringe pump SR2 and drained into the waste liquid chamber WC for cleaning the exterior of the pipette PT. Then, the valves SV4, SV20, SV11 are closed.

(5) The valves SV16, SV20 are opened, and the syringe pump SR2 is operated for discharge, whereby a predetermined amount (1.3 mL) of the diluent is supplied into the mixing chamber 70. Then, the valves SV16, SV20 are closed.

(6) The pipette PT is moved to a position just above the mixing chamber 70, and lowered. Then, the syringe pump SR1 is operated for discharge, whereby the 10-μL blood sample preliminarily sucked into the pipette PT is discharged into the mixing chamber 70. Thus, the blood sample is diluted 130 times in the mixing chamber 70 through first-stage dilution, so that a 1.3-mL diluted sample is prepared in the mixing chamber 70.

(7) While the exterior of the pipette PT is cleaned as described above, the pipette PT is lifted. When the tip of the pipette PT is inserted into the main body 80 of the cleaner S, the valves SV7, SV20, SV11 are opened. Thereafter, the diluent is supplied into the pipette PT from the syringe pump SR2 through the syringe pump SR1 and drained into the waste liquid chamber WC from the tip of the pipette PT for cleaning the interior (inner surface) of the pipette PT. Then, the valves SV11, SV7, SV20 are closed.

(8) The valve SV6 is opened, and the air pump P3 is driven to supply air into the mixing chamber 70, whereby the diluted sample is agitated in the mixing chamber 70 by air bubbles. Then, the air pump P3 is stopped and the valve SV6 is closed.

(9) The pipette PT is lowered again into the mixing chamber 70. Then, the valves SV7, SV20 are opened, and the syringe pump SR2 is operated for suction, whereby a predetermined amount (0.59 mL) of the first-stage diluted sample is sucked into the pipette PT. Then, the valves SV7, SV20 are closed. Here, the diluent supplied from the syringe pump SR2 into the pipette PT passes through the syringe pump SR1. When the syringe pump SR2 is operated for suction and discharge of the diluent in the pipette PT, the diluent passes through the syringe pump SR1. The same step is performed for all procedures described below.

(10) While the exterior of the pipette PT is cleaned as in Step (2) of the preliminary cleaning operation, the pipette PT is lifted.

(11) The valve SV14 is opened. Then, a negative pressure is applied to the waste liquid chamber WC from the negative pressure pump P1, whereby the residual sample in the mixing chamber 70 is drained into the waste liquid chamber WC. Then, the valve SV14 is closed.

(12) The valves SV16, SV20 are opened, and the syringe pump SR2 is operated for discharge, whereby the diluent is supplied into the mixing chamber 70 from the syringe pump SR2. Thereafter, the valves SV16, SV20 are closed. Then, the above Step (11) is performed again. Thus, the mixing chamber 70 is cleaned.

(13) The valves SV16, SV20 are opened, and the syringe pump SR2 is operated for discharge, whereby a predetermined amount of the diluent is preliminarily dispensed in the mixing chamber 70 from the syringe pump SR2. Then, the valves SV16, SV20 are closed.

(14) The pipette PT is lowered. Then, the valves SV7, SV20 are opened, and the syringe pump SR2 is operated for discharge, whereby 0.2 mL out of the 0.59-mL first-stage diluted sample retained in the pipette PT is discharged into the mixing chamber 70. Then, the valves SV7, SV20 are closed. Thereafter, the pipette PT is lifted. During the lifting, the exterior of the pipette PT is cleaned in the aforesaid manner.

(15) The valves SV16, SV20 are opened, and the syringe pump SR2 is operated for discharge, whereby the diluent is supplied into the mixing chamber 70 from the syringe pump SR2 for diluting the sample 750 times for second-stage dilution. Thus, a second-stage diluted sample is prepared. Then, the valves SV16, SV20 are closed. At this time, the second-stage diluted sample is agitated by air bubbles in the aforesaid manner.

Thus, the RBC measurement specimen is prepared in the mixing chamber 70.

Preparation of WBC Measurement Specimen (Step S9)

(1) The valve SV19 is opened, the diluent is sucked into the syringe pump SR2 from the diluent chamber SC1, and the valve SV19 is closed. Then, the valves SV20, SV27, SV28 are opened to cause the syringe pump SR2 to suck 0.02-mL air. Thereafter, the valves SV20, SV27, SV28 are closed. Flow paths are preliminary filled with the diluent.

The valves SV20, SV26, SV27 are opened, and the syringe pump SR2 is operated for suction, whereby the hemolyzing agent is sucked into a charging line CL1 from the hemolyzing agent chamber SC2 and retained in the charging line CL1. At this time, the suction amount of the syringe pump SR2 is determined so that the amount of the hemolyzing agent retained in the flow paths including the charging line CL1 becomes 0.5 mL. Then, the valve SV26 is closed.

The valve SV25 is opened, and the syringe pump SR2 is operated for discharge, whereby 1.02 mL of fluid including 0.5 mL of the diluent, 0.5 mL of the hemolyzing agent and 0.02 mL of the air is discharged into the detector 50 via a nozzle 61. Then, the valves SV20, SV25, SV27 are closed.

(2) The pipette PT is moved to the upper side of the detector 50, and lowered. Then, the valves SV7, SV20 are opened, and the syringe pump SR2 is operated for discharge, whereby 0.39 mL of the first-stage diluted sample is discharged into the detector 50 from the pipette PT. Then, the valves SV7, SV20 are closed.

Thus, 0.5 mL of the diluent, 0.39 mL of the first-stage diluted sample and 0.5 mL of the hemolyzing agent are present in the first and third containers 51, 53 of the detector 50.

(3) The pipette PT is lifted, and the exterior and interior of the pipette PT are cleaned in the aforesaid manner.

(4) The valve SV5 is opened, and the air pump P3 is operated to supply air into the detector 50 for agitation with air bubbles. Then, the air pump P3 is stopped, and the valve SV5 is closed. Thus, the preparation of the WBC measurement specimen in the first and third containers 51, 53 of the detector 50 is completed.

Measurement of WBC and HGB (Step S10)

(1) The valves SV18, SV23 are opened. Then, a negative pressure is applied to the waste liquid chamber WC from the negative pressure pump P1, whereby the diluent is caused to flow from the diluent chamber SC1 to the waste liquid chamber WC through the second container chamber 52 of the detector 50. Thus, the second container chamber 52 is cleaned, and the diluent is retained in the second container chamber 52. Then, the valves SV18, SV23 are closed.

(2) The valve SV24 is opened, and the syringe pump SR2 is operated for suction, whereby the WBC measurement specimen is caused to flow from the first and third container chambers 51, 53 into the second container chamber 52 via the orifice 55 in the detector 50 (for about 10 seconds). Then, the valve SV24 is closed. At this time, the resistance-type detecting section 503 detects changes in impedance between the electrodes 58 and 67, and the control section 500 calculates the number of the white blood cells (WBC) on the basis of the detection result.

(3) At the same time, light emitted from the light emitting diode 68 is transmitted through the specimen, and the intensity of the transmitted light of the third container chamber 53 is detected by the photodiode 69. The control section 500 calculates the amount of the hemoglobin (HGB) on the basis of the detected light intensity. The blank measurement of the HGB (measurement of the intensity of light transmitted through the diluent) is performed immediately after Step (1) of the WBC measurement specimen preparing operation.

Measurement of RBC (Step S12)

(1) The valve SV10 is opened, and a negative pressure is applied to the waste liquid chamber WC from the negative pressure pump P1, whereby residual liquid in the detector 50 is drained into the waste liquid chamber WC. Then, the valve SV10 is closed.

(2) The valves SV15, SV20 are opened, and the syringe pump SR2 is operated for discharge, whereby the diluent is supplied into the first and third container chambers 51, 53 via the nozzle 60 of the detector 50. Then, the valves SV15, SV20 are closed.

(3) The valves SV18, SV23 are opened, and a negative pressure is applied to the waste liquid chamber WC from the negative pressure pump P1, whereby the diluent is supplied from the diluent chamber SC1 into the second container chamber 52 of the detector 50 for cleaning the second container chamber 52. Then, the valves SV18, SV23 are closed.

(4) The valves SV1, SV12, SV20 are opened, and the syringe pump SR2 is operated for suction, whereby the RBC measurement specimen is sucked from the mixing chamber 70 into a charging line CL2 and retained in the charging line CL2. Then, the valves SV1, SV12, SV20 are closed.

(5) The valve SV24 is opened, and the syringe pump SR2 is operated for discharge, whereby the diluent flows from the third container chamber 52 into the first container chamber 51 through the orifice 55 in the detector 50.

(6) During this period, the syringe pump SR4 is operated for discharge, whereby the RBC measurement specimen retained in the charging line CL2 is ejected from the jet nozzle 56 toward the orifice 55. The RBC measurement specimen ejected from the jet nozzle 56 is surrounded by the diluent in the preceding Step (5), and passes as a sheath flow through the orifice 55 (for about 10 seconds). Then, the valve SV24 is closed.

(7) The control section 500 calculates the number of the red blood cells (RBC), the number of the platelets (PLT), the hematocrit (HCT) and other analysis items on the basis of changes in impedance between the electrodes 58 and 67 when the sheath flow passes through the orifice 55.

Cleaning Operation (Step S15)

(1) The valves SV10, SV14 are opened, and then a negative pressure is applied to the waste liquid chamber WC from the negative pressure pump P1, whereby residual liquid in the mixing chamber 70 and the detector 50 is drained into the waste liquid chamber WC. Then, the valves SV10, SV14 are closed.

(2) The valves SV15, SV16, SV20 are opened, and the syringe pump SR2 is operated for discharge, whereby the diluent is supplied into the mixing chamber 70 and the detector 50. Then, the valves SV15, SV16, SV20 are closed.

(3) The valves SV1, SV2 are opened, and then a negative pressure is applied to the waste liquid chamber WC from the negative pressure pump P1, whereby the diluent is drained from the mixing chamber 70 into the waste liquid chamber WC through the charging line CL2. Then, the valves SV1, SV2 are closed.

Thus, the cleaning operation is completed. The negative pressure in the waste liquid chamber WC is monitored by the pressure sensor J6, and the negative pressure pump P1 is driven to constantly keep the pressure within a range between 100 and 300 mmHg, preferably between 150 and 200 mmHg.

When the amount of the waste liquid stored in the waste liquid chamber WC reaches a predetermined amount, this situation is detected by the float switch J7, and the liquid draining pump P2 is driven by the float switch J7, whereby the waste liquid is drained into the waste liquid container 102.

Characteristics of Liquid Transfer

Figure 47:
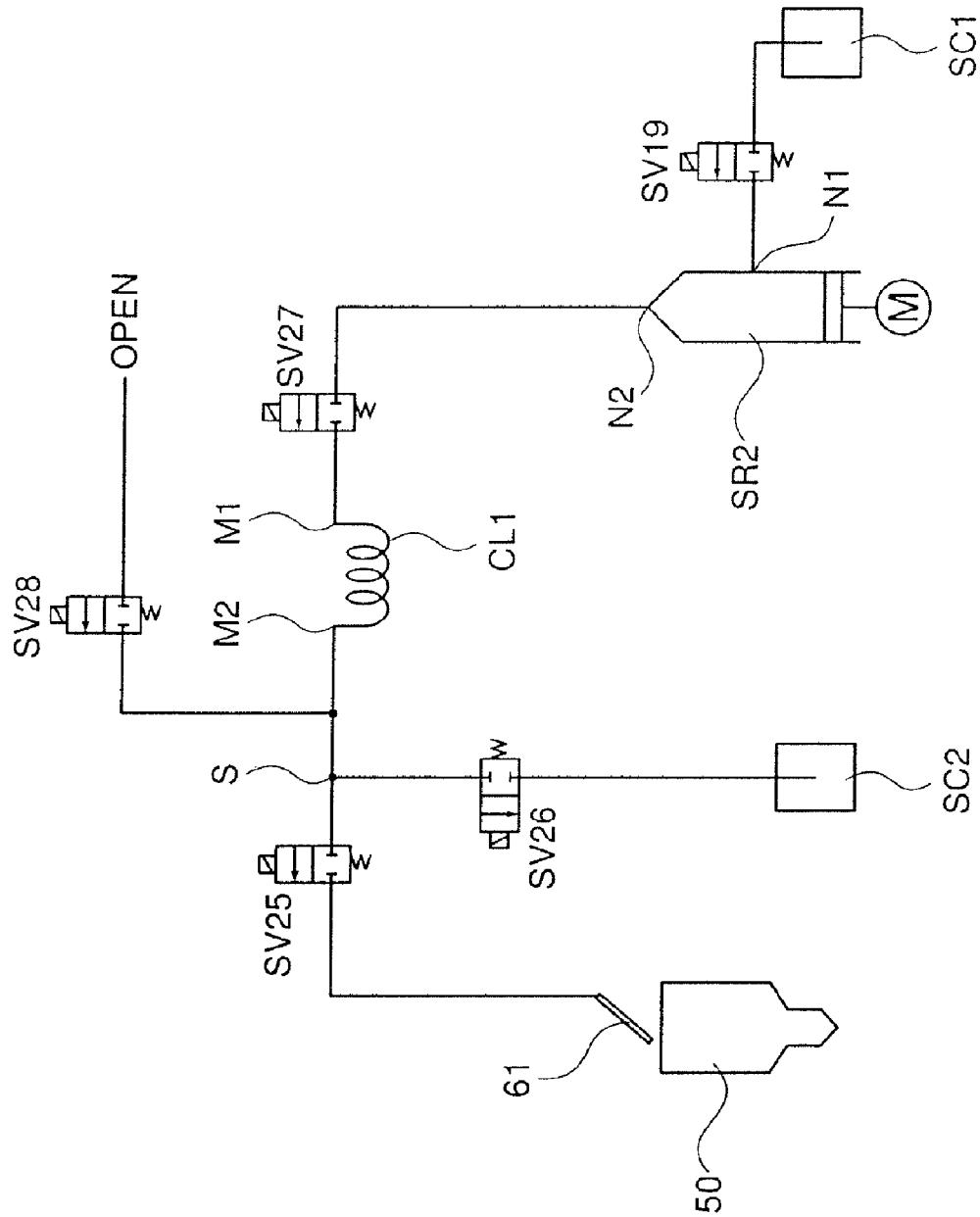
FIG. 47 is a detailed diagram of major portions of the fluid circuit according to this invention.

FIG. 47 is a detailed diagram of a major portion of the fluid circuit shown in FIG. 42.

As shown, the fluid circuit includes a tube-shaped third retaining portion (charging line) CL1 with a first opening M1 and a second opening M2 provided at both ends thereof, a liquid discharge portion (nozzle) 61, a single syringe pimp SR2 having a first suction port N1 and a second suction and discharge port N2, a first retaining portion (diluent chamber) SC1 for storing a first liquid (diluent), and a second retaining portion (hemolyzing agent chamber) SC2 for storing a second liquid (hemolyzing agent).

Opening/closing valves SV19, SV27, SV26 and SV25 are respectively provided between the first retaining SC1 and the first suction port N1, between the first opening M1 and the second suction and discharge port N2, between the second retaining portion SC2 and the second opening M2, and between the second opening M2 and the liquid discharge section 61, which are connected via flow paths.

Further, an opening/closing valve SV28 for communicating with the atmosphere is connected to the second opening M2 through the flow paths. The flow paths are preliminarily filled with the first liquid (i.e., the diluent).

In this arrangement, the following steps are performed:

(1) The valve SV19 is first opened, and the diluent is sucked into the syringe pump SR2 from the diluent chamber SC1. Then, the valve SV19 is closed.

(2) Next, the valves SV28, SV27 are opened, and the syringe pump SR2 is operated for suction, whereby a predetermined volume (20 μL) of air is sucked into the flow path to provide an air layer in the third retaining portion (the charging line) CL1. Thereafter, the valve SV28 is closed.

(3) The valve SV26 is opened, and the syringe pump SR2 is operated for suction. Whereby, a predetermined amount (0.5 mL) of the hemolyzing agent is sucked from the hemolyzing agent chamber SC2 into the flow path between the point S and the second opening M2 and the charging line CL1. Then, the valve SV26 is closed.

(4) The valve SV25 is opened, and the syringe pump SR2 is operated for discharge, whereby 0.5 mL of the diluent, 0.5 mL of the hemolyzing agent and 0.02 mL of the air are discharged into the detector 50 via the nozzle 61. Then, all the valves are closed.

With this arrangement, two kinds of liquids such as the diluent and the hemolyzing agent can be quantitatively dispensed by the single syringe pump SR2.

The air layer provided in the flow paths prevents the diluent between the syringe pump SR2 and the charging line CL1 from being mixed with the hemolyzing agent.

In this embodiment, the liquid is discharged into the upper-open detector 50 via the nozzle 61, but may be discharged into a closed detector or chamber via a nipple (liquid discharge portion).

Construction of Syringe Pump Unit

Figure 48:
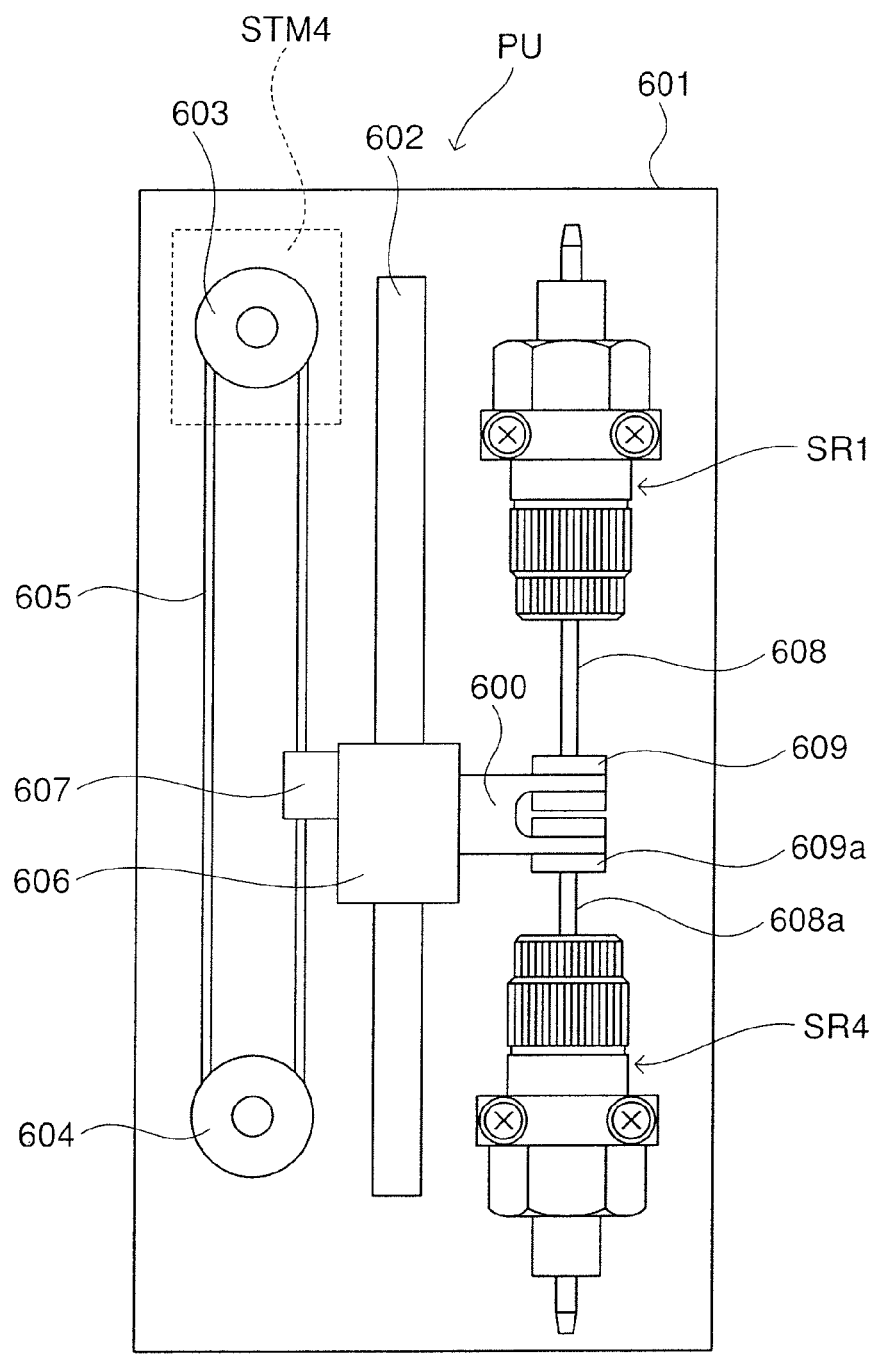
FIG. 48 is a front view of a syringe pump unit according to this invention.

FIG. 48 is a front view of a syringe pump unit PU shown in FIG. 42.

As shown, the syringe pumps SR1, SR4 to be paired are fixed in line to a support plate 601 so as to be opposed to each other. A sliding rail 602 is provided on the support plate 601 parallel to the syringe pumps SR1, SR4, and a driving pulley 603 and a driven pulley 604 are rotatably provided on upper and lower portions of the support plate 601, respectively.

A syringe pump motor STM4 provided on the rear side of the support plate 603 causes the driving pulley 603 to be rotatably driven. A timing belt 605 is stretched between the pulleys 603 and 604. The sliding rail 602 supports a sliding member 606 in a slidable manner. The sliding member 606 is coupled with the timing belt 605 via a coupling member 607 thereby to be moved vertically up and down by the syringe pump motor STM4.

Pistons 608, 608a of the syringe pumps SR1, SR2 respectively have terminals 609, 609a provided at their distal ends. The terminals 609, 609a are connected to each other by means of the engaging member 600, and the engaging member 600 is connected to the sliding member 606. When the syringe pump motor STM4 is driven, the pistons 608, 608a cooperate to move vertically up and down.

Figure 49:
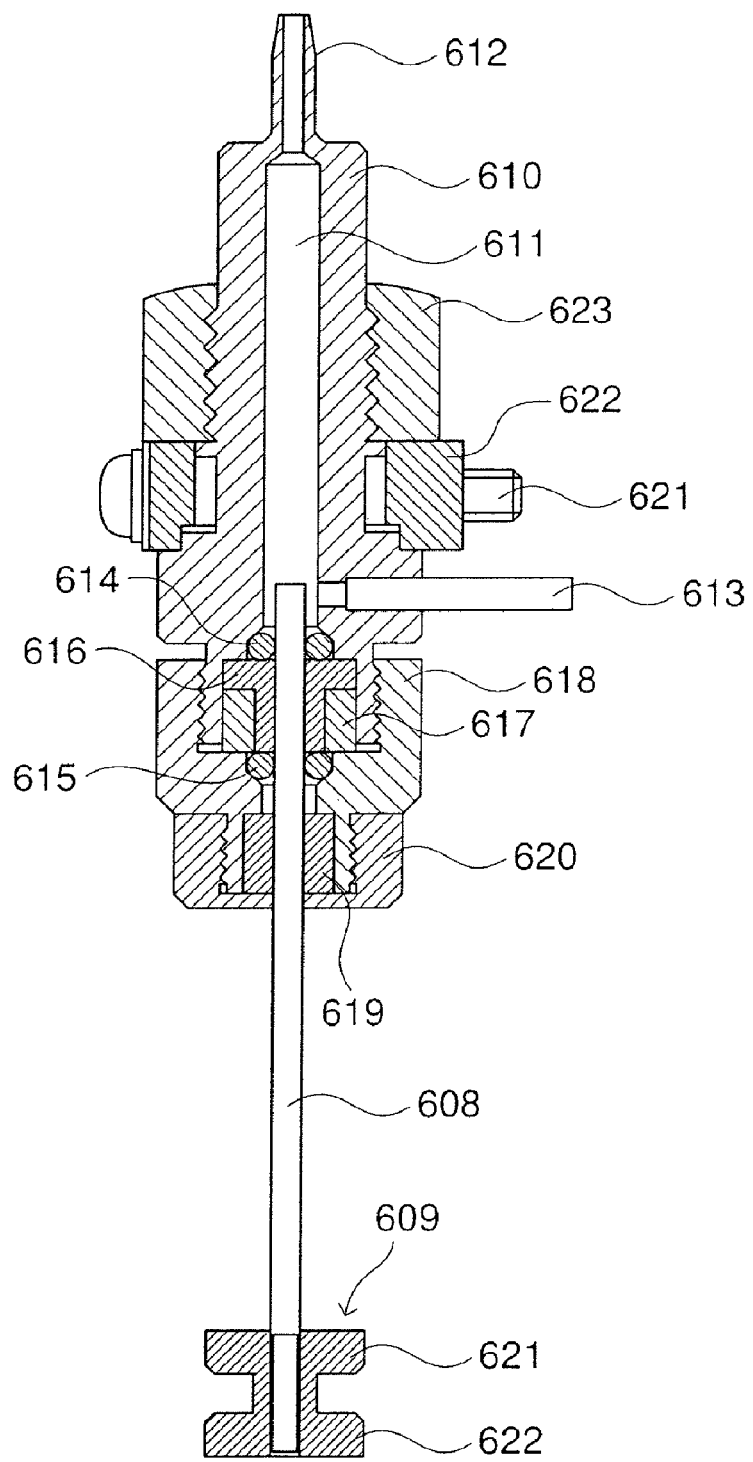
FIG. 49 is a vertical sectional view of a syringe pump according to this invention.

FIG. 49 is a vertical sectional view of a syringe pump SR1. The syringe pump SR2 has substantially the same construction as the syringe pump SR1. As shown, the piston 608 extends from a lower end portion of a cylinder 610 with a cylindrical hollow portion 611 provided therein, and can vertically be inserted into the hollow portion 611. A suction and discharge nipple 612 is provided at an upper end of the cylinder 610 for communicating with the hollow portion 611, and another suction and discharge nipple 613 is provided in the vicinity of a lower end of the cylinder 610 for communicating with the hollow portion 611.

O-rings 614, 615, a seal 616 and a collar 617 employed for sealing a gap between the piston 608 and the hollow portion 611 are fixed to a lower end portion of the cylinder 610 by a cap 618 with inside screws. A cleaning member (sponge) 619 for cleaning an outer surface of the piston 608 is fixed to the cap 618 by means of a cap 620.

In the syringe pump SR1, a liquid is sucked through the nipples 612 and 613 into the hollow portion 611 after the lowering of the piston 608, and the sucked liquid is discharged through the nipples 612 and 613 after the lifting of the piston 608. On the contrary, the syringe pump SR4 is operated for discharge and suction in a reversed manner.

Each of the syringe pumps SR1 and SR2 serves as one flow path because the nipples 612 respectively communicate with the nipples 613 through the hollow portions 611. The syringe pump SR1 is fastened to a fixing portion 622 by a nut 623. The fixing portion 622 is preliminarily fixed to the support plate 601 by a screw 621.

Figure 50:
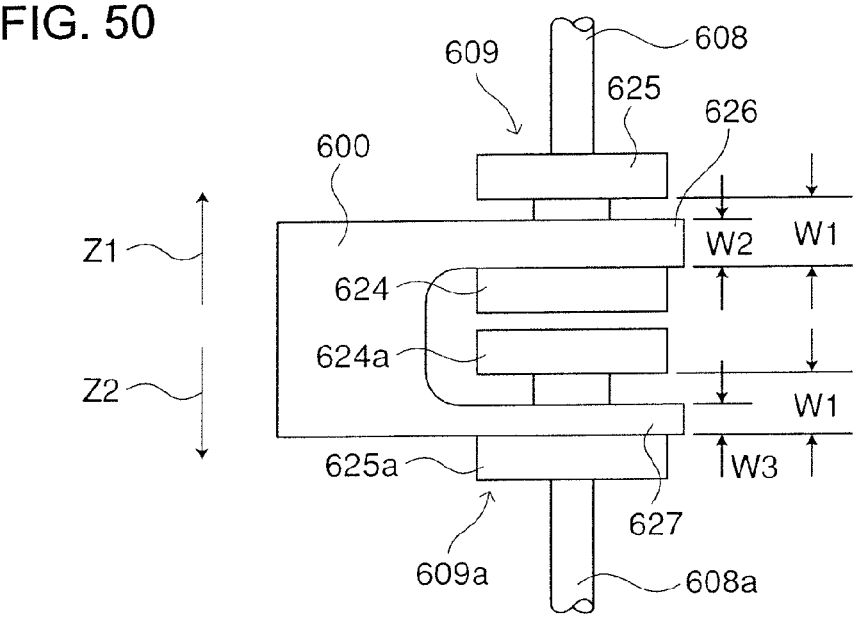
FIG. 50 is a diagram for explaining the operation of major portions of the syringe pump unit shown in FIG. 48.
Figure 51:
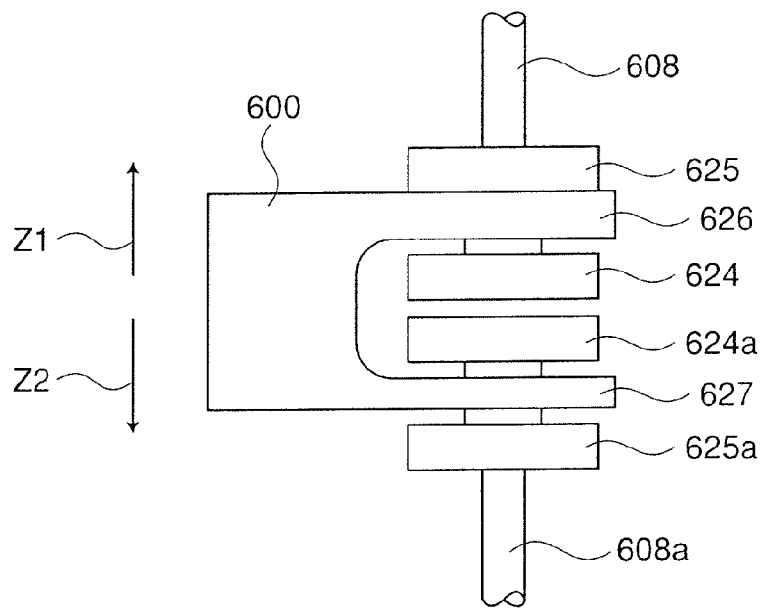
FIG. 51 is a diagram for explaining the operation of the major portions of the syringe pump unit shown in FIG. 48.
Figure 52:
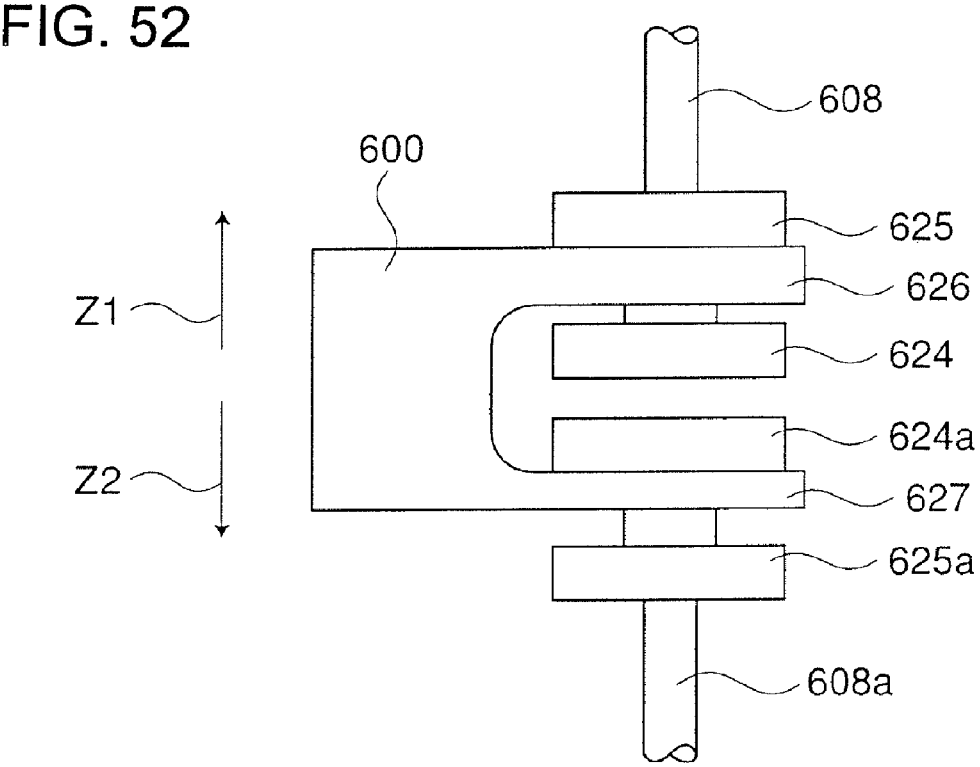
FIG. 52 is a diagram for explaining the operation of the major portions of the syringe pump unit shown in FIG. 48.

FIGS. 50 to 52 are diagrams for explaining an engaging relationship between the terminals 609, 609a of the syringe pumps SR1, SR2 and the engaging member 600.

As shown in FIG. 50, the terminal 609 fixed to the distal end of the piston 608 includes a pair of flanges 624, 625, and the terminal 609a fixed to the distal end of the piston 608a includes a pair of flanges 624a, 625a. The flanges 624, 625 are provided at an interval W1, and the flanges 624a, 625a are also provided at an interval W1.

The engaging member 600 has fingers 626, 627 with their widths W2, W3, respectively. The fingers 626, 627 are respectively inserted between the flanges 624, 625 and between the flanges 624a, 625a.

W1, W2 and W3 have a relationship of W1>W2>W3, for example, W1=2.5 mm, W2=2.4 mm and W3=2.0 mm.

In this arrangement, when the engaging member 600 is moved in an arrow direction Z1, the finger 626 is first brought into contact with the flange 625 as shown in FIG. 51 thereby to drive the piston 608 in the arrow direction Z1, and then the finger 627 is brought into contact with the flange 624a as shown in FIG. 52 thereby to drive the piston 608a in the arrow direction Z1. Accordingly, the engaging member 600 is driven in the arrow direction Z1 in association with the movement of the pistons 608, 608a.

In the state shown in FIG. 52, when the engaging member 600 is moved in an arrow direction Z2, the finger 626 is first brought into contact with the flange 624 thereby to drive the piston 608 in the arrow direction Z2, and then the finger 627 is brought into contact with the flange 625a thereby to drive the piston 608a in the arrow direction Z2. Accordingly, the engaging member 600 is driven in the arrow direction Z2 in association with the movement of the pistons 608, 608a.

Thus, the engaging member 600 and the terminals 609, 609a transmit a driving force supplied from the syringe pump motor STM4 to the pistons 608, 608a with a time lag between the pistons, and then the pistons 608, 608a start driving vertically.

Therefore, the syringe pump motor STM4 is prevented from being heavily loaded simultaneously by static friction between the pistons 608, 608a and the cylinders, so that the syringe pump motor STM4 can be operated at a reduced capacity. The terminals 609, 609a are not necessarily required to be fixed to the distal ends of the pistons 608, 608a, respectively, but may be fixed at some midpoints of the pistons 608, 608a.

Further, the pistons 608, 608a are not necessarily required to be provided in line, but may be provided parallel to each other so that the axis of the piston 608 is offset from that of the piston 608a.

Still further, the fingers 626 and 627 of the engaging member 600 may be respectively set to have the same widths W2 and W3, and the interval W1 between the flanges 624 and 625 may be smaller than that between the flanges 624a and 625a.

Constructions of Air Bubble Sensors BS1, BS2

Figure 53:
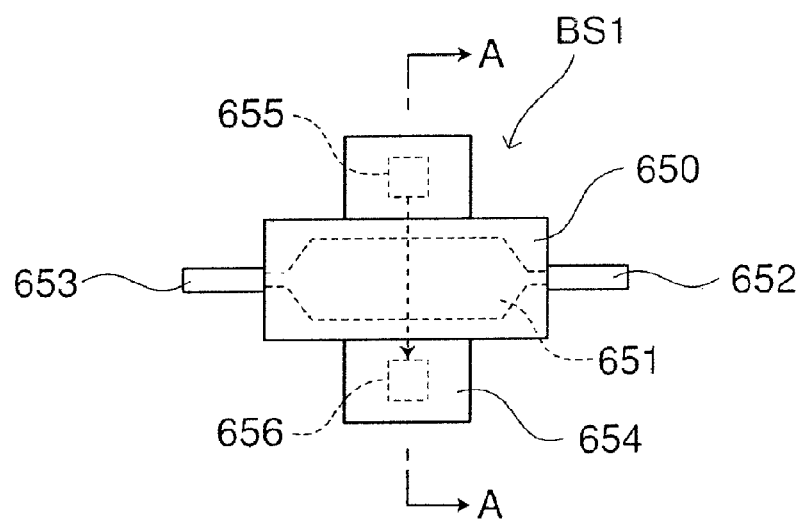
FIG. 53 is a top surface view of an air bubble sensor according to this invention.
Figure 54:
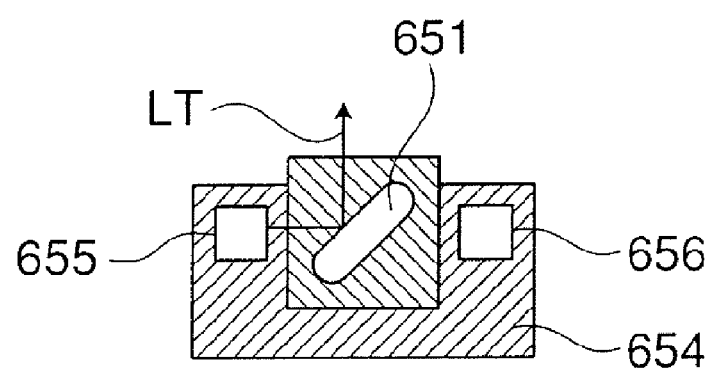
FIG. 54 is a view from an A-A arrow direction in FIG. 53.

FIG. 53 is a top surface view of an air bubble sensor BS1, and FIG. 54 is a view from an A-A arrow direction in FIG. 53.

As shown, the air bubble sensor BS1 is comprised of a main body 650 composed of a transparent resin such as a polyether imide, a flow path 651 having an oblong shape in section provided in the main body 650, and nipples 652, 653 connected to both ends of the flow path 651. The main body 650 is integrated with a photo-interrupter 654 as shown in FIGS. 53 and 54. The photo-interrupter 654 includes a light emitting element (for example, a LED) 655 and a photo-receptive element 656 (for example, a photodiode). An air bubble sensor BS2 has substantially the same construction as the air bubble sensor BS1.

When light LT is emitted from the light emitting element 655 to the empty flow path 651, the light LT incident at an angle of 45 degrees is totally reflected at a wall of the empty flow path 651 as shown in FIG. 54. Accordingly, the light LT does not reach the photo-receptive element 656. On the other hand, when light LT is emitted from the light emitting element 655 to the flow path 651 filled with a liquid, the light LT passes through the wall of the flow path 651 to reach the photo-receptive element 656 because of the refraction of the light LT with respect to the liquid.

An output from the photo-receptive element 656 is converted to a logic signal (binary signal) of "1" or "2" by a conversion circuit (not shown) provided in the photo-interrupter 654, and outputted as a detection signal of the air bubble sensor BS1. That is, when the liquid flows from the nipple 652 into the nipple 653 through the flow path 651, the air bubble sensor BS1 outputs the signal "0" while the flow path 651 is filled with the liquid, and outputs the signal "1" while the photo-receptive element 656 cannot receive the light LT due to the presence of air bubbles in the flow path 651. The air bubble sensor BS2 operates in the same manner as in the air bubble BS1. For example, GP1A05E commercially available from Sharp Kabushiki Kaisha can be used for the photo-interrupter 654.

Figure 55:
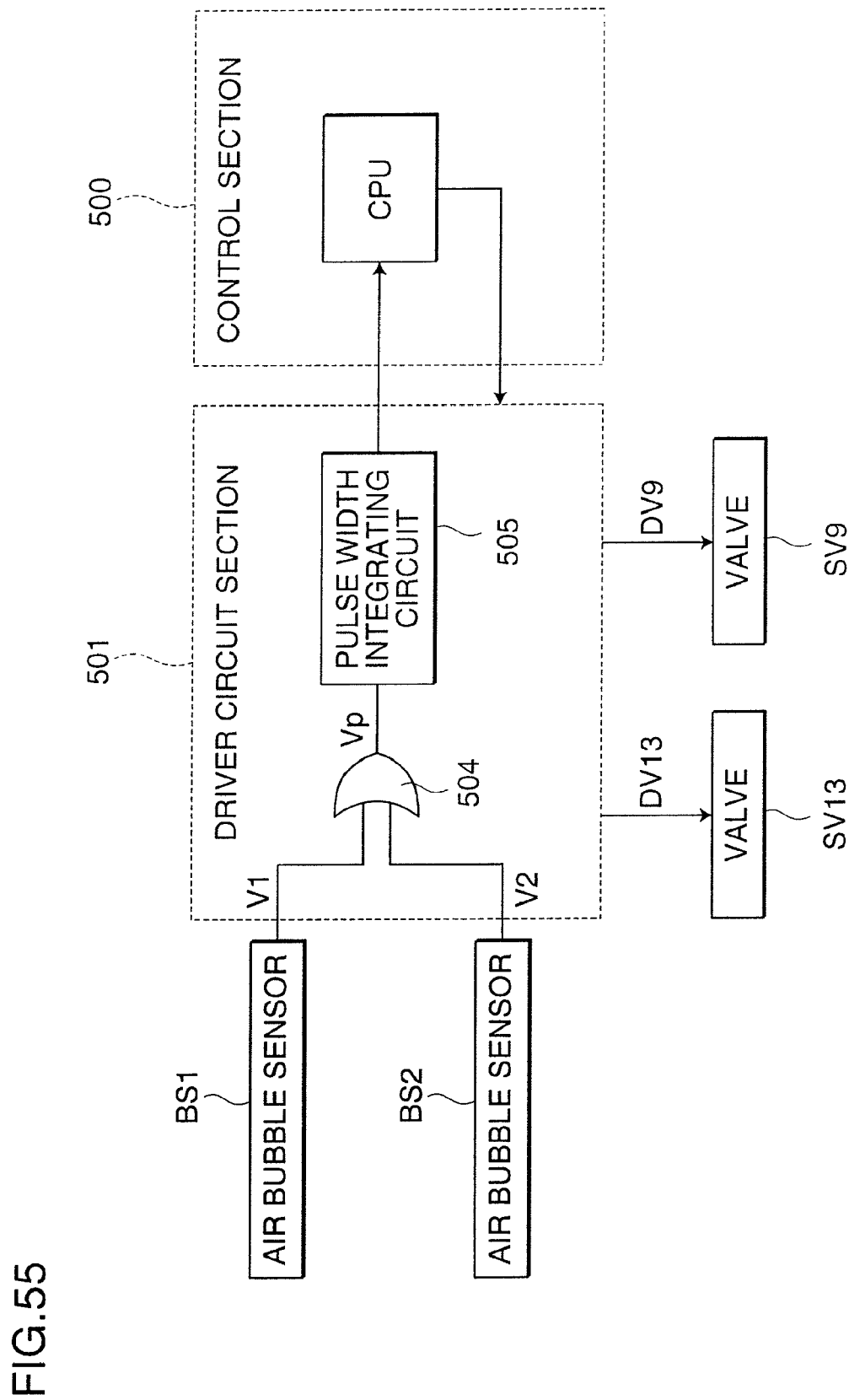
FIG. 55 is a signal processing circuit diagram for processing respectively output signals from the air bubble sensors according to this invention.

FIG. 55 is a circuit diagram illustrating a signal processing circuit in which the control section 500 (FIG. 43) judges whether air bubbles are generated by receiving respectively outputs V1, V2 from the air bubble sensors BS1, BS2.

The drive circuit section 501 (FIG. 43) includes an OR gate 504 and a pulse width integrating circuit 505 for integrating periods (pulse widths) during which the signal "1" is outputted from the OR gate 504. A logical sum Vp of the outputs V1, V2 (binary signals) from the air bubble sensors BS1, BS2 is calculated to be outputted to the pulse width integrating circuit 505. As described above, the control section 500 including the CPU controls the drive circuit section 501, and allows valves SV13, SV9 to be driven.

Figure 56:
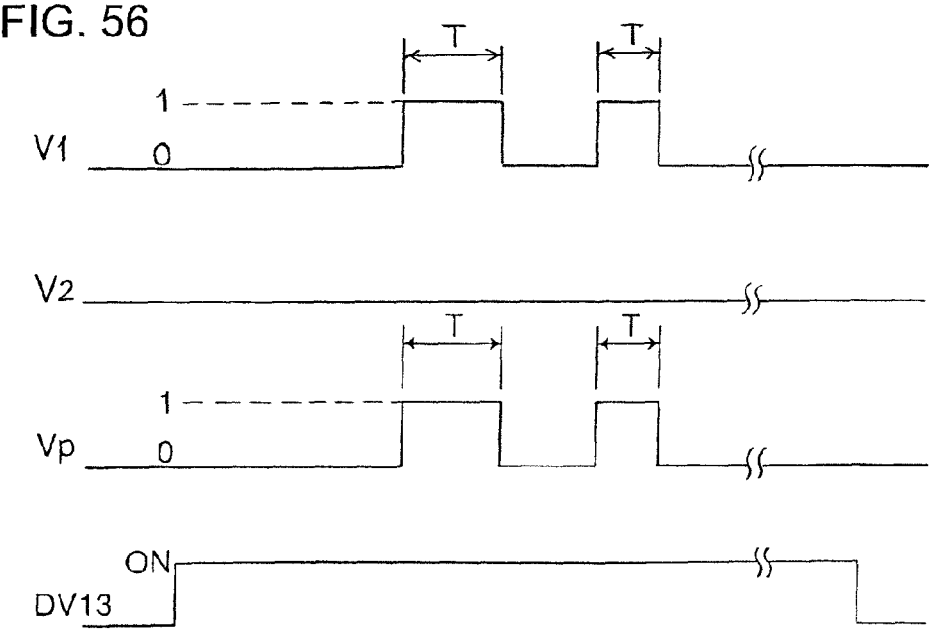
FIG. 56 is a timing chart illustrating the signals of the circuit shown in FIG. 55.
Figure 57:
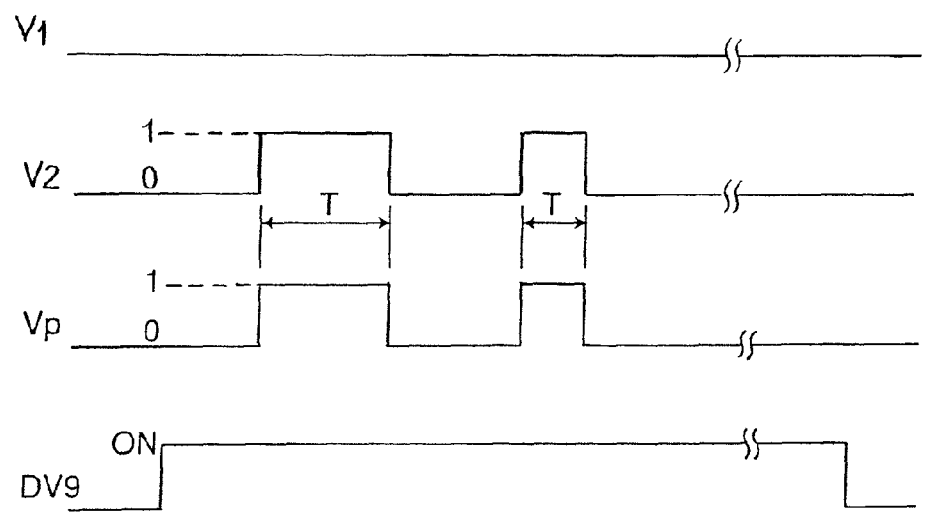
FIG. 57 is a timing chart illustrating the signals of the circuit shown in FIG. 55.

FIGS. 56 and 57 are timing charts illustrating respectively a relationship between a driving voltage DV13 of the valve SV13 and the output Vp from the OR gate 504, and a relationship between a driving voltage DV9 of the valve SV9 and the output Vp from the OR gate 504.

As shown in FIG. 56, the driving voltage DV13 is turned on, and the valve SV13 is driven, whereby the diluent is transported from the diluent container 101 (FIG. 42) into the diluent chamber SC1 (FIG. 42). At this time, where the air bubble sensor BS1 detects air bubbles, the output V1 from the air bubble sensor BS1 is represented as a pulse signal.

On the other hand, the air bubble sensor BS2 is filled with the hemolyzing agent, so that the output V2 remains the signal "0". Since the output Vp from the OR gate is the logical sum of the outputs V1, V2, the output Vp is represented as a pulse signal shown in FIG. 56.

The pulse width integrating circuit 505 integrates periods T during which the output Vp is changed to the signal "1" within a predetermined time period, and the periods T thus integrated are outputted to the control section 500. The control section 500 judges whether to generate the air bubbles on the basis of an integrated value, and then compares the integrated value with a predetermined value. At this time, where the integrated value is larger than the predetermined value, the control section 500 judges that the diluent is not transported to the diluent chamber SC1. That is, the diluent container 101 is determined empty by the control section 500. Thereafter, the control section 500 causes the display section 3 to display the judgment on the display 3a. That is, the control section 500 judges that no diluent is present in the diluent container 101 when the driving voltage DV13 of the valve SV13 is turned on and the integrated value obtained within the predetermined time period is larger than the predetermined value.

As shown in FIG. 57, the driving voltage DV9 is turned on, and the valve SV9 is driven, whereby the hemolyzing agent is transported from the hemolyzing agent container 103 (FIG. 42) into the hemolyzing chamber SC2 (FIG. 42). At this time, where the air bubble sensor BS2 detects air bubbles, the output V2 from the air bubble sensor BS2 is represented as a pulse signal.

On the other hand, the air bubble sensor BS1 is filled with the diluent, so that the output V1 remains the signal "0". Since the output Vp from the OR gate 504 is the logical sum of the outputs V1, V2, the output Vp is represented as a pulse signal shown in FIG. 57.

The pulse width integrating circuit 505 integrates periods T during which the output Vp is changed to the signal "1" within the predetermined time period, and the periods T thus integrated are outputted to the control section 500. The control section 500 judges whether to generate the air bubbles on the basis of an integrated value, and then compares the integrated value with the predetermined value. At this time, where the integrated value is larger than the predetermined value, the control section 500 judges that the hemolyzing agent is not transported to the hemolyzing agent chamber SC2. That is, the hemolyzing agent container 103 is determined empty by the control section 500. Thereafter, the control section 500 causes the display section 3 to display the judgment on the display 3a. That is, the control section 500 judges that no hemolyzing agent is present in the hemolyzing agent container 103 when the driving voltage DV9 of the valve SV9 is turned on and the integrated value obtained within the predetermined time period is larger than the predetermined value.

Figure 58:
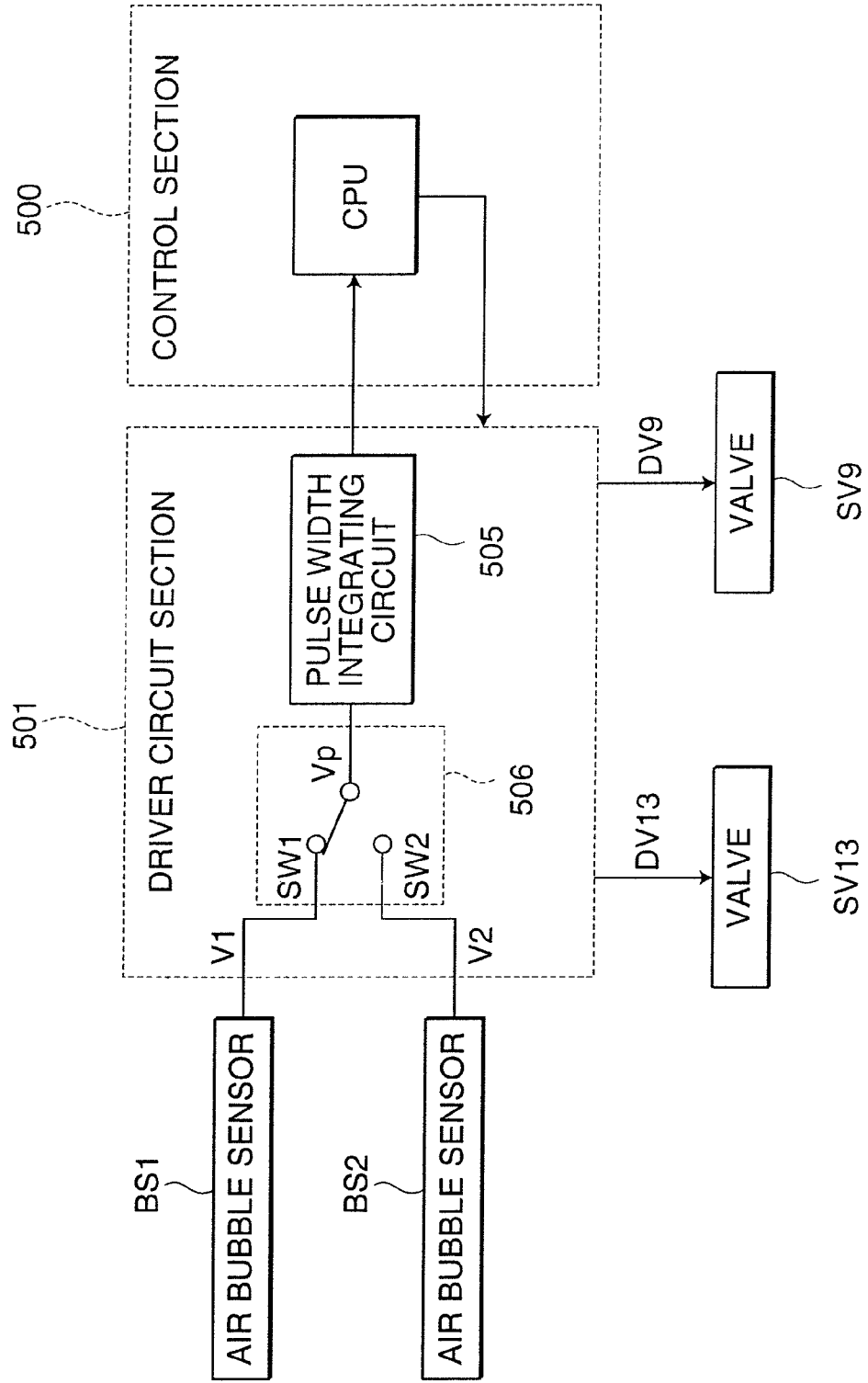
FIG. 58 is a circuit diagram illustrating another exemplary signal processing circuit.

FIG. 58 is a circuit diagram illustrating another exemplary signal processing circuit in which the control section 500 (FIG. 43) judges whether air bubbles are generated by receiving respectively the outputs V1, V2 from the air bubble sensors BS1, BS2. In this circuit, a switching circuit 506 is used instead of the OR gate of the signal processing circuit shown in FIG. 55.

Figure 59:
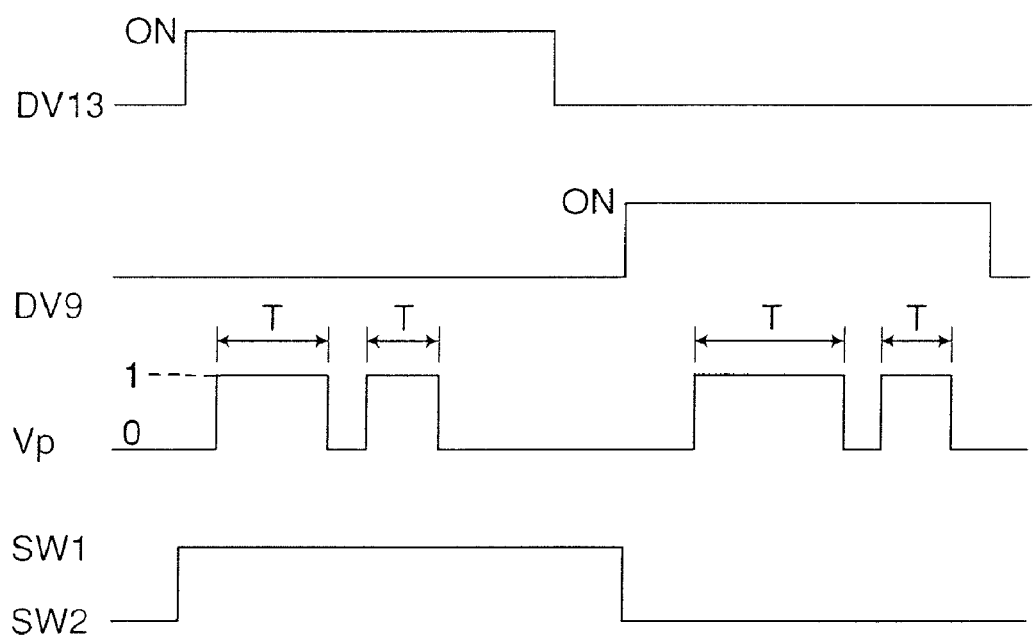
FIG. 59 is a timing chart illustrating the signals of the circuit shown in FIG. 58.

FIG. 59 is a timing chart illustrating a relationship among the driving voltages DV13, DV9 of the respective valves SV13, SV9, the output Vp from the OR gate 504 and the switching operation of the switching circuit 506.

As shown in FIG. 59, the driving voltage DV13 is turned on, and a switch of the switching circuit 506 is switched to SW1, whereby the output Vp inputted to the pulse width integrating circuit 505 becomes equal to the output V1. The pulse width integrating circuit 505 integrates periods T during which the output Vp is changed to the signal "1" within the predetermined time period, and the periods T thus integrated are outputted to the control section 500. The control section 500 judges whether to generate the air bubbles on the basis of an integrated value, and then compares the integrated value with the predetermined value. At this time, where the integrated value is larger than the predetermined value, the control section 500 judges that the diluent is not transported to the diluent chamber SC1. Thereafter, the control section 500 causes the display section 3 to display the judgment on the display 3a. That is, the control section 500 judges that no diluent is present in the diluent container 101 when the driving voltage DV13 of the valve SV13 is turned on and the integrated value obtained within the predetermined time period is larger than the predetermined value.

As shown in FIG. 59, the driving voltage DV9 is turned on, and the switch of the switching circuit 506 is switched to SW2, whereby the output Vp inputted to the pulse width integrating circuit 505 becomes equal to the output V2. The pulse width integrating circuit 505 integrates the periods T during which the output Vp is changed to the signal "1" within the predetermined time period, and the periods T thus integrated are outputted to the control section 500. The control section 500 judges whether to generate the air bubbles on the basis of the integrated value, and then compares the integrated value with the predetermined value. At this time, where the integrated value is larger than the predetermined value, the control section 500 judges that the hemolyzing agent is not transported to the hemolyzing agent chamber SC2. Thereafter, the control section 500 causes the display section 3 to display the judgment on the display 3a. That is, the control section 500 judges that no hemolyzing agent is present in the hemolyzing container 103 when the driving voltage DV9 of the valve SV9 is turned on and the integrated value obtained within the predetermined time period is larger than the predetermined value.

Figure 60:
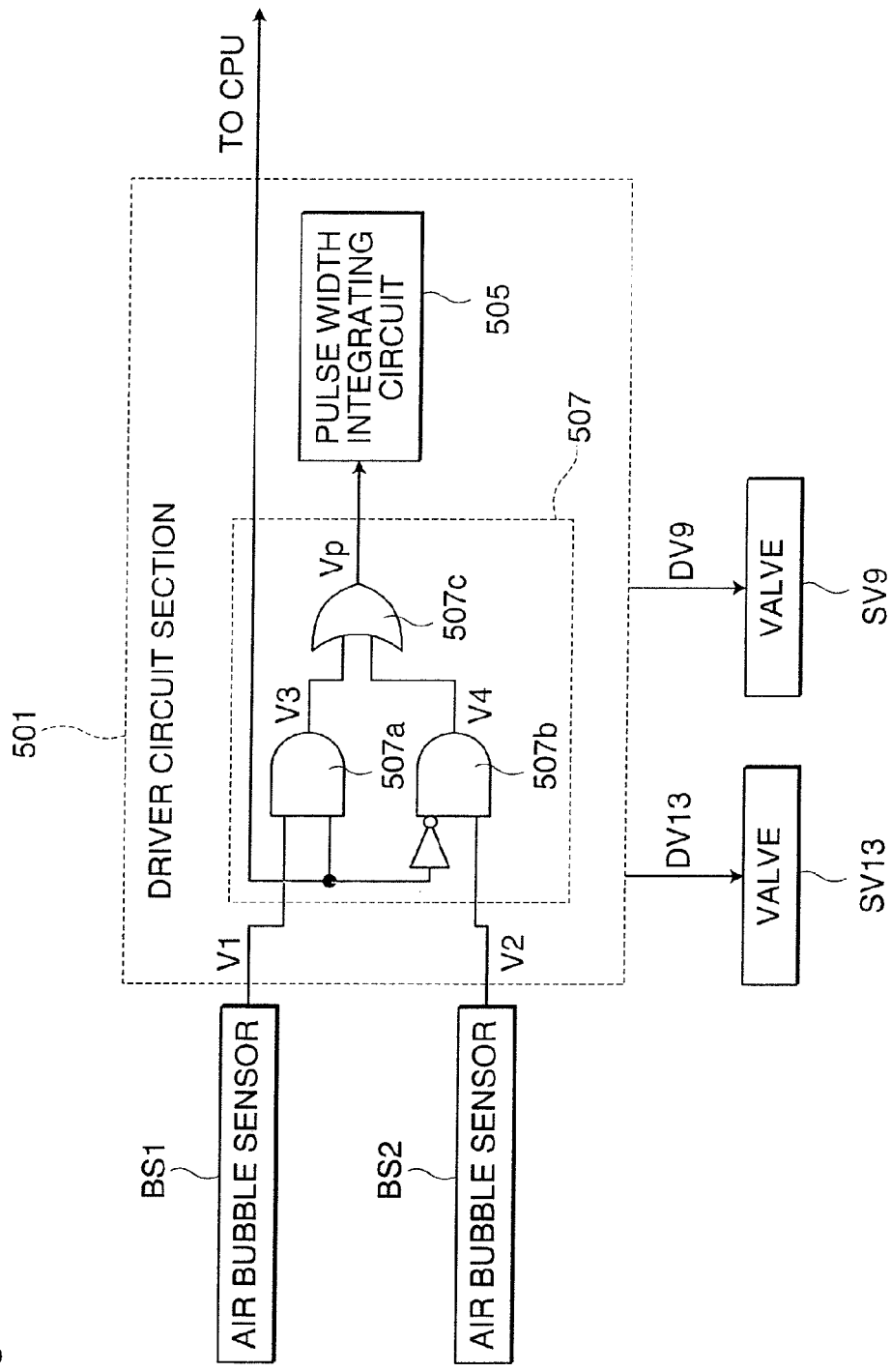
FIG. 60 is a circuit diagram illustrating another exemplary switching circuit.

FIG. 60 is an exemplary of another switching circuit which can be used instead of the switching circuit 506 of FIG. 58. A switching circuit 507 comprises two AND gates 507a, 507b and an OR gate 507c.

Where an output from the CPU is the signal "1", the signal "1" is inputted to the AND gate 507a and the signal "0" is inputted to the AND gate 507b. Therefore, an output V3 from the AND gate 507a is changed to the signal "1" only when the output V1 is the signal "1". On the other hand, an output V4 from the AND gate 507b is changed to the signal "0" irrespective of the signal of the output V2 from the air bubble sensor BS2. That is, the output Vp becomes equal to the output V1 when the output from the CPU is the signal "1".

Where the output from the CPU is the signal "0", the signal "0" is inputted to the AND gate 507a and the signal "1" in inputted to the AND gate 507b. Therefore, the output V3 from the AND gate 507a is changed to the signal "0" irrespective of the signal of output V1 from the air bubble sensor BS1. On the other hand, the output V4 from the AND gate 507b is changed to the signal "1" only when the output V2 from the air bubble sensor BS2 is the signal "1". That is, the output Vp becomes equal to the output V2 when the output from the CPU is the signal "0".

According to this invention, the liquid aspirator has the plurality of elongated recesses formed in the outer surface of the hollow pipe thereof. When the liquid aspirator is stuck into the sample vessel with the rubber cap, the inside of the sample vessel immediately communicates with the atmosphere through each of the recesses. Therefore, the sample can smoothly be sucked and quantified through the liquid aspirator, so that analysis accuracy can be improved. At least one of the recesses can be prevented from being filled with the rubber cap when the liquid aspirator virtually reaches the bottom of the sample vessel. In addition, when the exterior of the liquid aspirator is cleaned, the recesses are cleaned at the same time, and therefore the analyzer does not need to further provide a cleaning flow system for cleaning the recesses.

What is claimed is:

1. A blood cell analyzer, comprising;
a diluent chamber;
a first flow path for transporting a diluent contained in a diluent container to the diluent chamber;
a pump for supplying a negative pressure for transporting the diluent from the diluent container to the diluent chamber through the first flow path;
an air bubble sensor for detecting an air bubble in the first flow path;
a second flow path for communicating the diluent chamber and the pump which supplies the negative pressure to the diluent container through the second flow path, the diluent chamber and the first flow path;
a valve for opening and closing the second flow path; and
a controller for controlling the valve so that the valve closes the second flow path when the air bubble sensor of the first flow path has kept detecting the air bubble for a time period longer than a first predetermined time period.

2. The blood cell analyzer of claim 1, further comprising:
a preparing section for preparing an analysis sample using at least a blood sample and the diluent reagent contained in the diluent chamber, and
an analyzing section for analyzing the prepared analysis sample.

3. The blood cell analyzer of claim 1, further comprising:
a second chamber;
a third flow path for transporting a hemolyzing agent from a hemolyzing agent container to the second chamber;
a fourth flow path for communicating the second chamber and the pump;
a second valve for opening and closing the fourth flow path; and
a second air bubble sensor for detecting an air bubble in the third flow path,
wherein the pump supplies a pressure for transporting the hemolyzing agent from the hemolyzing agent container to the second chamber, and
wherein the controller controls the second valve so that the second valve closes the fourth flow path when the second air bubble sensor of the third flow path has kept detecting air bubble for a time period longer than a second predetermined time period.

4. The blood cell of claim 1, further comprising:
a display,
wherein the controller controls the display so that the display displays information indicating that the diluent container is empty when the air bubble sensor has kept detecting air bubble for the time period longer than the first predetermined time period.

5. A blood cell analyzer, comprising:
a diluent chamber;
a first flow path for transporting a diluent contained in a diluent container to the diluent chamber;
a pump for supplying a negative pressure for transporting the diluent from the diluent container to the diluent chamber through the first flow path;
a sensor for detecting whether the diluent exists or not in the first flow path;
a second flow path for communicating the diluent chamber and the pump which supplies the negative pressure to the diluent container through the second flow path, the diluent chamber and the first flow path;
a valve for opening and closing the second flow path; and
a controller for controlling the valve so that the valve closes the second flow path when the sensor has detected that the diluent does not exist in the first flow path.

6. The blood cell of claim 5, further comprising:
a preparing section for preparing an analysis sample using a sample and the diluent contained in the diluent chamber, and
an analyzing section for analyzing the prepared analysis sample.

7. The blood cell analyzer of claim 5, further comprising:
a second chamber;
a third flow path for transporting a hemolyzing agent from a hemolyzing agent container to the second chamber;
a fourth flow path for communicating the second chamber and the pump;
a second valve for opening and closing the fourth flow path; and
a second sensor for detecting whether the hemolyzing agent exists or not in the third flow path,
wherein the pump supplies a pressure for transporting the hemolyzing agent from the hemolyzing agent container to the second chamber, and
wherein the controller controls the second valve so that the second valve closes the fourth flow path when the second sensor has detected that the hemolyzing agent does not exist in the third flow path.

8. The blood cell analyzer of claim 5, further comprising:
a display,
wherein the controller controls the display so that the display displays information indicating that the diluent container is empty when the sensor has detected that the diluent does not exist in the flow path.

9. The blood cell analyzer of claim 5, wherein the controller controls the valve so that the valve closes the flow path when the sensor has kept detecting the detected result for a time period longer than a predetermined time period.

10. The blood cell analyzer of claim 2, further comprising:
a blood cell detector for detecting blood cells in the analysis sample prepared by the preparing section,
wherein the preparing section comprises a mixing chamber for mixing at least the blood sample and the diluent supplied from the diluent chamber, and a pipette for aspirating the blood sample in a container and for discharging the aspirated blood sample to the mixing chamber, and
wherein the analyzing section analyzes a detected result by the blood cell detector.

11. The blood cell analyzer of claim 10, further comprising:
a second pump for supplying the diluent from the diluent chamber to the mixing chamber; and
a third pump for supplying the analysis sample from the mixing chamber to the blood cell detector.

12. The blood cell analyzer of claim 6, further comprising:
a blood cell detector for detecting blood cells in the analysis sample prepared by the preparing section,
wherein the preparing section comprises a mixing chamber for mixing at least the blood sample and the diluent supplied from the diluent chamber, and a pipette for aspirating the blood sample in a container and for discharging the aspirated blood sample to the mixing chamber, and
wherein the analyzing section analyzes a detected result by the blood cell detector.

13. The blood cell analyzer of claim 12, further comprising:
a second pump for supplying the diluent from the diluent chamber to the mixing chamber; and
a third pump for supplying the analysis sample from the mixing chamber to the blood cell detector.

* * * * *